US012788301B2

(12) United States Patent
Sharvit et al.

(10) Patent No.: US 12,788,301 B2
(45) Date of Patent: Nov. 10, 2026

(54) SYSTEMS, METHODS, AND COMPUTER PROGRAM PRODUCTS FOR IMPROVED CARDIAC DIAGNOSIS AND/OR MONITORING WITH ECG SIGNALS

(71) Applicant: ZOLL Medical Corporation, Chelmsford, MA (US)

(72) Inventors: Vered Cohen Sharvit, Modi'in-Maccabim-Re'ut (IL); Dongfeng Han, Pittsburgh, PA (US); Jeffery T. Mitchell, Mars, PA (US); Rafael Ravid, Savyon (IL); Michael A. Sipe, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 260 days.

(21) Appl. No.: 18/387,248

(22) Filed: Nov. 6, 2023

(65) Prior Publication Data

US 2024/0148310 A1 May 9, 2024

Related U.S. Application Data

(60) Provisional application No. 63/423,348, filed on Nov. 7, 2022.

(51) Int. Cl.
*A61B 5/364* (2021.01)
*A61B 5/00* (2006.01)
(Continued)

(52) U.S. Cl.
CPC .............. *A61B 5/364* (2021.01); *A61B 5/279* (2021.01); *A61B 5/332* (2021.01); *A61B 5/6805* (2013.01); *G16H 40/67* (2018.01); *G16H 50/20* (2018.01)

(58) Field of Classification Search
CPC ......... A61B 5/364; A61B 5/279; A61B 5/332; A61B 5/6805; A61B 5/349; A61B 5/7264;
(Continued)

(56) References Cited

U.S. PATENT DOCUMENTS

| | | | | |
|---|---|---|---|---|
| 6,253,099 B1 | 6/2001 | Oskin et al. | | |
| 8,352,018 B2 * | 1/2013 | Xue | A61B 5/0006 | 600/509 |

(Continued)

FOREIGN PATENT DOCUMENTS

| | | | |
|---|---|---|---|
| WO | 2012011066 A1 | 1/2012 | |
| WO | 2016115175 A1 | 7/2016 | |
| WO | WO-2021211564 A1 * | 10/2021 | G16H 10/60 |

OTHER PUBLICATIONS

Adams, "iRhythm snags FDA approval for AFib characterization algorithm used in Verily's wearable", MedCity News, Jul. 2022, pp. 1-5. Retrieved from https://medcitynews.com/2022/07/irhythm-snags-fda-approval-for-afib-characterization-algorithm-used-in-verilys-wearable/ [Accessed Jul. 25, 2022].

(Continued)

*Primary Examiner* — Michael J Lau
(74) *Attorney, Agent, or Firm* — The Webb Law Firm

(57) ABSTRACT

Systems, methods, and computer program products identify arrhythmias experienced by a patient. A system includes an external wearable heart monitoring device for continuous and long-term monitoring of a patient that includes electrocardiogram (ECG) electrodes and circuitry to sense surface ECG activity and provide ECG channel(s) producing ECG signal(s), a non-transitory computer-readable medium including an arrhythmia classifier including neural network(s), and processor(s). The neural network(s) are trained based on a historical collection of ECG signal portions with annotation data including at least one anno- (Continued)

tation for each ECG signal portion and based on weight data including a weight for each annotation based on the annotator thereof. The processor(s) receive the ECG signal(s), monitor the ECG signal(s) to detect at least one arrhythmia event based on the arrhythmia classifier, and transmit at least one communication based on the arrhythmia event(s) to a remote computer system.

9 Claims, 30 Drawing Sheets

(51) Int. Cl.
*A61B 5/279* (2021.01)
*A61B 5/332* (2021.01)
*G16H 40/67* (2018.01)
*G16H 50/20* (2018.01)

(58) Field of Classification Search
CPC ....... A61B 5/363; A61B 5/7267; A61B 5/361; A61B 5/0006; G16H 40/67; G16H 50/20; G16H 50/70
See application file for complete search history.

(56) References Cited

U.S. PATENT DOCUMENTS 10,463,269 B2 11/2019 Boleyn et al.
10,896,747 B2 * 1/2021 Lyman ................. A61B 5/7264
10,959,660 B2 * 3/2021 Li .......................... A61B 5/349
11,083,371 B1 * 8/2021 Szabados ............. A61B 5/0006
11,723,577 B2 * 8/2023 Pedalty ................ A61B 5/0205 600/518
2011/0130800 A1 6/2011 Weinstein et al.
2016/0135706 A1 5/2016 Sullivan et al.
2016/0183833 A1 * 6/2016 Kuppuraj ............. A61B 5/0006 600/515
2020/0375493 A1 * 12/2020 Kranz .................. A61B 5/0006
2021/0121090 A1 * 4/2021 Weinstein ............ A61B 5/0006
2021/0343416 A1 * 11/2021 Chakravarthy ....... A61B 5/1116
2022/0068483 A1 * 3/2022 Goldberg ............... A61B 5/367
2022/0344025 A1 * 10/2022 Bort ....................... A61B 5/367
2023/0335244 A1 * 10/2023 Hagenbrock .......... G16H 15/00
2025/0235143 A1 * 7/2025 Bassi ..................... A61B 5/339

OTHER PUBLICATIONS

"ASSURE Wearable Cardioverter Defibrillator (WCD) System Instructions for Use", ASSURE Cardiac Recovery System, 2021, pp. 1-88, Kestra Medical Technologies, Inc., Kirkland, WA.
"ASSURE Wearable Defibrillator Patient Handbook", ASSURE Cardiac Recovery System, 2021, pp. 1-342, Kestra Medical Technologies, Inc., Kirkland, WA.

* cited by examiner

200

300

400

1400

SYSTEMS, METHODS, AND COMPUTER PROGRAM PRODUCTS FOR IMPROVED CARDIAC DIAGNOSIS AND/OR MONITORING WITH ECG SIGNALS

CROSS-REFERENCE TO RELATED APPLICATION

This application claims priority to U.S. Provisional Patent Application No. 63/423,348 filed Nov. 7, 2022, the disclosure of which is hereby incorporated by reference in its entirety.

FIELD OF THE DISCLOSURE

Embodiments of the current disclosure are directed toward cardiac diagnosis and/or monitoring with electrocardiogram (ECG) signals.

BACKGROUND OF THE DISCLOSURE

There is a wide variety of electronic and mechanical devices for monitoring and/or treating patients' medical conditions. In some examples, depending on the underlying medical condition being monitored and/or treated, medical devices, such as cardiac monitors or defibrillators, may be surgically implanted or externally connected to the patient. In some cases, physicians may use medical devices alone or in combination with drug therapies to treat conditions such as cardiac arrhythmias. Cardiac monitoring and/or treatment devices transmit ECG-based biometric data for additional analysis at a remote server. Systems, methods, and computer program products are desired to reliably and efficiently transmit large amounts of data for accurate analysis. Systems, methods, and computer program products are desired for accurate analysis of cardiac events of interest.

SUMMARY

Embodiments of the current disclosure include a wearable atypical electrocardiogram (ECG) lead arrhythmia monitoring system for identifying arrhythmias experienced by a patient. In some embodiments, the system may include an external wearable heart monitoring device configured for continuous and long-term monitoring of a patient comprising a plurality of ECG electrodes and associated circuitry configured to sense surface ECG activity of the patient, each ECG electrode configured to be anatomically located within a circumferential atypical zone of the patient's torso in an uninhibiting manner so as to allow for the patient to be ambulatory, wherein the plurality of ECG electrodes and associated circuitry are configured to provide at least one atypical ECG channel producing at least one atypical ECG signal for the patient. In some embodiments, the system may include a non-transitory computer-readable medium comprising an arrhythmia classifier comprising at least one neural network, wherein the neural network is trained based on a historical collection of a plurality of atypical ECG signal portions with annotation data, the annotation data comprising at least one respective annotation for each respective atypical ECG signal portion of the plurality of atypical ECG signal portions, and wherein the neural network is further trained based on weight data for the annotation data of the plurality of atypical ECG signal portions, the weight data comprising a respective weight for each respective annotation based on a respective annotator of the respective annotation. In some embodiments, the system may include at least one processor operatively connected to the at least one atypical ECG channel and the non-transitory computer-readable medium. The at least one processor may be configured to receive the at least one atypical ECG signal of the at least one atypical ECG channel, monitor the at least one atypical ECG signal to detect at least one arrhythmia event based on the arrhythmia classifier, and transmit at least one communication based on the at least one arrhythmia event to a remote computer system.

In some embodiments, the plurality of ECG electrodes comprises at least four ECG electrodes.

In some embodiments, the at least one atypical ECG channel comprises at least two atypical ECG channels, each atypical ECG channel associated with two respective ECG electrodes of the at least four ECG electrodes.

In some embodiments, the at least four ECG electrodes comprise a front ECG electrode, a back ECG electrode, a first side ECG electrode, and a second side ECG electrode, wherein the at least two atypical ECG channels comprise a front-to-back (FB) ECG channel associated with the front ECG electrode and the back ECG electrode, and wherein the at least two typical ECG channels further comprise a side-to-side (SS) ECG channel associated with the first side ECG electrode and the second side ECG electrode.

In some embodiments, the at least two atypical ECG channels comprise a first atypical ECG channel and a second atypical ECG channel substantially orthogonal to the first atypical ECG channel.

In some embodiments, the at least one atypical ECG channel comprises at least three atypical ECG channels.

In some embodiments, the at least one atypical ECG channel comprises at least four atypical ECG channels.

In some embodiments, the at least one atypical ECG channel comprises a front-to-back (FB) ECG channel.

In some embodiments, the at least one atypical ECG channel comprises a side-to-side (SS) ECG channel.

In some embodiments, the at least one atypical ECG channel comprises at least one dynamically defined atypical ECG channel.

In some embodiments, the associated circuitry is configured to analyze surface ECG activity of the patient and select at least two of the plurality of ECG electrodes to define the at least one dynamically defined atypical ECG channel.

In some embodiments, the respective weight for each respective annotator is based on a respective skill level of the respective annotator.

In some embodiments, the respective skill level for each respective annotator comprises a skill score.

In some embodiments, the skill score comprises an integer value from one to four.

In some embodiments, the skill score comprises an integer value from one to five.

In some embodiments, the skill score comprises an integer value from one to ten.

In some embodiments, the skill score comprises an integer value from one to 100.

In some embodiments, the skill score comprises one of 25, 50, 75, or 100.

In some embodiments, the skill score comprises a value from zero to one.

In some embodiments, the remote computer system is configured to receive a plurality of skill scores comprising a respective skill score for each respective annotator, wherein a plurality of annotators comprises each respective annotator. In some embodiments, the remote system is configured to determine the respective weight for each respective annotator based on the plurality of skill scores.

In some embodiments, the remote computer system is further configured to receive the historical collection of the plurality of atypical ECG signal portions with the annotation data and train the arrhythmia classifier based on the historical collection of the plurality of atypical ECG signal portions with the annotation data and based on the weight data.

In some embodiments, the at least one communication comprises at least one further atypical ECG signal portion associated with the at least one arrhythmia event. In some embodiments, the remote computer system is further configured to receive the at least one communication comprising the at least one further atypical ECG signal portion and receive further annotation data associated with the at least one further atypical ECG signal portion from at least one annotator of the plurality of annotators.

In some embodiments, the remote computer system is further configured to compare the further annotation data to the at least one arrhythmia event detected based on the arrhythmia classifier and determine an updated weight for each respective annotator of the at least one annotator based on comparing the further annotation data to the at least one arrhythmia event.

In some embodiments, the remote computer system is further configured to retrain the arrhythmia classifier based on the at least one further atypical ECG signal portion, the further annotation data, and the updated weight data.

In some embodiments, the remote computer system is further configured to compare the further annotation data to the at least one arrhythmia event detected based on the arrhythmia classifier and transmit at least one further communication based on comparing the further annotation data to the at least one arrhythmia event.

In some embodiments, the at least one further communication comprises at least one of a recommendation to retest one or more of the at least one annotator, a recommendation to increase the respective skill score of one or more of the at least one annotator, a recommendation to decrease the respective skill score of one or more of the at least one annotator, or any combination thereof.

In some embodiments, the remote computer system is further configured to retrain the arrhythmia classifier based on the at least one further atypical ECG signal portion, the further annotation data, and the weight data.

In some embodiments, the remote computer system is configured to receive at least one updated skill score comprising a respective updated skill score for each of at least one annotator of the plurality of annotators, determine a respective updated weight for each of the at least one annotator based on the at least one updated skill score, and retrain the arrhythmia classifier based on the respective updated weight for each of the at least one annotator.

In some embodiments, training the arrhythmia classifier comprises adjusting a hyperparameter of a loss function of the arrhythmia classifier based on the weight data.

In some embodiments, training the arrhythmia classifier comprises adjusting the respective weight for each of at least one annotator of the plurality of annotators based on a hyperparameter tuning process.

In some embodiments, the respective skill score for each respective annotator of the plurality of annotators comprises an initial skill score, the respective weight for each respective annotator comprises an initial weight, the historical collection of the plurality of atypical ECG signal portions with the annotation data comprises a training subset of the plurality of atypical ECG signal portions and a validation subset of the plurality of atypical ECG signal portions, and the respective weight for each of the at least one annotator comprises a hyperparameter and an initial value of the hyperparameter comprises the initial weight. In some embodiments, the hyperparameter tuning process comprises training the arrhythmia classifier based on the training subset and the initial value of the hyperparameter, determining a metric associated with the initial value of the hyperparameter based on the validation subset, adjusting a value of the hyperparameter to provide an adjusted value of the hyperparameter, retraining the arrhythmia classifier based on the training subset and the adjusted value of the hyperparameter, and determining the metric associated with the adjusted value of the hyperparameter based on the validation set.

In some embodiments, the hyperparameter tuning process further comprises repeating adjusting of the value of the hyperparameter, retraining of the arrhythmia classifier, and determining of the metric associated with the adjusted value of the hyperparameter until a termination condition is satisfied.

In some embodiments, repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of a value of the hyperparameter that optimizes the metric is found, a maximum number of iterations is reached, or any combination thereof.

In some embodiments, the metric comprises at least one of accuracy, loss, area under curve (AUC), precision, recall, F1 score, or any combination thereof.

In some embodiments, adjusting the value of the hyperparameter comprises at least one of adjusting the value of the hyperparameter within a search space, adjusting the value of the hyperparameter within a range around the initial value, adjusting the value of the hyperparameter within a range around the initial skill score, adjusting the value of the hyperparameter randomly, or any combination thereof.

In some embodiments, the external wearable heart monitoring device comprises a garment configured to be worn about a torso of the patient for an extended period of time and further configured to house the plurality of ECG electrodes.

In some embodiments, the garment comprises a plurality of receptacles configured to receive the plurality of ECG electrodes.

In some embodiments, the external wearable heart monitoring device comprises a plurality of therapy electrodes configured to be housed in the garment.

In some embodiments, the external wearable heart monitoring device is configured to determine whether the patient is experiencing a treatable cardiac arrhythmia and deliver one or more therapeutic shocks to the patient via the plurality of therapy electrodes upon determining that the patient is experiencing a treatable cardiac arrhythmia.

Embodiments of the current disclosure include a wearable atypical electrocardiogram (ECG) lead arrhythmia monitoring system for identifying arrhythmias experienced by a patient. In some embodiments, the system includes an external wearable heart monitoring device configured for continuous and long-term monitoring of a patient comprising a plurality of ECG electrodes and associated circuitry configured to sense surface ECG activity of the patient, each ECG electrode configured to be anatomically located on the patient's thorax superior to the patient's xiphoid process and lateral to the patient's sternum, in an uninhibiting manner so as to allow for the patient to be ambulatory, wherein the plurality of ECG electrodes and associated circuitry are configured to provide at least one atypical ECG channel producing at least one atypical ECG signal for the patient. In some embodiments, the system includes a non-transitory computer-readable medium comprising an arrhythmia classifier comprising at least one neural network, wherein the neural network is trained based on a historical collection of a plurality of atypical ECG signal portions with annotation data, the annotation data comprising at least one respective annotation for each respective atypical ECG signal portion of the plurality of atypical ECG signal portions, and wherein the neural network is further trained based on weight data for the annotation data of the plurality of atypical ECG signal portions, the weight data comprising a respective weight for each respective annotation based on a respective annotator of the respective annotation. In some embodiments, the system includes at least one processor operatively connected to the at least one atypical ECG channel and the non-transitory computer-readable medium, the at least one processor configured to receive the at least one atypical ECG signal of the at least one atypical ECG channel, monitor the at least one atypical ECG signal to detect at least one arrhythmia event based on the arrhythmia classifier, and transmit at least one communication based on the at least one arrhythmia event to a remote computer system.

In some embodiments, at least two ECG electrodes of the plurality of ECG electrodes are disposed within a predetermined distance on the patient's thorax superior to the patient's xiphoid process and lateral to the patient's sternum.

In some embodiments, the predetermined distance comprises 15 centimeters, and wherein the at least two ECG electrodes are spaced less than 15 centimeters.

In some embodiments, the at least two ECG electrodes are spaced less than 10 centimeters.

In some embodiments, the at least two ECG electrodes are spaced 5-15 centimeters.

In some embodiments, the at least two ECG electrodes are spaced less than 5 centimeters.

In some embodiments, the external wearable heart monitoring device comprises a single adhesive patch.

In some embodiments, the plurality of ECG electrodes are all on one side of the patient's sternum.

In some embodiments, the plurality of ECG electrodes are left lateral to the patient's sternum.

In some embodiments, the plurality of ECG electrodes are right lateral to the patient's sternum.

In some embodiments, the respective weight for each respective annotator is based on a respective skill level of the respective annotator.

In some embodiments, the respective skill level for each respective annotator comprises a skill score.

In some embodiments, the skill score comprises an integer value from one to four.

In some embodiments, the skill score comprises an integer value from one to five.

In some embodiments, the skill score comprises an integer value from one to ten.

In some embodiments, wherein the skill score comprises an integer value from one to 100.

In some embodiments, wherein the skill score comprises one of 25, 50, 75, or 100.

In some embodiments, the skill score comprises a value from zero to one.

In some embodiments, the remote computer system is configured to: receive a plurality of skill scores comprising a respective skill score for each respective annotator, wherein a plurality of annotators comprises each respective annotator, and determine the respective weight for each respective annotator based on the plurality of skill scores.

In some embodiments, the remote computer system is configured to receive the historical collection of the plurality of atypical ECG signal portions with the annotation data and train the arrhythmia classifier based on the historical collection of the plurality of atypical ECG signal portions with the annotation data and based on the weight data.

In some embodiments, the at least one communication comprises at least one further atypical ECG signal portion associated with the at least one arrhythmia event. In some embodiments, the remote computer system is further configured to receive the at least one communication comprising the at least one further atypical ECG signal portion and receive further annotation data associated with the at least one further atypical ECG signal portion from at least one annotator of the plurality of annotators.

In some embodiments, the remote computer system is further configured to compare the further annotation data to the at least one arrhythmia event detected based on the arrhythmia classifier and determine an updated weight for each respective annotator of the at least one annotator based on comparing the further annotation data to the at least one arrhythmia event.

In some embodiments, the remote computer system is further configured to retrain the arrhythmia classifier based on the at least one further atypical ECG signal portion, the further annotation data, and the updated weight data.

In some embodiments, the remote computer system is further configured to compare the further annotation data to the at least one arrhythmia event detected based on the arrhythmia classifier and transmit at least one further communication based on comparing the further annotation data to the at least one arrhythmia event.

In some embodiments, the at least one further communication comprises at least one of a recommendation to retest one or more of the at least one annotator, a recommendation to increase the respective skill score of one or more of the at least one annotator, a recommendation to decrease the respective skill score of one or more of the at least one annotator, or any combination thereof.

In some embodiments, the remote computer system is further configured to retrain the arrhythmia classifier based on the at least one further atypical ECG signal portion, the further annotation data, and the weight data.

In some embodiments, the remote computer system is configured to receive at least one updated skill score comprising a respective updated skill score for each of at least one annotator of the plurality of annotators, determine a respective updated weight for each of the at least one annotator based on the at least one updated skill score, and retrain the arrhythmia classifier based on the respective updated weight for each of the at least one annotator.

In some embodiments, training the arrhythmia classifier includes adjusting a hyperparameter of a loss function of the arrhythmia classifier based on the weight data.

In some embodiments, training the arrhythmia classifier comprises adjusting the respective weight for each of at least one annotator of the plurality of annotators based on a hyperparameter tuning process.

In some embodiments, the respective skill score for each respective annotator of the plurality of annotators comprises an initial skill score, the respective weight for each respective annotator comprises an initial weight, the historical collection of the plurality of atypical ECG signal portions with the annotation data comprises a training subset of the plurality of atypical ECG signal portions and a validation subset of the plurality of atypical ECG signal portions, and the respective weight for each of the at least one annotator comprises a hyperparameter and an initial value of the hyperparameter comprises the initial weight. In some embodiments, the hyperparameter tuning process includes training the arrhythmia classifier based on the training subset and the initial value of the hyperparameter, determining a metric associated with the initial value of the hyperparameter based on the validation subset, adjusting a value of the hyperparameter to provide an adjusted value of the hyperparameter, retraining the arrhythmia classifier based on the training subset and the adjusted value of the hyperparameter, and determining the metric associated with the adjusted value of the hyperparameter based on the validation set.

In some embodiments, the hyperparameter tuning process further comprises repeating adjusting of the value of the hyperparameter, retraining of the arrhythmia classifier, and determining of the metric associated with the adjusted value of the hyperparameter until a termination condition is satisfied.

In some embodiments, repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of a value of the hyperparameter that optimizes the metric is found, a maximum number of iterations is reached, or any combination thereof.

In some embodiments, the metric comprises at least one of accuracy, loss, area under curve (AUC), precision, recall, F1 score, or any combination thereof.

In some embodiments, adjusting the value of the hyperparameter comprises at least one of adjusting the value of the hyperparameter within a search space, adjusting the value of the hyperparameter within a range around the initial value, adjusting the value of the hyperparameter within a range around the initial skill score, adjusting the value of the hyperparameter randomly, or any combination thereof.

In some embodiments, the external wearable heart monitoring device comprises a patch configured to be worn by the patient for an extended period of time, the patch comprising the plurality of ECG electrodes.

In some embodiments, the patch is configured to be adhesively coupled to skin of the patient.

In some embodiments, the adhesive patch is disposable.

In some embodiments, the adhesive patch is configured to be continuously adhesively coupled to the skin of the patient for at least one of: 3-5 days, 5-7 days, 7-10 days, 10-14 days, or 14-30 days.

In some embodiments, the external wearable heart monitoring device further comprises a cardiac monitoring unit configured to be removably attached to the patch.

In some embodiments, the cardiac monitoring unit is configured to record the surface ECG activity of the patient sensed by the plurality of ECG electrodes and associated circuitry.

Embodiments of the current disclosure include an atypical ECG lead arrhythmia classification system. In some embodiments, the system may include a non-transitory computer-readable medium comprising an arrhythmia classifier comprising at least one neural network and at least one processor operatively connected to the non-transitory computer-readable medium. In some embodiments, the at least one processor is configured to receive a plurality of scores comprising a respective score for each respective annotator of a plurality of annotators, determine a respective initial weight for each respective annotator of the plurality of annotators based on the plurality of scores, receive a historical collection of a plurality of atypical electrocardiogram (ECG) signal portions with annotation data, the annotation data comprising at least one respective annotation for each respective atypical ECG signal portion of the plurality of atypical ECG signal portions, train the arrhythmia classifier based on the historical collection of the plurality of atypical ECG signal portions with the annotation data and based on weight data for the annotation data of the plurality of atypical ECG signal portions, the weight data comprising the respective initial weight for the respective annotator of each respective annotation, receive at least one further atypical ECG signal portion with further annotation data from at least one annotator of the plurality of annotators, analyze the at least one further atypical ECG signal portion to detect at least one arrhythmia event based on the arrhythmia classifier, compare the further annotation data to the at least one arrhythmia event, and transmit at least one communication based on comparing the further annotation data to the at least one arrhythmia event.

In some embodiments, the plurality of atypical ECG signal portions were obtained from an external wearable heart monitoring device configured for continuous and long-term monitoring of a patient comprising a plurality of ECG electrodes and associated circuitry configured to sense surface ECG activity of the patient, each ECG electrode configured to be anatomically located within a circumferential atypical zone of the patient's torso in an uninhibiting manner so as to allow for the patient to be ambulatory, wherein the plurality of ECG electrodes and associated circuitry are configured to provide at least one atypical ECG channel producing at least one atypical ECG signal for the patient.

In some embodiments, the plurality of ECG electrodes comprises at least four ECG electrodes.

In some embodiments, the at least one atypical ECG channel comprises at least two atypical ECG channels, each atypical ECG channel associated with two respective ECG electrodes of the at least four ECG electrodes.

In some embodiments, the at least four ECG electrodes comprise a front ECG electrode, a back ECG electrode, a first side ECG electrode, and a second side ECG electrode, wherein the at least two atypical ECG channels comprise a front-to-back (FB) ECG channel associated with the front ECG electrode and the back ECG electrode, and wherein the at least two typical ECG channels further comprise a side-to-side (SS) ECG channel associated with the first side ECG electrode and the second side ECG electrode.

In some embodiments, the at least two atypical ECG channels comprise a first atypical ECG channel and a second atypical ECG channel substantially orthogonal to the first atypical ECG channel.

In some embodiments, the at least one atypical ECG channel comprises at least three atypical ECG channels.

In some embodiments, the at least one atypical ECG channel comprises at least four atypical ECG channels.

In some embodiments, the at least one atypical ECG channel comprises a front-to-back (FB) ECG channel.

In some embodiments, the at least one atypical ECG channel comprises a side-to-side (SS) ECG channel.

In some embodiments, the at least one atypical ECG channel comprises at least one dynamically defined atypical ECG channel.

In some embodiments, the associated circuitry is configured to analyze surface ECG activity of the patient and select at least two of the plurality of ECG electrodes to define the at least one dynamically defined atypical ECG channel.

In some embodiments, the plurality of atypical ECG signal portions were obtained from an external wearable heart monitoring device configured for continuous and long-term monitoring of a patient comprising a plurality of ECG electrodes and associated circuitry configured to sense surface ECG activity of the patient, each ECG electrode configured to be anatomically located on the patient's thorax superior to the patient's xiphoid process and lateral to the patient's sternum, in an uninhibiting manner so as to allow for the patient to be ambulatory, wherein the plurality of ECG electrodes and associated circuitry are configured to provide at least one atypical ECG channel producing at least one atypical ECG signal for the patient.

In some embodiments, at least two ECG electrodes of the plurality of ECG electrodes are disposed within a predetermined distance on the patient's thorax superior to the patient's xiphoid process and lateral to the patient's sternum.

In some embodiments, the predetermined distance comprises 15 centimeters, and wherein the at least two ECG electrodes are spaced less than 15 centimeters.

In some embodiments, the at least two ECG electrodes are spaced less than 10 centimeters.

In some embodiments, the at least two ECG electrodes are spaced 5-15 centimeters.

In some embodiments, the at least two ECG electrodes are spaced less than 5 centimeters.

In some embodiments, the external wearable heart monitoring device comprises a single adhesive patch.

In some embodiments, the plurality of ECG electrodes are all on one side of the patient's sternum.

In some embodiments, the plurality of ECG electrodes are left lateral to the patient's sternum.

In some embodiments, the plurality of ECG electrodes are right lateral to the patient's sternum.

In some embodiments, the respective score for each respective annotator is based on a respective skill level of the respective annotator.

In some embodiments, the respective score for each respective annotator comprises a skill score.

In some embodiments, the skill score comprises an integer value from one to four.

In some embodiments, the skill score comprises an integer value from one to five.

In some embodiments, the skill score comprises an integer value from one to ten.

In some embodiments, the skill score comprises an integer value from one to 100.

In some embodiments, the skill score comprises one of 25, 50, 75, or 100.

In some embodiments, the skill score comprises a value from zero to one.

In some embodiments, the at least one processor is further configured to: determine an updated weight for each respective annotator of the at least one annotator based on comparing the further annotation data to the at least one arrhythmia event.

In some embodiments, the at least one processor is further configured to retrain the arrhythmia classifier based on the at least one further atypical ECG signal portion, the further annotation data, and the updated weight data.

In some embodiments, the at least one communication comprises at least one of a recommendation to retest one or more of the at least one annotator, a recommendation to increase the respective skill score of one or more of the at least one annotator, a recommendation to decrease the respective skill score of one or more of the at least one annotator, or any combination thereof.

In some embodiments, the at least one processor is further configured to retrain the arrhythmia classifier based on the at least one further atypical ECG signal portion, the further annotation data, and the initial weight data.

In some embodiments, the at least one processor is configured to receive at least one updated skill score comprising a respective updated skill score for each of at least one annotator of the plurality of annotators, determine a respective updated weight for each of the at least one annotator based on the at least one updated skill score, and retrain the arrhythmia classifier based on the respective updated weight for each of the at least one annotator.

In some embodiments, training the arrhythmia classifier comprises adjusting a hyperparameter of a loss function of the arrhythmia classifier based on the weight data.

In some embodiments, training the arrhythmia classifier comprises adjusting the respective weight for each of at least one annotator of the plurality of annotators based on a hyperparameter tuning process.

In some embodiments, the respective skill score for each respective annotator of the plurality of annotators comprises an initial skill score, the respective weight for each respective annotator comprises an initial weight, the historical collection of the plurality of atypical ECG signal portions with the annotation data comprises a training subset of the plurality of atypical ECG signal portions and a validation subset of the plurality of atypical ECG signal portions, and the respective weight for each of the at least one annotator comprises a hyperparameter and an initial value of the hyperparameter comprises the initial weight. In some embodiments, the hyperparameter tuning process comprises training the arrhythmia classifier based on the training subset and the initial value of the hyperparameter, determining a metric associated with the initial value of the hyperparameter based on the validation subset, adjusting a value of the hyperparameter to provide an adjusted value of the hyperparameter, retraining the arrhythmia classifier based on the training subset and the adjusted value of the hyperparameter, and determining the metric associated with the adjusted value of the hyperparameter based on the validation set.

In some embodiments, the hyperparameter tuning process further comprises repeating adjusting of the value of the hyperparameter, retraining of the arrhythmia classifier, and determining of the metric associated with the adjusted value of the hyperparameter until a termination condition is satisfied.

In some embodiments, repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of a value of the hyperparameter that optimizes the metric is found, a maximum number of iterations is reached, or any combination thereof.

In some embodiments, the metric comprises at least one of accuracy, loss, area under curve (AUC), precision, recall, F1 score, or any combination thereof.

In some embodiments, adjusting the value of the hyperparameter comprises at least one of adjusting the value of the hyperparameter within a search space, adjusting the value of the hyperparameter within a range around the initial value, adjusting the value of the hyperparameter within a range around the initial skill score, adjusting the value of the hyperparameter randomly, or any combination thereof.

Embodiments of the current disclosure include a wearable atypical electrocardiogram (ECG) lead atrial fibrillation monitoring system for identifying atrial fibrillation experienced by a patient. In some embodiments, the system may include an external wearable heart monitoring device configured for continuous and long-term monitoring of a patient comprising a plurality of ECG electrodes and associated circuitry configured to sense surface ECG activity of the patient, each ECG electrode configured to be anatomically located within a circumferential atypical zone of the patient's torso in an uninhibiting manner so as to allow for the patient to be ambulatory, wherein the plurality of ECG electrodes and associated circuitry are configured to provide at least one atypical ECG channel producing at least one atypical ECG signal for the patient. In some embodiments, the system may include a non-transitory computer-readable medium comprising an atrial fibrillation classifier comprising at least one neural network, wherein the neural network is trained based on a historical collection of a plurality of atypical ECG signal portions with annotation data, the annotation data comprising at least one respective annotation for each respective ECG signal portion of the plurality of ECG signal portions, and wherein the neural network is further trained based on weight data for the annotation data of the atypical ECG signal portions, the weight data comprising a respective weight for each respective annotation based on a respective annotator of the respective annotation. In some embodiments, the system may include at least one processor operatively connected to the at least one atypical ECG channel and the non-transitory computer-readable medium. The at least one processor may be configured to receive the at least one atypical ECG signal of the at least one atypical ECG channel, monitor the at least one atypical ECG signal to detect at least one atrial fibrillation event based on the atrial fibrillation classifier, and transmit at least one communication based on the at least one atrial fibrillation event to a remote computer system.

In some embodiments, the plurality of ECG electrodes comprises at least four ECG electrodes.

In some embodiments, the at least one atypical ECG channel comprises at least two atypical ECG channels, each atypical ECG channel associated with two respective ECG electrodes of the at least four ECG electrodes.

In some embodiments, the at least four ECG electrodes comprise a front ECG electrode, a back ECG electrode, a first side ECG electrode, and a second side ECG electrode, wherein the at least two atypical ECG channels comprise a front-to-back (FB) ECG channel associated with the front ECG electrode and the back ECG electrode, and wherein the at least two typical ECG channels further comprise a side-to-side (SS) ECG channel associated with the first side ECG electrode and the second side ECG electrode.

In some embodiments, the at least two atypical ECG channels comprise a first atypical ECG channel and a second atypical ECG channel substantially orthogonal to the first atypical ECG channel.

In some embodiments, the at least one atypical ECG channel comprises at least three atypical ECG channels.

In some embodiments, the at least one atypical ECG channel comprises at least four atypical ECG channels.

In some embodiments, the at least one atypical ECG channel comprises a front-to-back (FB) ECG channel.

In some embodiments, the at least one atypical ECG channel comprises a side-to-side (SS) ECG channel.

In some embodiments, the at least one atypical ECG channel comprises at least one dynamically defined atypical ECG channel.

In some embodiments, the associated circuitry is configured to analyze surface ECG activity of the patient and select at least two of the plurality of ECG electrodes to define the at least one dynamically defined atypical ECG channel.

In some embodiments, the respective weight for each respective annotator is based on a respective skill level of the respective annotator.

In some embodiments, the respective skill level for each respective annotator comprises a skill score.

In some embodiments, the skill score comprises an integer value from one to four.

In some embodiments, the skill score comprises an integer value from one to five.

In some embodiments, the skill score comprises an integer value from one to ten.

In some embodiments, the skill score comprises an integer value from one to 100.

In some embodiments, the skill score comprises one of 25, 50, 75, or 100.

In some embodiments, the skill score comprises a value from zero to one.

In some embodiments, the remote computer system is configured to receive a plurality of skill scores comprising a respective skill score for each respective annotator, wherein a plurality of annotators comprises each respective annotator and determine the respective weight for each respective annotator based on the plurality of scores.

In some embodiments, the remote computer system is further configured to receive the historical collection of the plurality of atypical ECG signal portions with the annotation data and train the atrial fibrillation classifier based on the historical collection of the plurality of atypical ECG signal portions with the annotation data and based on the weight data.

In some embodiments, the at least one communication comprises at least one further atypical ECG signal portion associated with the at least one atrial fibrillation event. In some embodiments, the remote computer system is further configured to receive the at least one communication comprising the at least one further atypical ECG signal portion and receive further annotation data associated with the at least one further atypical ECG signal portion from at least one annotator of the plurality of annotators.

In some embodiments, the remote computer system is further configured to compare the further annotation data to the at least one atrial fibrillation event detected based on the atrial fibrillation classifier and determine an updated weight for each respective annotator of the at least one annotator based on comparing the further annotation data to the at least one atrial fibrillation event.

In some embodiments, the remote computer system is further configured to retrain the atrial fibrillation classifier based on the at least one further atypical ECG signal portion, the further annotation data, and the updated weight data.

In some embodiments, the remote computer system is further configured to compare the further annotation data to the at least one atrial fibrillation event detected based on the atrial fibrillation classifier and transmit at least one further communication based on comparing the further annotation data to the at least one atrial fibrillation event.

In some embodiments, the at least one further communication comprises at least one of a recommendation to retest one or more of the at least one annotator, a recommendation to increase the respective skill score of one or more of the at least one annotator, a recommendation to decrease the respective skill score of one or more of the at least one annotator, or any combination thereof.

In some embodiments, the remote computer system is further configured to retrain the atrial fibrillation classifier based on the at least one further atypical ECG signal portion, the further annotation data, and the weight data.

In some embodiments, the remote computer system is configured to receive at least one updated skill score comprising a respective updated skill score for each of at least one annotator of the plurality of annotators, determine a respective updated weight for each of the at least one annotator based on the at least one updated skill score, and retrain the atrial fibrillation classifier based on the respective updated weight for each of the at least one annotator.

In some embodiments, training the atrial fibrillation classifier comprises adjusting a hyperparameter of a loss function of the atrial fibrillation classifier based on the weight data.

In some embodiments, training the atrial fibrillation classifier comprises adjusting the respective weight for each of at least one annotator of the plurality of annotators based on a hyperparameter tuning process.

In some embodiments, the respective skill score for each respective annotator of the plurality of annotators comprises an initial skill score, the respective weight for each respective annotator comprises an initial weight, the historical collection of the plurality of atypical ECG signal portions with the annotation data comprises a training subset of the plurality of atypical ECG signal portions and a validation subset of the plurality of atypical ECG signal portions, and the respective weight for each of the at least one annotator comprises a hyperparameter and an initial value of the hyperparameter comprises the initial weight. In some embodiments, the hyperparameter tuning process comprises training the atrial fibrillation classifier based on the training subset and the initial value of the hyperparameter, determining a metric associated with the initial value of the hyperparameter based on the validation subset, adjusting a value of the hyperparameter to provide an adjusted value of the hyperparameter, retraining the atrial fibrillation classifier based on the training subset and the adjusted value of the hyperparameter, and determining the metric associated with the adjusted value of the hyperparameter based on the validation set.

In some embodiments, the hyperparameter tuning process further comprises repeating adjusting of the value of the hyperparameter, retraining of the atrial fibrillation classifier, and determining of the metric associated with the adjusted value of the hyperparameter until a termination condition is satisfied.

In some embodiments, repeating adjusting of the value of the hyperparameter, retraining of the atrial fibrillation classifier, and determining of the metric associated with the adjusted value of the hyperparameter until the termination condition is satisfied comprises repeating adjusting of the value of the hyperparameter, retraining of the atrial fibrillation classifier, and determining of the metric associated with the adjusted value of the hyperparameter until at least one of a value of the hyperparameter that optimizes the metric is found, a maximum number of iterations is reached, or any combination thereof.

In some embodiments, the metric comprises at least one of accuracy, loss, area under curve (AUC), precision, recall, F1 score, or any combination thereof.

In some embodiments, adjusting the value of the hyperparameter comprises at least one of adjusting the value of the hyperparameter within a search space, adjusting the value of the hyperparameter within a range around the initial value, adjusting the value of the hyperparameter within a range around the initial skill score, adjusting the value of the hyperparameter randomly, or any combination thereof.

In some embodiments, the external wearable heart monitoring device comprises a garment configured to be worn about a torso of the patient for an extended period of time and further configured to house the plurality of ECG electrodes.

In some embodiments, the garment comprises a plurality of receptacles configured to receive the plurality of ECG electrodes.

In some embodiments, the external wearable heart monitoring device comprises a plurality therapy electrodes configured to be housed in the garment.

In some embodiments, the external wearable heart monitoring device is configured to determine whether the patient is experiencing a treatable cardiac atrial fibrillation and deliver one or more therapeutic shocks to the patient via the plurality of therapy electrodes upon determining that the patient is experiencing a treatable cardiac atrial fibrillation.

Embodiments of the current disclosure include a wearable atypical electrocardiogram (ECG) lead atrial fibrillation monitoring system for identifying atrial fibrillation experienced by a patient. In some embodiments, the system may include an external wearable heart monitoring device configured for continuous and long-term monitoring of a patient comprising a plurality of ECG electrodes and associated circuitry configured to sense surface ECG activity of the patient, each ECG electrode configured to be anatomically located on the patient's thorax superior to the patient's xiphoid process and lateral to the patient's sternum, in an uninhibiting manner so as to allow for the patient to be ambulatory, wherein the plurality of ECG electrodes and associated circuitry are configured to provide at least one atypical ECG channel producing at least one atypical ECG signal for the patient. In some embodiments, the system may include a non-transitory computer-readable medium comprising an atrial fibrillation classifier comprising at least one neural network, wherein the neural network is trained based on a historical collection of a plurality of atypical ECG signal portions with annotation data, the annotation data comprising at least one respective annotation for each respective ECG signal portion of the plurality of ECG signal portions, and wherein the neural network is further trained based on weight data for the annotation data of the ECG signal portions, the weight data comprising a respective weight for each respective annotation based on a respective annotator of the respective annotation. In some embodiments, the system may include at least one processor operatively connected to the at least one atypical ECG channel and the non-transitory computer-readable medium. The at least one processor may be configured to receive the at least one atypical ECG signal of the at least one atypical ECG channel, monitor the at least one atypical ECG signal to detect at least one atrial fibrillation event based on the atrial fibrillation classifier, and transmit at least one communication based on the at least one atrial fibrillation event to a remote computer system.

In some embodiments, at least two ECG electrodes of the plurality of ECG electrodes are disposed within a predetermined distance on the patient's thorax superior to the patient's xiphoid process and lateral to the patient's sternum.

In some embodiments, the predetermined distance comprises 15 centimeters, and wherein the at least two ECG electrodes are spaced less than 15 centimeters.

In some embodiments, the at least two ECG electrodes are spaced less than 10 centimeters.

In some embodiments, the at least two ECG electrodes are spaced 5-15 centimeters.

In some embodiments, the at least two ECG electrodes are spaced less than 5 centimeters.

In some embodiments, the external wearable heart monitoring device comprises a single adhesive patch.

In some embodiments, the plurality of ECG electrodes are all on one side of the patient's sternum.

In some embodiments, the plurality of ECG electrodes are left lateral to the patient's sternum.

In some embodiments, the plurality of ECG electrodes are right lateral to the patient's sternum.

In some embodiments, the respective weight for each respective annotator is based on a respective skill level of the respective annotator.

In some embodiments, the respective skill level for each respective annotator comprises a skill score.

In some embodiments, the skill score comprises an integer value from one to four.

In some embodiments, the skill score comprises an integer value from one to five.

In some embodiments, the skill score comprises an integer value from one to ten.

In some embodiments, the skill score comprises an integer value from one to 100.

In some embodiments, the skill score comprises one of 25, 50, 75, or 100.

In some embodiments, the skill score comprises a value from zero to one.

In some embodiments, the remote computer system is configured to receive a plurality of skill scores comprising a respective skill score for each respective annotator, wherein a plurality of annotators comprises each respective annotator and determine the respective weight for each respective annotator based on the plurality of scores.

In some embodiments, the remote computer system is configured to receive the historical collection of the plurality of atypical ECG signal portions with the annotation data and train the atrial fibrillation classifier based on the historical collection of the plurality of atypical ECG signal portions with the annotation data and based on the weight data.

In some embodiments, the at least one communication comprises at least one further atypical ECG signal portion associated with the at least one atrial fibrillation event. In some embodiments, the remote computer system is further configured to receive the at least one communication comprising the at least one further atypical ECG signal portion and receive further annotation data associated with the at least one further atypical ECG signal portion from at least one annotator of the plurality of annotators.

In some embodiments, the remote computer system is further configured to compare the further annotation data to the at least one atrial fibrillation event detected based on the atrial fibrillation classifier and determine an updated weight for each respective annotator of the at least one annotator based on comparing the further annotation data to the at least one atrial fibrillation event.

In some embodiments, the remote computer system is further configured to retrain the atrial fibrillation classifier based on the at least one further atypical ECG signal portion, the further annotation data, and the updated weight data.

In some embodiments, the remote computer system is further configured to compare the further annotation data to the at least one atrial fibrillation event detected based on the atrial fibrillation classifier and transmit at least one further communication based on comparing the further annotation data to the at least one atrial fibrillation event.

In some embodiments, the at least one further communication comprises at least one of a recommendation to retest one or more of the at least one annotator, a recommendation to increase the respective skill score of one or more of the at least one annotator, a recommendation to decrease the respective skill score of one or more of the at least one annotator, or any combination thereof.

In some embodiments, the remote computer system is further configured to retrain the atrial fibrillation classifier based on the at least one further atypical ECG signal portion, the further annotation data, and the weight data.

In some embodiments, the remote computer system is configured to receive at least one updated skill score comprising a respective updated skill score for each of at least one annotator of the plurality of annotators, determine a respective updated weight for each of the at least one annotator based on the at least one updated skill score, and retrain the atrial fibrillation classifier based on the respective updated weight for each of the at least one annotator.

In some embodiments, training the atrial fibrillation classifier comprises adjusting a hyperparameter of a loss function of the atrial fibrillation classifier based on the weight data.

In some embodiments, training the atrial fibrillation classifier comprises adjusting the respective weight for each of at least one annotator of the plurality of annotators based on a hyperparameter tuning process.

In some embodiments, the respective skill score for each respective annotator of the plurality of annotators comprises an initial skill score, the respective weight for each respective annotator comprises an initial weight, the historical collection of the plurality of atypical ECG signal portions with the annotation data comprises a training subset of the plurality of atypical ECG signal portions and a validation subset of the plurality of atypical ECG signal portions, and the respective weight for each of the at least one annotator comprises a hyperparameter and an initial value of the hyperparameter comprises the initial weight. In some embodiments, the hyperparameter tuning process comprises training the atrial fibrillation classifier based on the training subset and the initial value of the hyperparameter, determining a metric associated with the initial value of the hyperparameter based on the validation subset, adjusting a value of the hyperparameter to provide an adjusted value of the hyperparameter, retraining the atrial fibrillation classifier based on the training subset and the adjusted value of the hyperparameter, and determining the metric associated with the adjusted value of the hyperparameter based on the validation set.

In some embodiments, the hyperparameter tuning process further comprises repeating adjusting of the value of the hyperparameter, retraining of the atrial fibrillation classifier, and determining of the metric associated with the adjusted value of the hyperparameter until a termination condition is satisfied.

In some embodiments, repeating adjusting of the value of the hyperparameter, retraining of the atrial fibrillation classifier, and determining of the metric associated with the adjusted value of the hyperparameter until the termination condition is satisfied comprises repeating adjusting of the value of the hyperparameter, retraining of the atrial fibrillation classifier, and determining of the metric associated with the adjusted value of the hyperparameter until at least one of a value of the hyperparameter that optimizes the metric is found, a maximum number of iterations is reached, or any combination thereof.

In some embodiments, the metric comprises at least one of accuracy, loss, area under curve (AUC), precision, recall, F1 score, or any combination thereof.

In some embodiments, adjusting the value of the hyperparameter comprises at least one of adjusting the value of the hyperparameter within a search space, adjusting the value of the hyperparameter within a range around the initial value, adjusting the value of the hyperparameter within a range around the initial skill score, adjusting the value of the hyperparameter randomly, or any combination thereof.

In some embodiments, the external wearable heart monitoring device comprises a patch configured to be worn by the patient for an extended period of time, the patch comprising the plurality of ECG electrodes.

In some embodiments, the patch is configured to be adhesively coupled to skin of the patient.

In some embodiments, the adhesive patch is disposable.

In some embodiments, the adhesive patch is configured to be continuously adhesively coupled to the skin of the patient for at least one of: 3-5 days, 5-7 days, 7-10 days, 10-14 days, or 14-30 days.

In some embodiments, the external wearable heart monitoring device further comprises a cardiac monitoring unit configured to be removably attached to the patch.

In some embodiments, the cardiac monitoring unit is configured to record the surface ECG activity of the patient sensed by the plurality of ECG electrodes and associated circuitry.

Embodiments of the current disclosure include a wearable electrocardiogram (ECG) lead arrhythmia monitoring system for identifying arrhythmias experienced by a patient. In some embodiments, the system may include an external wearable heart monitoring device configured for continuous and long-term monitoring of a patient comprising a plurality of ECG electrodes and associated circuitry configured to sense surface ECG activity of the patient, wherein the plurality of ECG electrodes and associated circuitry are configured to provide at least one ECG channel producing at least one ECG signal for the patient. In some embodiments, the system may include a non-transitory computer-readable medium comprising an arrhythmia classifier comprising at least one neural network, wherein the neural network is trained based on a historical collection of a plurality of ECG signal portions with annotation data, the annotation data comprising at least one respective annotation for each respective ECG signal portion of the plurality of ECG signal portions, and wherein the neural network is further trained based on weight data for the annotation data of the plurality of ECG signal portions, the weight data comprising a respective weight for each respective annotation based on a respective annotator of the respective annotation. In some embodiments, the system may include at least one processor operatively connected to the at least one ECG channel and the non-transitory computer-readable medium. The at least one processor may be configured to receive the at least one ECG signal of the at least one ECG channel, monitor the at least one ECG signal to detect at least one arrhythmia event based on the arrhythmia classifier, and transmit at least one communication based on the at least one arrhythmia event to a remote computer system.

In some embodiments, the plurality of ECG electrodes comprises at least three ECG electrodes.

In some embodiments, the at least three ECG electrodes comprise a right arm (RA) EGG electrode, a left arm (LA) ECG electrode, and a left leg (LL) ECG electrode.

In some embodiments, the at least one ECG channel comprises a lead I channel between the RA ECG electrode and the LA ECG electrode, a lead II channel between the RCA ECG electrode and the LL ECG electrode, and a lead III channel between the LA ECG electrode and the LL ECG electrode.

In some embodiments, the plurality of ECG electrodes comprises at least five ECG electrodes.

In some embodiments, the at least five ECG electrodes comprise a right arm (RA) EGG electrode, a right leg (RL) ECG electrode, a left arm (LA) ECG electrode, a left leg (LL) ECG electrode, and a chest ECG electrode.

In some embodiments, the at least one ECG channel comprises a lead I channel, a lead II channel, a lead III channel, and at least one unipolar lead channel.

In some embodiments, the plurality of ECG electrodes comprises at least 10 ECG electrodes.

In some embodiments, the at least 10 ECG electrodes comprise a right arm (RA) EGG electrode, a right leg (RL) ECG electrode, a left arm (LA) ECG electrode, a left leg (LL) ECG electrode, and six precordial ECG electrodes.

In some embodiments, the at least one ECG channel comprises at least six limb ECG channels and at least six precordial ECG channels.

In some embodiments, the at least six limb ECG channels comprise a lead I channel, a lead II channel, a lead III channel, an augmented vector right (aVR) channel, an augmented vector left (aVL) channel, and an augmented vector foot (aVF) channel. In some embodiments, the at least six precordial ECG channels comprise a V1 channel, a V2 channel, a V3 channel, a V4 channel, a V5 channel, and a V6 channel.

In some embodiments, the respective weight for each respective annotator is based on a respective skill level of the respective annotator.

In some embodiments, the respective skill level for each respective annotator comprises a skill score.

In some embodiments, the skill score comprises one of: an integer value from one to four; an integer value from one to five; an integer value from one to ten; an integer value from one to 100; one of 25, 50, 75, or 100; or a value from zero to one.

In some embodiments, the remote computer system is configured to receive a plurality of skill scores comprising a respective skill score for each respective annotator, wherein a plurality of annotators comprises each respective annotator and determine the respective weight for each respective annotator based on the plurality of skill scores.

In some embodiments, the remote computer system is further configured to receive the historical collection of the plurality of ECG signal portions with the annotation data and train the arrhythmia classifier based on the historical collection of the plurality of ECG signal portions with the annotation data and based on the weight data.

In some embodiments, the at least one communication comprises at least one further ECG signal portion associated with the at least one arrhythmia event. In some embodiments, the remote computer system is further configured to receive the at least one communication comprising the at least one further ECG signal portion and receive further annotation data associated with the at least one further ECG signal portion from at least one annotator of the plurality of annotators.

In some embodiments, the remote computer system is further configured to compare the further annotation data to the at least one arrhythmia event detected based on the arrhythmia classifier, and determine an updated weight for each respective annotator of the at least one annotator based on comparing the further annotation data to the at least one arrhythmia event.

In some embodiments, the remote computer system is further configured to retrain the arrhythmia classifier based on the at least one further ECG signal portion, the further annotation data, and the updated weight data.

In some embodiments, the remote computer system is further configured to compare the further annotation data to the at least one arrhythmia event detected based on the arrhythmia classifier and transmit at least one further communication based on comparing the further annotation data to the at least one arrhythmia event.

In some embodiments, the at least one further communication comprises at least one of a recommendation to retest one or more of the at least one annotator, a recommendation to increase the respective skill score of one or more of the at least one annotator, a recommendation to decrease the respective skill score of one or more of the at least one annotator, or any combination thereof.

In some embodiments, the remote computer system is further configured to retrain the arrhythmia classifier based on the at least one further ECG signal portion, the further annotation data, and the weight data.

In some embodiments, the remote computer system is configured to receive at least one updated skill score comprising a respective updated skill score for each of at least one annotator of the plurality of annotators, determine a respective updated weight for each of the at least one annotator based on the at least one updated skill score, and retrain the arrhythmia classifier based on the respective updated weight for each of the at least one annotator.

In some embodiments, training the arrhythmia classifier comprises adjusting a hyperparameter of a loss function of the arrhythmia classifier based on the weight data.

In some embodiments, training the arrhythmia classifier comprises adjusting the respective weight for each of at least one annotator of the plurality of annotators based on a hyperparameter tuning process.

In some embodiments, the respective skill score for each respective annotator of the plurality of annotators comprises an initial skill score, the respective weight for each respective annotator comprises an initial weight, the historical collection of the plurality of ECG signal portions with the annotation data comprises a training subset of the plurality of ECG signal portions and a validation subset of the plurality of ECG signal portions, and the respective weight for each of the at least one annotator comprises a hyperparameter and an initial value of the hyperparameter comprises the initial weight. In some embodiments, the hyperparameter tuning process comprises training the arrhythmia classifier based on the training subset and the initial value of the hyperparameter, determining a metric associated with the initial value of the hyperparameter based on the validation subset, adjusting a value of the hyperparameter to provide an adjusted value of the hyperparameter, retraining the arrhythmia classifier based on the training subset and the adjusted value of the hyperparameter, and determining the metric associated with the adjusted value of the hyperparameter based on the validation set.

In some embodiments, the hyperparameter tuning process further comprises repeating adjusting of the value of the hyperparameter, retraining of the arrhythmia classifier, and determining of the metric associated with the adjusted value of the hyperparameter until a termination condition is satisfied.

In some embodiments, repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of a value of the hyperparameter that optimizes the metric is found, a maximum number of iterations is reached, or any combination thereof.

In some embodiments, the metric comprises at least one of accuracy, loss, area under curve (AUC), precision, recall, F1 score, or any combination thereof.

In some embodiments, adjusting the value of the hyperparameter comprises at least one of adjusting the value of the hyperparameter within a search space, adjusting the value of the hyperparameter within a range around the initial value, adjusting the value of the hyperparameter within a range around the initial skill score, adjusting the value of the hyperparameter randomly, or any combination thereof.

In some embodiments, the plurality of ECG electrodes and associated circuitry are configured to provide at least one standard ECG channel producing at least one standard ECG signal for the patient.

In some embodiments, the plurality of ECG electrodes and associated circuitry are configured to provide at least one standard ECG channel producing at least one standard ECG signal for the patient and at least one atypical ECG channel producing at least one atypical ECG signal for the patient.

In some embodiments, the plurality of ECG electrodes and associated circuitry are configured to provide at least one of at least one standard ECG channel producing at least one standard ECG signal for the patient or at least one atypical ECG channel producing at least one atypical ECG signal for the patient.

Other non-limiting embodiments will be set forth in the following numbered clauses:

Clause 1: A wearable atypical electrocardiogram (ECG) lead arrhythmia monitoring system for identifying arrhythmias experienced by a patient, comprising: an external wearable heart monitoring device configured for continuous and long-term monitoring of a patient comprising: a plurality of ECG electrodes and associated circuitry configured to sense surface ECG activity of the patient, each ECG electrode configured to be anatomically located within a circumferential atypical zone of the patient's torso in an uninhibiting manner so as to allow for the patient to be ambulatory, wherein the plurality of ECG electrodes and associated circuitry are configured to provide at least one atypical ECG channel producing at least one atypical ECG signal for the patient; and a non-transitory computer-readable medium comprising an arrhythmia classifier comprising at least one neural network, wherein the neural network is trained based on a historical collection of a plurality of atypical ECG signal portions with annotation data, the annotation data comprising at least one respective annotation for each respective atypical ECG signal portion of the plurality of atypical ECG signal portions, and wherein the neural network is further trained based on weight data for the annotation data of the plurality of atypical ECG signal portions, the weight data comprising a respective weight for each respective annotation based on a respective annotator of the respective annotation; and at least one processor operatively connected to the at least one atypical ECG channel and the non-transitory computer-readable medium, the at least one processor configured to: receive the at least one atypical ECG signal of the at least one atypical ECG channel; monitor the at least one atypical ECG signal to detect at least one arrhythmia event based on the arrhythmia classifier; and transmit at least one communication based on the at least one arrhythmia event to a remote computer system.

Clause 2: The system of clause 1, wherein the plurality of ECG electrodes comprises at least four ECG electrodes.

Clause 3: The system of any preceding clause, wherein the at least one atypical ECG channel comprises at least two atypical ECG channels, each atypical ECG channel associated with two respective ECG electrodes of the at least four ECG electrodes.

Clause 4: The system of any preceding clause, wherein the at least four ECG electrodes comprise a front ECG electrode, a back ECG electrode, a first side ECG electrode, and a second side ECG electrode, wherein the at least two atypical ECG channels comprise a front-to-back (FB) ECG channel associated with the front ECG electrode and the back ECG electrode, and wherein the at least two typical ECG channels further comprise a side-to-side (SS) ECG channel associated with the first side ECG electrode and the second side ECG electrode.

Clause 5: The system of any preceding clause, wherein the at least two atypical ECG channels comprise a first atypical ECG channel and a second atypical ECG channel substantially orthogonal to the first atypical ECG channel.

Clause 6: The system of any preceding clause, wherein the at least one atypical ECG channel comprises at least three atypical ECG channels.

Clause 7: The system of any preceding clause, wherein the at least one atypical ECG channel comprises at least four atypical ECG channels.

Clause 8: The system of any preceding clause, wherein the at least one atypical ECG channel comprises a front-to-back (FB) ECG channel.

Clause 9: The system of any preceding clause, wherein the at least one atypical ECG channel comprises a side-to-side (SS) ECG channel.

Clause 10: The system of any preceding clause, wherein the at least one atypical ECG channel comprises at least one dynamically defined atypical ECG channel.

Clause 11: The system of any preceding clause, wherein the associated circuitry is configured to analyze surface ECG activity of the patient and select at least two of the plurality of ECG electrodes to define the at least one dynamically defined atypical ECG channel.

Clause 12: The system of any preceding clause, wherein the respective weight for each respective annotator is based on a respective skill level of the respective annotator.

Clause 13: The system of any preceding clause, wherein the respective skill level for each respective annotator comprises a skill score.

Clause 14: The system of any preceding clause, wherein the skill score comprises an integer value from one to four.

Clause 15: The system of any preceding clause, wherein the skill score comprises an integer value from one to five.

Clause 16: The system of any preceding clause, wherein the skill score comprises an integer value from one to ten.

Clause 17: The system of any preceding clause, wherein the skill score comprises an integer value from one to 100.

Clause 18: The system of any preceding clause, wherein the skill score comprises one of 25, 50, 75, or 100.

Clause 19: The system of any preceding clause, wherein the skill score comprises a value from zero to one.

Clause 20: The system of any preceding clause, wherein the remote computer system is configured to: receive a plurality of skill scores comprising a respective skill score for each respective annotator, wherein a plurality of annotators comprises each respective annotator; and determine the respective weight for each respective annotator based on the plurality of skill scores.

Clause 21: The system of any preceding clause, wherein the remote computer system is further configured to: receive the historical collection of the plurality of atypical ECG signal portions with the annotation data; and train the arrhythmia classifier based on the historical collection of the plurality of atypical ECG signal portions with the annotation data and based on the weight data.

Clause 22: The system of any preceding clause, wherein the at least one communication comprises at least one further atypical ECG signal portion associated with the at least one arrhythmia event; wherein the remote computer system is further configured to: receive the at least one communication comprising the at least one further atypical ECG signal portion; and receive further annotation data associated with the at least one further atypical ECG signal portion from at least one annotator of the plurality of annotators.

Clause 23: The system of any preceding clause, wherein the remote computer system is further configured to: compare the further annotation data to the at least one arrhythmia event detected based on the arrhythmia classifier; and determine an updated weight for each respective annotator of the at least one annotator based on comparing the further annotation data to the at least one arrhythmia event.

Clause 24: The system of any preceding clause, wherein the remote computer system is further configured to: retrain the arrhythmia classifier based on the at least one further atypical ECG signal portion, the further annotation data, and the updated weight data.

Clause 25: The system of any preceding clause, wherein the remote computer system is further configured to: compare the further annotation data to the at least one arrhythmia event detected based on the arrhythmia classifier; and transmit at least one further communication based on comparing the further annotation data to the at least one arrhythmia event.

Clause 26: The system of any preceding clause, wherein the at least one further communication comprises at least one of: a recommendation to retest one or more of the at least one annotator; a recommendation to increase the respective skill score of one or more of the at least one annotator; a recommendation to decrease the respective skill score of one or more of the at least one annotator; or any combination thereof.

Clause 27: The system of any preceding clause, wherein the remote computer system is further configured to: retrain the arrhythmia classifier based on the at least one further atypical ECG signal portion, the further annotation data, and the weight data.

Clause 28: The system of any preceding clause, wherein the remote computer system is configured to: receive at least one updated skill score comprising a respective updated skill score for each of at least one annotator of the plurality of annotators; determine a respective updated weight for each of the at least one annotator based on the at least one updated skill score; and retrain the arrhythmia classifier based on the respective updated weight for each of the at least one annotator.

Clause 29: The system of any preceding clause, wherein training the arrhythmia classifier comprises adjusting a hyperparameter of a loss function of the arrhythmia classifier based on the weight data.

Clause 30: The system of any preceding clause, wherein training the arrhythmia classifier comprises: adjusting the respective weight for each of at least one annotator of the plurality of annotators based on a hyperparameter tuning process.

Clause 31: The system of any preceding clause, wherein the respective skill score for each respective annotator of the plurality of annotators comprises an initial skill score, wherein the respective weight for each respective annotator comprises an initial weight, wherein the historical collection of the plurality of atypical ECG signal portions with the annotation data comprises a training subset of the plurality of atypical ECG signal portions and a validation subset of the plurality of atypical ECG signal portions, wherein the respective weight for each of the at least one annotator comprises a hyperparameter and an initial value of the hyperparameter comprises the initial weight, and wherein the hyperparameter tuning process comprises: training the arrhythmia classifier based on the training subset and the initial value of the hyperparameter; determining a metric associated with the initial value of the hyperparameter based on the validation subset; adjusting a value of the hyperparameter to provide an adjusted value of the hyperparameter; retraining the arrhythmia classifier based on the training subset and the adjusted value of the hyperparameter; and determining the metric associated with the adjusted value of the hyperparameter based on the validation set.

Clause 32: The system of any preceding clause, wherein the hyperparameter tuning process further comprises repeating adjusting of the value of the hyperparameter, retraining of the arrhythmia classifier, and determining of the metric associated with the adjusted value of the hyperparameter until a termination condition is satisfied.

Clause 33: The system of any preceding clause, wherein repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of: a value of the hyperparameter that optimizes the metric is found; a maximum number of iterations is reached; or any combination thereof.

Clause 34: The system of any preceding clause, wherein the metric comprises at least one of accuracy, loss, area under curve (AUC), precision, recall, F1 score, or any combination thereof.

Clause 35: The system of any preceding clause, wherein adjusting the value of the hyperparameter comprises at least one of: adjusting the value of the hyperparameter within a search space; adjusting the value of the hyperparameter within a range around the initial value; adjusting the value of the hyperparameter within a range around the initial skill score; adjusting the value of the hyperparameter randomly; or any combination thereof.

Clause 36: The system of any preceding clause, wherein the external wearable heart monitoring device comprises a garment configured to be worn about a torso of the patient for an extended period of time and further configured to house the plurality of ECG electrodes.

Clause 37: The system of any preceding clause, wherein the garment comprises a plurality of receptacles configured to receive the plurality of ECG electrodes.

Clause 38: The system of any preceding clause, wherein the external wearable heart monitoring device comprises a plurality of therapy electrodes configured to be housed in the garment.

Clause 39: The system of any preceding clause, wherein the external wearable heart monitoring device is configured to determine whether the patient is experiencing a treatable cardiac arrhythmia; and deliver one or more therapeutic shocks to the patient via the plurality of therapy electrodes upon determining that the patient is experiencing a treatable cardiac arrhythmia.

Clause 40: A wearable atypical electrocardiogram (ECG) lead arrhythmia monitoring system for identifying arrhythmias experienced by a patient, comprising: an external wearable heart monitoring device configured for continuous and long-term monitoring of a patient comprising: a plurality of ECG electrodes and associated circuitry configured to sense surface ECG activity of the patient, each ECG electrode configured to be anatomically located on the patient's thorax superior to the patient's xiphoid process and lateral to the patient's sternum, in an uninhibiting manner so as to allow for the patient to be ambulatory, wherein the plurality of ECG electrodes and associated circuitry are configured to provide at least one atypical ECG channel producing at least one atypical ECG signal for the patient; and a non-transitory computer-readable medium comprising an arrhythmia classifier comprising at least one neural network, wherein the neural network is trained based on a historical collection of a plurality of atypical ECG signal portions with annotation data, the annotation data comprising at least one respective annotation for each respective atypical ECG signal portion of the plurality of atypical ECG signal portions, and wherein the neural network is further trained based on weight data for the annotation data of the plurality of atypical ECG signal portions, the weight data comprising a respective weight for each respective annotation based on a respective annotator of the respective annotation; and at least one processor operatively connected to the at least one atypical ECG channel and the non-transitory computer-readable medium, the at least one processor configured to: receive the at least one atypical ECG signal of the at least one atypical ECG channel; monitor the at least one atypical ECG signal to detect at least one arrhythmia event based on the arrhythmia classifier; and transmit at least one communication based on the at least one arrhythmia event to a remote computer system.

Clause 41: The system of clause 40, wherein at least two ECG electrodes of the plurality of ECG electrodes are disposed within a predetermined distance on the patient's thorax superior to the patient's xiphoid process and lateral to the patient's sternum.

Clause 42: The system of clause 40 or clause 41, wherein the predetermined distance comprises 15 centimeters, and wherein the at least two ECG electrodes are spaced less than 15 centimeters.

Clause 43: The system of any of clauses 40-42, wherein the at least two ECG electrodes are spaced less than 10 centimeters.

Clause 44: The system of any of clauses 40-43, wherein the at least two ECG electrodes are spaced 5-15 centimeters.

Clause 45: The system of any of clauses 40-44, wherein the at least two ECG electrodes are spaced less than 5 centimeters.

Clause 46: The system of any of clauses 40-45, wherein the external wearable heart monitoring device comprises a single adhesive patch.

Clause 47: The system of any of clauses 40-46, wherein the plurality of ECG electrodes are all on one side of the patient's sternum.

Clause 48: The system of any of clauses 40-47, wherein the plurality of ECG electrodes are left lateral to the patient's sternum.

Clause 49: The system of any of clauses 40-48, wherein the plurality of ECG electrodes are right lateral to the patient's sternum.

Clause 50: The system of any of clauses 40-49, wherein the respective weight for each respective annotator is based on a respective skill level of the respective annotator.

Clause 51: The system of any of clauses 40-50, wherein the respective skill level for each respective annotator comprises a skill score.

Clause 52: The system of any of clauses 40-51, wherein the skill score comprises an integer value from one to four.

Clause 53: The system of any of clauses 40-52, wherein the skill score comprises an integer value from one to five.

Clause 54: The system of any of clauses 40-53, wherein the skill score comprises an integer value from one to ten.

Clause 55: The system of any of clauses 40-54, wherein the skill score comprises an integer value from one to 100.

Clause 56: The system of any of clauses 40-55, wherein the skill score comprises one of 25, 50, 75, or 100.

Clause 57: The system of any of clauses 40-56, wherein the skill score comprises a value from zero to one.

Clause 58: The system of any of clauses 40-57, wherein the remote computer system is configured to: receive a plurality of skill scores comprising a respective skill score for each respective annotator, wherein a plurality of annotators comprises each respective annotator; and determine the respective weight for each respective annotator based on the plurality of skill scores.

Clause 59: The system of any of clauses 40-58, wherein the remote computer system is configured to: receive the historical collection of the plurality of atypical ECG signal portions with the annotation data; and train the arrhythmia classifier based on the historical collection of the plurality of atypical ECG signal portions with the annotation data and based on the weight data.

Clause 60: The system of any of clauses 40-59, wherein the at least one communication comprises at least one further atypical ECG signal portion associated with the at least one arrhythmia event; wherein the remote computer system is further configured to: receive the at least one communication comprising the at least one further atypical ECG signal portion; and receive further annotation data associated with the at least one further atypical ECG signal portion from at least one annotator of the plurality of annotators.

Clause 61: The system of any of clauses 40-60, wherein the remote computer system is further configured to: compare the further annotation data to the at least one arrhythmia event detected based on the arrhythmia classifier; and determine an updated weight for each respective annotator of the at least one annotator based on comparing the further annotation data to the at least one arrhythmia event.

Clause 62: The system of any of clauses 40-61, wherein the remote computer system is further configured to: retrain the arrhythmia classifier based on the at least one further atypical ECG signal portion, the further annotation data, and the updated weight data.

Clause 63: The system of any of clauses 40-62, wherein the remote computer system is further configured to: compare the further annotation data to the at least one arrhythmia event detected based on the arrhythmia classifier; and transmit at least one further communication based on comparing the further annotation data to the at least one arrhythmia event.

Clause 64: The system of any of clauses 40-63, wherein the at least one further communication comprises at least one of: a recommendation to retest one or more of the at least one annotator; a recommendation to increase the respective skill score of one or more of the at least one annotator; a recommendation to decrease the respective skill score of one or more of the at least one annotator; or any combination thereof.

Clause 65: The system of any of clauses 40-64, wherein the remote computer system is further configured to: retrain the arrhythmia classifier based on the at least one further atypical ECG signal portion, the further annotation data, and the weight data.

Clause 66: The system of any of clauses 40-65, wherein the remote computer system is configured to: receive at least one updated skill score comprising a respective updated skill score for each of at least one annotator of the plurality of annotators; determine a respective updated weight for each of the at least one annotator based on the at least one updated skill score; and retrain the arrhythmia classifier based on the respective updated weight for each of the at least one annotator.

Clause 67: The system of any of clauses 40-66, wherein training the arrhythmia classifier comprises adjusting a hyperparameter of a loss function of the arrhythmia classifier based on the weight data.

Clause 68: The system of any of clauses 40-67, wherein training the arrhythmia classifier comprises: adjusting the respective weight for each of at least one annotator of the plurality of annotators based on a hyperparameter tuning process.

Clause 69: The system of any of clauses 40-68, wherein the respective skill score for each respective annotator of the plurality of annotators comprises an initial skill score, wherein the respective weight for each respective annotator comprises an initial weight, wherein the historical collection of the plurality of atypical ECG signal portions with the annotation data comprises a training subset of the plurality of atypical ECG signal portions and a validation subset of the plurality of atypical ECG signal portions, wherein the respective weight for each of the at least one annotator comprises a hyperparameter and an initial value of the hyperparameter comprises the initial weight, and wherein the hyperparameter tuning process comprises: training the arrhythmia classifier based on the training subset and the initial value of the hyperparameter; determining a metric associated with the initial value of the hyperparameter based on the validation subset; adjusting a value of the hyperparameter to provide an adjusted value of the hyperparameter; retraining the arrhythmia classifier based on the training subset and the adjusted value of the hyperparameter; and determining the metric associated with the adjusted value of the hyperparameter based on the validation set.

Clause 70: The system of any of clauses 40-69, wherein the hyperparameter tuning process further comprises repeating adjusting of the value of the hyperparameter, retraining of the arrhythmia classifier, and determining of the metric associated with the adjusted value of the hyperparameter until a termination condition is satisfied.

Clause 71: The system of any of clauses 40-70, wherein repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of: a value of the hyperparameter that optimizes the metric is found; a maximum number of iterations is reached; or any combination thereof.

Clause 72: The system of any of clauses 40-71, wherein the metric comprises at least one of accuracy, loss, area under curve (AUC), precision, recall, F1 score, or any combination thereof.

Clause 73: The system of any of clauses 40-72, wherein adjusting the value of the hyperparameter comprises at least one of: adjusting the value of the hyperparameter within a search space; adjusting the value of the hyperparameter within a range around the initial value; adjusting the value of the hyperparameter within a range around the initial skill score; adjusting the value of the hyperparameter randomly; or any combination thereof.

Clause 74: The system of any of clauses 40-73, wherein the external wearable heart monitoring device comprises a patch configured to be worn by the patient for an extended period of time, the patch comprising the plurality of ECG electrodes.

Clause 75: The system of any of clauses 40-74, wherein the patch is configured to be adhesively coupled to skin of the patient.

Clause 76: The system of any of clauses 40-75, wherein the adhesive patch is disposable.

Clause 77: The system of any of clauses 40-76, wherein the adhesive patch is configured to be continuously adhesively coupled to the skin of the patient for at least one of: 3-5 days, 5-7 days, 7-10 days, 10-14 days, or 14-30 days.

Clause 78: The system of any of clauses 40-77, wherein the external wearable heart monitoring device further comprises a cardiac monitoring unit configured to be removably attached to the patch.

Clause 79: The system of any of clauses 40-78, wherein the cardiac monitoring unit is configured to record the surface ECG activity of the patient sensed by the plurality of ECG electrodes and associated circuitry.

Clause 80: An atypical ECG lead arrhythmia classification system, comprising: a non-transitory computer-readable medium comprising an arrhythmia classifier comprising at least one neural network; and at least one processor operatively connected to the non-transitory computer-readable medium, the at least one processor configured to: receive a plurality of scores comprising a respective score for each respective annotator of a plurality of annotators; determine a respective initial weight for each respective annotator of the plurality of annotators based on the plurality of scores; receive a historical collection of a plurality of atypical electrocardiogram (ECG) signal portions with annotation data, the annotation data comprising at least one respective annotation for each respective atypical ECG signal portion of the plurality of atypical ECG signal portions; train the arrhythmia classifier based on the historical collection of the plurality of atypical ECG signal portions with the annotation data and based on weight data for the annotation data of the plurality of atypical ECG signal portions, the weight data comprising the respective initial weight for the respective annotator of each respective annotation; receive at least one further atypical ECG signal portion with further annotation data from at least one annotator of the plurality of annotators; analyze the at least one further atypical ECG signal portion to detect at least one arrhythmia event based on the arrhythmia classifier; compare the further annotation data to the at least one arrhythmia event; and transmit at least one communication based on comparing the further annotation data to the at least one arrhythmia event.

Clause 81: The system of clause 80, wherein the plurality of atypical ECG signal portions were obtained from an external wearable heart monitoring device configured for continuous and long-term monitoring of a patient comprising a plurality of ECG electrodes and associated circuitry configured to sense surface ECG activity of the patient, each ECG electrode configured to be anatomically located within a circumferential atypical zone of the patient's torso in an uninhibiting manner so as to allow for the patient to be ambulatory, wherein the plurality of ECG electrodes and associated circuitry are configured to provide at least one atypical ECG channel producing at least one atypical ECG signal for the patient.

Clause 82: The system of clause 80 or clause 81, wherein the plurality of ECG electrodes comprises at least four ECG electrodes.

Clause 83: The system of any of clauses 80-82, wherein the at least one atypical ECG channel comprises at least two atypical ECG channels, each atypical ECG channel associated with two respective ECG electrodes of the at least four ECG electrodes.

Clause 84: The system of any of clauses 80-83, wherein the at least four ECG electrodes comprise a front ECG electrode, a back ECG electrode, a first side ECG electrode, and a second side ECG electrode, wherein the at least two atypical ECG channels comprise a front-to-back (FB) ECG channel associated with the front ECG electrode and the back ECG electrode, and wherein the at least two typical ECG channels further comprise a side-to-side (SS) ECG channel associated with the first side ECG electrode and the second side ECG electrode.

Clause 85: The system of any of clauses 80-84, wherein the at least two atypical ECG channels comprise a first atypical ECG channel and a second atypical ECG channel substantially orthogonal to the first atypical ECG channel.

Clause 86: The system of any of clauses 80-85, wherein the at least one atypical ECG channel comprises at least three atypical ECG channels.

Clause 87: The system of any of clauses 80-86, wherein the at least one atypical ECG channel comprises at least four atypical ECG channels.

Clause 88: The system of any of clauses 80-87, wherein the at least one atypical ECG channel comprises a front-to-back (FB) ECG channel.

Clause 89: The system of any of clauses 80-88, wherein the at least one atypical ECG channel comprises a side-to-side (SS) ECG channel.

Clause 90: The system of any of clauses 80-89, wherein the at least one atypical ECG channel comprises at least one dynamically defined atypical ECG channel.

Clause 91: The system of any of clauses 80-90, wherein the associated circuitry is configured to analyze surface ECG activity of the patient and select at least two of the plurality of ECG electrodes to define the at least one dynamically defined atypical ECG channel.

Clause 92: The system of any of clauses 80-91, wherein the plurality of atypical ECG signal portions were obtained from an external wearable heart monitoring device configured for continuous and long-term monitoring of a patient comprising a plurality of ECG electrodes and associated circuitry configured to sense surface ECG activity of the patient, each ECG electrode configured to be anatomically located on the patient's thorax superior to the patient's xiphoid process and lateral to the patient's sternum, in an uninhibition manner so as to allow for the patient to be ambulatory, wherein the plurality of ECG electrodes and associated circuitry are configured to provide at least one atypical ECG channel producing at least one atypical ECG signal for the patient.

Clause 93: The system of any of clauses 80-92, wherein at least two ECG electrodes of the plurality of ECG electrodes are disposed within a predetermined distance on the patient's thorax superior to the patient's xiphoid process and lateral to the patient's sternum.

Clause 94: The system of any of clauses 80-93, wherein the predetermined distance comprises 15 centimeters, and wherein the at least two ECG electrodes are spaced less than 15 centimeters.

Clause 95: The system of any of clauses 80-94, wherein the at least two ECG electrodes are spaced less than 10 centimeters.

Clause 96: The system of any of clauses 80-95, wherein the at least two ECG electrodes are spaced 5-15 centimeters.

Clause 97: The system of any of clauses 80-96, wherein the at least two ECG electrodes are spaced less than 5 centimeters.

Clause 98: The system of any of clauses 80-97, wherein the external wearable heart monitoring device comprises a single adhesive patch.

Clause 99: The system of any of clauses 80-98, wherein the plurality of ECG electrodes are all on one side of the patient's sternum.

Clause 100: The system of any of clauses 80-99, wherein the plurality of ECG electrodes are left lateral to the patient's sternum.

Clause 101: The system of any of clauses 80-100, wherein the plurality of ECG electrodes are right lateral to the patient's sternum.

Clause 102: The system of any of clauses 80-101, wherein the respective score for each respective annotator is based on a respective skill level of the respective annotator.

Clause 103: The system of any of clauses 80-102, wherein the respective score for each respective annotator comprises a skill score.

Clause 104: The system of any of clauses 80-103, wherein the skill score comprises an integer value from one to four.

Clause 105: The system of any of clauses 80-104, wherein the skill score comprises an integer value from one to five.

Clause 106: The system of any of clauses 80-105, wherein the skill score comprises an integer value from one to ten.

Clause 107: The system of any of clauses 80-106, wherein the skill score comprises an integer value from one to 100.

Clause 108: The system of any of clauses 80-107, wherein the skill score comprises one of 25, 50, 75, or 100.

Clause 109: The system of any of clauses 80-108, wherein the skill score comprises a value from zero to one.

Clause 110: The system of any of clauses 80-109, wherein the at least one processor is further configured to: determine an updated weight for each respective annotator of the at least one annotator based on comparing the further annotation data to the at least one arrhythmia event.

Clause 111: The system of any of clauses 80-110, wherein the at least one processor is further configured to: retrain the arrhythmia classifier based on the at least one further atypical ECG signal portion, the further annotation data, and the updated weight data.

Clause 112: The system of any of clauses 80-111, wherein the at least one communication comprises at least one of: a recommendation to retest one or more of the at least one annotator; a recommendation to increase the respective skill score of one or more of the at least one annotator; a recommendation to decrease the respective skill score of one or more of the at least one annotator; or any combination thereof.

Clause 113: The system of any of clauses 80-112, wherein the at least one processor is further configured to: retrain the arrhythmia classifier based on the at least one further atypical ECG signal portion, the further annotation data, and the initial weight data.

Clause 114: The system of any of clauses 80-113, wherein the at least one processor is configured to: receive at least one updated skill score comprising a respective updated skill score for each of at least one annotator of the plurality of annotators; determine a respective updated weight for each of the at least one annotator based on the at least one updated skill score; and retrain the arrhythmia classifier based on the respective updated weight for each of the at least one annotator.

Clause 115: The system of any of clauses 80-114, wherein training the arrhythmia classifier comprises adjusting a hyperparameter of a loss function of the arrhythmia classifier based on the weight data.

Clause 116: The system of any of clauses 80-115, wherein training the arrhythmia classifier comprises: adjusting the respective weight for each of at least one annotator of the plurality of annotators based on a hyperparameter tuning process.

Clause 117: The system of any of clauses 80-116, wherein the respective skill score for each respective annotator of the plurality of annotators comprises an initial skill score, wherein the respective weight for each respective annotator comprises an initial weight, wherein the historical collection of the plurality of atypical ECG signal portions with the annotation data comprises a training subset of the plurality of atypical ECG signal portions and a validation subset of the plurality of atypical ECG signal portions, wherein the respective weight for each of the at least one annotator comprises a hyperparameter and an initial value of the hyperparameter comprises the initial weight, and wherein the hyperparameter tuning process comprises: training the arrhythmia classifier based on the training subset and the initial value of the hyperparameter; determining a metric associated with the initial value of the hyperparameter based on the validation subset; adjusting a value of the hyperparameter to provide an adjusted value of the hyperparameter; retraining the arrhythmia classifier based on the training subset and the adjusted value of the hyperparameter; and determining the metric associated with the adjusted value of the hyperparameter based on the validation set.

Clause 118: The system of any of clauses 80-117, wherein the hyperparameter tuning process further comprises repeating adjusting of the value of the hyperparameter, retraining of the arrhythmia classifier, and determining of the metric associated with the adjusted value of the hyperparameter until a termination condition is satisfied.

Clause 119: The system of any of clauses 80-118, wherein repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of: a value of the hyperparameter that optimizes the metric is found; a maximum number of iterations is reached; or any combination thereof.

Clause 120: The system of any of clauses 80-119, wherein the metric comprises at least one of accuracy, loss, area under curve (AUC), precision, recall, F1 score, or any combination thereof.

Clause 121: The system of any of clauses 80-120, wherein adjusting the value of the hyperparameter comprises at least one of: adjusting the value of the hyperparameter within a search space; adjusting the value of the hyperparameter within a range around the initial value; adjusting the value of the hyperparameter within a range around the initial skill score; adjusting the value of the hyperparameter randomly; or any combination thereof.

Clause 122: A wearable atypical electrocardiogram (ECG) lead atrial fibrillation monitoring system for identifying atrial fibrillation experienced by a patient, comprising: an external wearable heart monitoring device configured for continuous and long-term monitoring of a patient comprising: a plurality of ECG electrodes and associated circuitry configured to sense surface ECG activity of the patient, each ECG electrode configured to be anatomically located within a circumferential atypical zone of the patient's torso in an uninhibiting manner so as to allow for the patient to be ambulatory, wherein the plurality of ECG electrodes and associated circuitry are configured to provide at least one atypical ECG channel producing at least one atypical ECG signal for the patient; and a non-transitory computer-readable medium comprising an atrial fibrillation classifier comprising at least one neural network, wherein the neural network is trained based on a historical collection of a plurality of atypical ECG signal portions with annotation data, the annotation data comprising at least one respective annotation for each respective ECG signal portion of the plurality of ECG signal portions, and wherein the neural network is further trained based on weight data for the annotation data of the atypical ECG signal portions, the weight data comprising a respective weight for each respective annotation based on a respective annotator of the respective annotation; and at least one processor operatively connected to the at least one atypical ECG channel and the non-transitory computer-readable medium, the at least one processor configured to: receive the at least one atypical ECG signal of the at least one atypical ECG channel; monitor the at least one atypical ECG signal to detect at least one atrial fibrillation event based on the atrial fibrillation classifier; and transmit at least one communication based on the at least one atrial fibrillation event to a remote computer system.

Clause 123: The system of clause 122, wherein the plurality of ECG electrodes comprises at least four ECG electrodes.

Clause 124: The system of clause 122 or clause 123, wherein the at least one atypical ECG channel comprises at least two atypical ECG channels, each atypical ECG channel associated with two respective ECG electrodes of the at least four ECG electrodes.

Clause 125: The system of any of clauses 122-124, wherein the at least four ECG electrodes comprise a front ECG electrode, a back ECG electrode, a first side ECG electrode, and a second side ECG electrode, wherein the at least two atypical ECG channels comprise a front-to-back (FB) ECG channel associated with the front ECG electrode and the back ECG electrode, and wherein the at least two typical ECG channels further comprise a side-to-side (SS) ECG channel associated with the first side ECG electrode and the second side ECG electrode.

Clause 126: The system of any of clauses 122-125, wherein the at least two atypical ECG channels comprise a first atypical ECG channel and a second atypical ECG channel substantially orthogonal to the first atypical ECG channel.

Clause 127: The system of any of clauses 122-126, wherein the at least one atypical ECG channel comprises at least three atypical ECG channels.

Clause 128: The system of any of clauses 122-127, wherein the at least one atypical ECG channel comprises at least four atypical ECG channels.

Clause 129: The system of any of clauses 122-128, wherein the at least one atypical ECG channel comprises a front-to-back (FB) ECG channel.

Clause 130: The system of any of clauses 122-129, wherein the at least one atypical ECG channel comprises a side-to-side (SS) ECG channel.

Clause 131: The system of any of clauses 122-130, wherein the at least one atypical ECG channel comprises at least one dynamically defined atypical ECG channel.

Clause 132: The system of any of clauses 122-131, wherein the associated circuitry is configured to analyze surface ECG activity of the patient and select at least two of the plurality of ECG electrodes to define the at least one dynamically defined atypical ECG channel.

Clause 133: The system of any of clauses 122-132, wherein the respective weight for each respective annotator is based on a respective skill level of the respective annotator.

Clause 134: The system of any of clauses 122-133, wherein the respective skill level for each respective annotator comprises a skill score.

Clause 135: The system of any of clauses 122-134, wherein the skill score comprises an integer value from one to four.

Clause 136: The system of any of clauses 122-135, wherein the skill score comprises an integer value from one to five.

Clause 137: The system of any of clauses 122-136, wherein the skill score comprises an integer value from one to ten.

Clause 138: The system of any of clauses 122-137, wherein the skill score comprises an integer value from one to 100.

Clause 139: The system of any of clauses 122-138, wherein the skill score comprises one of 25, 50, 75, or 100.

Clause 140: The system of any of clauses 122-139, wherein the skill score comprises a value from zero to one.

Clause 141: The system of any of clauses 122-140, wherein the remote computer system is configured to: receive a plurality of skill scores comprising a respective skill score for each respective annotator, wherein a plurality of annotators comprises each respective annotator; and determine the respective weight for each respective annotator based on the plurality of scores.

Clause 142: The system of any of clauses 122-141, wherein the remote computer system is further configured to: receive the historical collection of the plurality of atypical ECG signal portions with the annotation data; and train the atrial fibrillation classifier based on the historical collection of the plurality of atypical ECG signal portions with the annotation data and based on the weight data.

Clause 143: The system of any of clauses 122-142, wherein the at least one communication comprises at least one further atypical ECG signal portion associated with the at least one atrial fibrillation event; wherein the remote computer system is further configured to: receive the at least one communication comprising the at least one further atypical ECG signal portion; and receive further annotation data associated with the at least one further atypical ECG signal portion from at least one annotator of the plurality of annotators.

Clause 144: The system of any of clauses 122-143, wherein the remote computer system is further configured to: compare the further annotation data to the at least one atrial fibrillation event detected based on the atrial fibrillation classifier; and determine an updated weight for each respective annotator of the at least one annotator based on comparing the further annotation data to the at least one atrial fibrillation event.

Clause 145: The system of any of clauses 122-144, wherein the remote computer system is further configured to: retrain the atrial fibrillation classifier based on the at least one further atypical ECG signal portion, the further annotation data, and the updated weight data.

Clause 146: The system of any of clauses 122-145, wherein the remote computer system is further configured to: compare the further annotation data to the at least one atrial fibrillation event detected based on the atrial fibrillation classifier; and transmit at least one further communication based on comparing the further annotation data to the at least one atrial fibrillation event.

Clause 147: The system of any of clauses 122-146, wherein the at least one further communication comprises at least one of: a recommendation to retest one or more of the at least one annotator; a recommendation to increase the respective skill score of one or more of the at least one annotator; a recommendation to decrease the respective skill score of one or more of the at least one annotator; or any combination thereof.

Clause 148: The system of any of clauses 122-147, wherein the remote computer system is further configured to: retrain the atrial fibrillation classifier based on the at least one further atypical ECG signal portion, the further annotation data, and the weight data.

Clause 149: The system of any of clauses 122-148, wherein the remote computer system is configured to: receive at least one updated skill score comprising a respective updated skill score for each of at least one annotator of the plurality of annotators; determine a respective updated weight for each of the at least one annotator based on the at least one updated skill score; and retrain the atrial fibrillation classifier based on the respective updated weight for each of the at least one annotator.

Clause 150: The system of any of clauses 122-149, wherein training the atrial fibrillation classifier comprises adjusting a hyperparameter of a loss function of the atrial fibrillation classifier based on the weight data.

Clause 151: The system of any of clauses 122-150, wherein training the atrial fibrillation classifier comprises: adjusting the respective weight for each of at least one annotator of the plurality of annotators based on a hyperparameter tuning process.

Clause 152: The system of any of clauses 122-151, wherein the respective skill score for each respective annotator of the plurality of annotators comprises an initial skill score, wherein the respective weight for each respective annotator comprises an initial weight, wherein the historical collection of the plurality of atypical ECG signal portions with the annotation data comprises a training subset of the plurality of atypical ECG signal portions and a validation subset of the plurality of atypical ECG signal portions, wherein the respective weight for each of the at least one annotator comprises a hyperparameter and an initial value of the hyperparameter comprises the initial weight, and wherein the hyperparameter tuning process comprises: training the atrial fibrillation classifier based on the training subset and the initial value of the hyperparameter; determining a metric associated with the initial value of the hyperparameter based on the validation subset; adjusting a value of the hyperparameter to provide an adjusted value of the hyperparameter; retraining the atrial fibrillation classifier based on the training subset and the adjusted value of the hyperparameter; and determining the metric associated with the adjusted value of the hyperparameter based on the validation set.

Clause 153: The system of any of clauses 122-152, wherein the hyperparameter tuning process further comprises repeating adjusting of the value of the hyperparameter, retraining of the atrial fibrillation classifier, and determining of the metric associated with the adjusted value of the hyperparameter until a termination condition is satisfied.

Clause 154: The system of any of clauses 122-153, wherein repeating adjusting of the value of the hyperparameter, retraining of the atrial fibrillation classifier, and determining of the metric associated with the adjusted value of the hyperparameter until the termination condition is satisfied comprises repeating adjusting of the value of the hyperparameter, retraining of the atrial fibrillation classifier, and determining of the metric associated with the adjusted value of the hyperparameter until at least one of: a value of the hyperparameter that optimizes the metric is found; a maximum number of iterations is reached; or any combination thereof.

Clause 155: The system of any of clauses 122-154, wherein the metric comprises at least one of accuracy, loss, area under curve (AUC), precision, recall, F1 score, or any combination thereof.

Clause 156: The system of any of clauses 122-155, wherein adjusting the value of the hyperparameter comprises at least one of: adjusting the value of the hyperparameter within a search space; adjusting the value of the hyperparameter within a range around the initial value; adjusting the value of the hyperparameter within a range around the initial skill score; adjusting the value of the hyperparameter randomly; or any combination thereof.

Clause 157: The system of any of clauses 122-156, wherein the external wearable heart monitoring device comprises a garment configured to be worn about a torso of the patient for an extended period of time and further configured to house the plurality of ECG electrodes.

Clause 158: The system of any of clauses 122-157, wherein the garment comprises a plurality of receptacles configured to receive the plurality of ECG electrodes.

Clause 159: The system of any of clauses 122-158, wherein the external wearable heart monitoring device comprises a plurality therapy electrodes configured to be housed in the garment.

Clause 160: The system of any of clauses 122-159, wherein the external wearable heart monitoring device is configured to: determine whether the patient is experiencing a treatable cardiac atrial fibrillation; and deliver one or more therapeutic shocks to the patient via the plurality of therapy electrodes upon determining that the patient is experiencing a treatable cardiac atrial fibrillation.

Clause 161: A wearable atypical electrocardiogram (ECG) lead atrial fibrillation monitoring system for identifying atrial fibrillation experienced by a patient, comprising: an external wearable heart monitoring device configured for continuous and long-term monitoring of a patient comprising: a plurality of ECG electrodes and associated circuitry configured to sense surface ECG activity of the patient, each ECG electrode configured to be anatomically located on the patient's thorax superior to the patient's xiphoid process and lateral to the patient's sternum, in an uninhibiting manner so as to allow for the patient to be ambulatory, wherein the plurality of ECG electrodes and associated circuitry are configured to provide at least one atypical ECG channel producing at least one atypical ECG signal for the patient; and a non-transitory computer-readable medium comprising an atrial fibrillation classifier comprising at least one neural network, wherein the neural network is trained based on a historical collection of a plurality of atypical ECG signal portions with annotation data, the annotation data comprising at least one respective annotation for each respective ECG signal portion of the plurality of ECG signal portions, and wherein the neural network is further trained based on weight data for the annotation data of the ECG signal portions, the weight data comprising a respective weight for each respective annotation based on a respective annotator of the respective annotation; and at least one processor operatively connected to the at least one atypical ECG channel and the non-transitory computer-readable medium, the at least one processor configured to: receive the at least one atypical ECG signal of the at least one atypical ECG channel; monitor the at least one atypical ECG signal to detect at least one atrial fibrillation event based on the atrial fibrillation classifier; and transmit at least one communication based on the at least one atrial fibrillation event to a remote computer system.

Clause 162: The system of clause 161, wherein at least two ECG electrodes of the plurality of ECG electrodes are disposed within a predetermined distance on the patient's thorax superior to the patient's xiphoid process and lateral to the patient's sternum.

Clause 163: The system of clause 161 or clause 162, wherein the predetermined distance comprises 15 centimeters, and wherein the at least two ECG electrodes are spaced less than 15 centimeters.

Clause 164: The system of any of clauses 161-163, wherein the at least two ECG electrodes are spaced less than 10 centimeters.

Clause 165: The system of any of clauses 161-164, wherein the at least two ECG electrodes are spaced 5-15 centimeters.

Clause 166: The system of any of clauses 161-165, wherein the at least two ECG electrodes are spaced less than 5 centimeters.

Clause 167: The system of any of clauses 161-166, wherein the external wearable heart monitoring device comprises a single adhesive patch.

Clause 168: The system of any of clauses 161-167, wherein the plurality of ECG electrodes are all on one side of the patient's sternum.

Clause 169: The system of any of clauses 161-170, wherein the plurality of ECG electrodes are left lateral to the patient's sternum.

Clause 170: The system of any of clauses 161-169, wherein the plurality of ECG electrodes are right lateral to the patient's sternum.

Clause 171: The system of any of clauses 161-170, wherein the respective weight for each respective annotator is based on a respective skill level of the respective annotator.

Clause 172: The system of any of clauses 161-171, wherein the respective skill level for each respective annotator comprises a skill score.

Clause 173: The system of any of clauses 161-172, wherein the skill score comprises an integer value from one to four.

Clause 174: The system of any of clauses 161-173, wherein the skill score comprises an integer value from one to five.

Clause 175: The system of any of clauses 161-174, wherein the skill score comprises an integer value from one to ten.

Clause 176: The system of any of clauses 161-175, wherein the skill score comprises an integer value from one to 100.

Clause 177: The system of any of clauses 161-176, wherein the skill score comprises one of 25, 50, 75, or 100.

Clause 178: The system of any of clauses 161-177, wherein the skill score comprises a value from zero to one.

Clause 179: The system of any of clauses 161-178, wherein the remote computer system is configured to: receive a plurality of skill scores comprising a respective skill score for each respective annotator, wherein a plurality of annotators comprises each respective annotator; and determine the respective weight for each respective annotator based on the plurality of scores.

Clause 180: The system of any of clauses 161-179, wherein the remote computer system is configured to: receive the historical collection of the plurality of atypical ECG signal portions with the annotation data; and train the atrial fibrillation classifier based on the historical collection of the plurality of atypical ECG signal portions with the annotation data and based on the weight data.

Clause 181: The system of any of clauses 161-180, wherein the at least one communication comprises at least one further atypical ECG signal portion associated with the at least one atrial fibrillation event; wherein the remote computer system is further configured to: receive the at least one communication comprising the at least one further atypical ECG signal portion; and receive further annotation data associated with the at least one further atypical ECG signal portion from at least one annotator of the plurality of annotators.

Clause 182: The system of any of clauses 161-181, wherein the remote computer system is further configured to: compare the further annotation data to the at least one atrial fibrillation event detected based on the atrial fibrillation classifier; and determine an updated weight for each respective annotator of the at least one annotator based on comparing the further annotation data to the at least one atrial fibrillation event.

Clause 183: The system of any of clauses 161-182, wherein the remote computer system is further configured to: retrain the atrial fibrillation classifier based on the at least one further atypical ECG signal portion, the further annotation data, and the updated weight data.

Clause 184: The system of any of clauses 161-183, wherein the remote computer system is further configured to: compare the further annotation data to the at least one atrial fibrillation event detected based on the atrial fibrillation classifier; and transmit at least one further communication based on comparing the further annotation data to the at least one atrial fibrillation event.

Clause 185: The system of any of clauses 161-184, wherein the at least one further communication comprises at least one of: a recommendation to retest one or more of the at least one annotator; a recommendation to increase the respective skill score of one or more of the at least one annotator; a recommendation to decrease the respective skill score of one or more of the at least one annotator; or any combination thereof.

Clause 186: The system of any of clauses 161-185, wherein the remote computer system is further configured to: retrain the atrial fibrillation classifier based on the at least one further atypical ECG signal portion, the further annotation data, and the weight data.

Clause 187: The system of any of clauses 161-186, wherein the remote computer system is configured to: receive at least one updated skill score comprising a respective updated skill score for each of at least one annotator of the plurality of annotators; determine a respective updated weight for each of the at least one annotator based on the at least one updated skill score; and retrain the atrial fibrillation classifier based on the respective updated weight for each of the at least one annotator.

Clause 188: The system of any of clauses 161-187, wherein training the atrial fibrillation classifier comprises adjusting a hyperparameter of a loss function of the atrial fibrillation classifier based on the weight data.

Clause 189: The system of any of clauses 161-188, wherein training the atrial fibrillation classifier comprises: adjusting the respective weight for each of at least one annotator of the plurality of annotators based on a hyperparameter tuning process.

Clause 190: The system of any of clauses 161-189, wherein the respective skill score for each respective annotator of the plurality of annotators comprises an initial skill score, wherein the respective weight for each respective annotator comprises an initial weight, wherein the historical collection of the plurality of atypical ECG signal portions with the annotation data comprises a training subset of the plurality of atypical ECG signal portions and a validation subset of the plurality of atypical ECG signal portions, wherein the respective weight for each of the at least one annotator comprises a hyperparameter and an initial value of the hyperparameter comprises the initial weight, and wherein the hyperparameter tuning process comprises: training the atrial fibrillation classifier based on the training subset and the initial value of the hyperparameter; determining a metric associated with the initial value of the hyperparameter based on the validation subset; adjusting a value of the hyperparameter to provide an adjusted value of the hyperparameter; retraining the atrial fibrillation classifier based on the training subset and the adjusted value of the hyperparameter; and determining the metric associated with the adjusted value of the hyperparameter based on the validation set.

Clause 191: The system of any of clauses 161-190, wherein the hyperparameter tuning process further comprises repeating adjusting of the value of the hyperparameter, retraining of the atrial fibrillation classifier, and determining of the metric associated with the adjusted value of the hyperparameter until a termination condition is satisfied.

Clause 192: The system of any of clauses 161-191, wherein repeating adjusting of the value of the hyperparameter, retraining of the atrial fibrillation classifier, and determining of the metric associated with the adjusted value of the hyperparameter until the termination condition is satisfied comprises repeating adjusting of the value of the hyperparameter, retraining of the atrial fibrillation classifier, and determining of the metric associated with the adjusted value of the hyperparameter until at least one of: a value of the hyperparameter that optimizes the metric is found; a maximum number of iterations is reached; or any combination thereof.

Clause 193: The system of any of clauses 161-192, wherein the metric comprises at least one of accuracy, loss, area under curve (AUC), precision, recall, F1 score, or any combination thereof.

Clause 194: The system of any of clauses 161-193, wherein adjusting the value of the hyperparameter comprises at least one of: adjusting the value of the hyperparameter within a search space; adjusting the value of the hyperparameter within a range around the initial value; adjusting the value of the hyperparameter within a range around the initial skill score; adjusting the value of the hyperparameter randomly; or any combination thereof.

Clause 195: The system of any of clauses 161-194, wherein the external wearable heart monitoring device comprises a patch configured to be worn by the patient for an extended period of time, the patch comprising the plurality of ECG electrodes.

Clause 196: The system of any of clauses 161-195, wherein the patch is configured to be adhesively coupled to skin of the patient.

Clause 197: The system of any of clauses 161-196, wherein the adhesive patch is disposable.

Clause 198: The system of any of clauses 161-197, wherein the adhesive patch is configured to be continuously adhesively coupled to the skin of the patient for at least one of: 3-5 days, 5-7 days, 7-10 days, 10-14 days, or 14-30 days.

Clause 199: The system of any of clauses 161-198, wherein the external wearable heart monitoring device further comprises a cardiac monitoring unit configured to be removably attached to the patch.

Clause 200: The system of any of clauses 161-199, wherein the cardiac monitoring unit is configured to record the surface ECG activity of the patient sensed by the plurality of ECG electrodes and associated circuitry.

Clause 201: A wearable electrocardiogram (ECG) lead arrhythmia monitoring system for identifying arrhythmias experienced by a patient, comprising: an external wearable heart monitoring device configured for continuous and long-term monitoring of a patient comprising: a plurality of ECG electrodes and associated circuitry configured to sense surface ECG activity of the patient, wherein the plurality of ECG electrodes and associated circuitry are configured to provide at least one ECG channel producing at least one ECG signal for the patient; and a non-transitory computer-readable medium comprising an arrhythmia classifier comprising at least one neural network, wherein the neural network is trained based on a historical collection of a plurality of ECG signal portions with annotation data, the annotation data comprising at least one respective annotation for each respective ECG signal portion of the plurality of ECG signal portions, and wherein the neural network is further trained based on weight data for the annotation data of the plurality of ECG signal portions, the weight data comprising a respective weight for each respective annotation based on a respective annotator of the respective annotation; and at least one processor operatively connected to the at least one ECG channel and the non-transitory computer-readable medium, the at least one processor configured to: receive the at least one ECG signal of the at least one ECG channel; monitor the at least one ECG signal to detect at least one arrhythmia event based on the arrhythmia classifier; and transmit at least one communication based on the at least one arrhythmia event to a remote computer system.

Clause 202: The system of clause 201, wherein the plurality of ECG electrodes comprises at least three ECG electrodes.

Clause 203: The system of clause 201 or clause 202, wherein the at least three ECG electrodes comprise a right arm (RA) EGG electrode, a left arm (LA) ECG electrode, and a left leg (LL) ECG electrode.

Clause 204: The system of any of clauses 201-203, wherein the at least one ECG channel comprises a lead I channel between the RA ECG electrode and the LA ECG electrode, a lead II channel between the RCA ECG electrode and the LL ECG electrode, and a lead III channel between the LA ECG electrode and the LL ECG electrode.

Clause 205: The system of any of clauses 201-204, wherein the plurality of ECG electrodes comprises at least five ECG electrodes.

Clause 206: The system of any of clauses 201-205, wherein the at least five ECG electrodes comprise a right arm (RA) EGG electrode, a right leg (RL) ECG electrode, a left arm (LA) ECG electrode, a left leg (LL) ECG electrode, and a chest ECG electrode.

Clause 207: The system of any of clauses 201-206, wherein the at least one ECG channel comprises a lead I channel, a lead II channel, a lead III channel, and at least one unipolar lead channel.

Clause 208: The system of any of clauses 201-207, wherein the plurality of ECG electrodes comprises at least 10 ECG electrodes.

Clause 209: The system of any of clauses 201-208, wherein the at least 10 ECG electrodes comprise a right arm (RA) EGG electrode, a right leg (RL) ECG electrode, a left arm (LA) ECG electrode, a left leg (LL) ECG electrode, and six precordial ECG electrodes.

Clause 210: The system of any of clauses 201-209, wherein the at least one ECG channel comprises at least six limb ECG channels and at least six precordial ECG channels.

Clause 211: The system of any of clauses 201-210, wherein the at least six limb ECG channels comprise a lead I channel, a lead II channel, a lead III channel, an augmented vector right (aVR) channel, an augmented vector left (aVL) channel, and an augmented vector foot (aVF) channel, and wherein the at least six precordial ECG channels comprise a V1 channel, a V2 channel, a V3 channel, a V4 channel, a V5 channel, and a V6 channel.

Clause 212: The system of any of clauses 201-211, wherein the respective weight for each respective annotator is based on a respective skill level of the respective annotator.

Clause 213: The system of any of clauses 201-212, wherein the respective skill level for each respective annotator comprises a skill score.

Clause 214: The system of any of clauses 201-213, wherein the skill score comprises one of: an integer value from one to four; an integer value from one to five; an integer value from one to ten; an integer value from one to 100; one of 25, 50, 75, or 100; or a value from zero to one.

Clause 215: The system of any of clauses 201-214, wherein the remote computer system is configured to: receive a plurality of skill scores comprising a respective skill score for each respective annotator, wherein a plurality of annotators comprises each respective annotator; and determine the respective weight for each respective annotator based on the plurality of skill scores.

Clause 216: The system of any of clauses 201-215, wherein the remote computer system is further configured to: receive the historical collection of the plurality of ECG signal portions with the annotation data; and train the arrhythmia classifier based on the historical collection of the plurality of ECG signal portions with the annotation data and based on the weight data.

Clause 217: The system of any of clauses 201-216, wherein the at least one communication comprises at least one further ECG signal portion associated with the at least one arrhythmia event; wherein the remote computer system is further configured to: receive the at least one communication comprising the at least one further ECG signal portion; and receive further annotation data associated with the at least one further ECG signal portion from at least one annotator of the plurality of annotators.

Clause 218: The system of any of clauses 201-217, wherein the remote computer system is further configured to: compare the further annotation data to the at least one arrhythmia event detected based on the arrhythmia classifier; and determine an updated weight for each respective annotator of the at least one annotator based on comparing the further annotation data to the at least one arrhythmia event.

Clause 219: The system of any of clauses 201-218, wherein the remote computer system is further configured to: retrain the arrhythmia classifier based on the at least one further ECG signal portion, the further annotation data, and the updated weight data.

Clause 220: The system of any of clauses 201-219, wherein the remote computer system is further configured to: compare the further annotation data to the at least one arrhythmia event detected based on the arrhythmia classifier; and transmit at least one further communication based on comparing the further annotation data to the at least one arrhythmia event.

Clause 221: The system of any of clauses 201-220, wherein the at least one further communication comprises at least one of: a recommendation to retest one or more of the at least one annotator; a recommendation to increase the respective skill score of one or more of the at least one annotator; a recommendation to decrease the respective skill score of one or more of the at least one annotator; or any combination thereof.

Clause 222: The system of any of clauses 201-221, wherein the remote computer system is further configured to: retrain the arrhythmia classifier based on the at least one further ECG signal portion, the further annotation data, and the weight data.

Clause 223: The system of any of clauses 201-222, wherein the remote computer system is configured to: receive at least one updated skill score comprising a respective updated skill score for each of at least one annotator of the plurality of annotators; determine a respective updated weight for each of the at least one annotator based on the at least one updated skill score; and retrain the arrhythmia classifier based on the respective updated weight for each of the at least one annotator.

Clause 224: The system of any of clauses 201-223, wherein training the arrhythmia classifier comprises adjusting a hyperparameter of a loss function of the arrhythmia classifier based on the weight data.

Clause 225: The system of any of clauses 201-224, wherein training the arrhythmia classifier comprises: adjusting the respective weight for each of at least one annotator of the plurality of annotators based on a hyperparameter tuning process.

Clause 226: The system of any of clauses 201-225, wherein the respective skill score for each respective annotator of the plurality of annotators comprises an initial skill score, wherein the respective weight for each respective annotator comprises an initial weight, wherein the historical collection of the plurality of ECG signal portions with the annotation data comprises a training subset of the plurality of ECG signal portions and a validation subset of the plurality of ECG signal portions, wherein the respective weight for each of the at least one annotator comprises a hyperparameter and an initial value of the hyperparameter comprises the initial weight, and wherein the hyperparameter tuning process comprises: training the arrhythmia classifier based on the training subset and the initial value of the hyperparameter; determining a metric associated with the initial value of the hyperparameter based on the validation subset; adjusting a value of the hyperparameter to provide an adjusted value of the hyperparameter; retraining the arrhythmia classifier based on the training subset and the adjusted value of the hyperparameter; and determining the metric associated with the adjusted value of the hyperparameter based on the validation set.

Clause 227: The system of any of clauses 201-226, wherein the hyperparameter tuning process further comprises repeating adjusting of the value of the hyperparameter, retraining of the arrhythmia classifier, and determining of the metric associated with the adjusted value of the hyperparameter until a termination condition is satisfied.

Clause 228: The system of any of clauses 201-227, wherein repeating adjusting of the value of the hyperparameter, retraining of the arrhythmia classifier, and determining of the metric associated with the adjusted value of the hyperparameter until the termination condition is satisfied comprises repeating adjusting of the value of the hyperparameter, retraining of the arrhythmia classifier, and determining of the metric associated with the adjusted value of the hyperparameter until at least one of: a value of the hyperparameter that optimizes the metric is found; a maximum number of iterations is reached; or any combination thereof.

Clause 229: The system of any of clauses 201-228, wherein the metric comprises at least one of accuracy, loss, area under curve (AUC), precision, recall, F1 score, or any combination thereof.

Clause 230: The system of any of clauses 201-229, wherein adjusting the value of the hyperparameter comprises at least one of: adjusting the value of the hyperparameter within a search space; adjusting the value of the hyperparameter within a range around the initial value; adjusting the value of the hyperparameter within a range around the initial skill score; adjusting the value of the hyperparameter randomly; or any combination thereof.

Clause 231: The system of any of clauses 201-230, wherein the plurality of ECG electrodes and associated circuitry are configured to provide at least one standard ECG channel producing at least one standard ECG signal for the patient.

Clause 232: The system of any of clauses 201-231, wherein the plurality of ECG electrodes and associated circuitry are configured to provide at least one standard ECG channel producing at least one standard ECG signal for the patient and at least one atypical ECG channel producing at least one atypical ECG signal for the patient.

Clause 233: The system of any of clauses 201-232, wherein the plurality of ECG electrodes and associated circuitry are configured to provide at least one of: at least one standard ECG channel producing at least one standard ECG signal for the patient, or at least one atypical ECG channel producing at least one atypical ECG signal for the patient.

Some embodiments of the current disclosure may include a system, method, or computer program product for cardiac diagnosis and/or monitoring with atypical ECG signals according to any one and/or another of the embodiments illustrated, described, and/or disclosed herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1A:
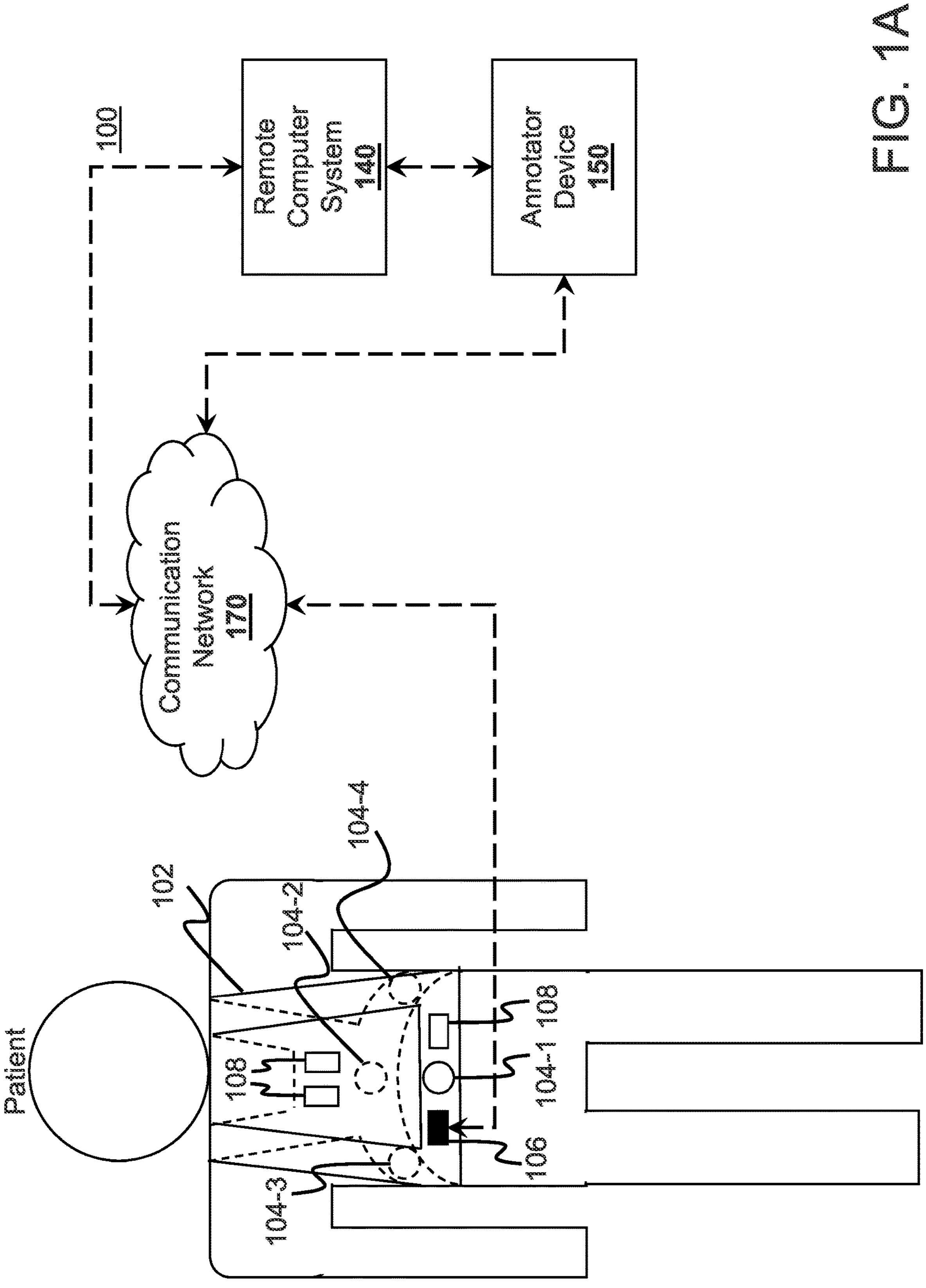
FIGS. 1A-1F show example block diagrams of a system for cardiac diagnosis and/or monitoring with atypical electrocardiogram (ECG) signals, according to some embodiments.

Certain cardiac monitoring and/or treatment devices may communicate ECG-based biometric data (e.g., ECG signal samples and/or ECG signal portions/strips) and non-ECG based biometric data (e.g., cardiovibrational data, radio frequency-based lung fluid metrics, respiration data, activity level data, motion data, position data, and/or patient posture data) associated with the patient to the cloud (e.g., to a remote server, a cardiac monitoring facility, and/or the like) for review (e.g., by technicians, prescribers/treating physicians, and/or the like). However, features of the disclosed subject matter recognize that such communication may require large bandwidth (e.g., all measured biometric data constantly streaming in real time and/or the like), may include a large amount of biometric data not associated with a cardiac event of interest (e.g., ECG-based biometric data associated with normal sinus rhythm (NSR) and/or the like), and may require human reviewers to review the large amounts of data without guidance as to which portions thereof are associated with cardiac events of interest. Additionally, features of the disclosed subject matter allow for accurate determination whether a human reviewer correctly identified and/or annotated cardiac events of interest in the biometric data. For example, features of the disclosed subject matter recognize that technicians may have different levels of skill (e.g., different levels of education, experience, expertise, and/or abilities). In some scenarios, it may be appreciated that it may be desirable to identify cardiac events of interest and/or minimize falsely identifying cardiac events of interest to avoid harm or injury to the patient (e.g., failure to provide needed treatment and/or providing treatment that is unnecessary, respectively). In some scenarios, features of the disclosed subject matter recognize that different human reviewers may disagree about whether a portion of biometric data (e.g., an ECG signal portion) includes a cardiac event and/or which type of cardiac event is included in the portion of biometric data. For example, different human reviewers (e.g., of different skill levels or even of the same level) may annotate the same portion of biometric data differently. Features of the disclosed subject matter recognize that such disagreement may result in inaccuracy, bias, lack of precision, and/or harm to a patient. In addition, when such annotations are used (e.g., for labels, for determining error and/or loss, and/or the like) to train a machine learning model (e.g., a classifier and/or the like), features of the disclosed subject matter recognize that this usage may result in inaccuracy, bias, lack of precision, and/or other difficulty in training or using the machine learning model (e.g., noisy labels).

Furthermore, certain wearable systems and/or devices may not include standard ECG leads. For example, features of the disclosed subject matter recognize that human reviewers may be trained and/or have experience reviewing ECG signals from standard ECG leads (e.g., a standard 12-lead ECG lead placement and/or a subset of those 12 leads). Features of the disclosed subject matter recognize that atypical (e.g., non-standard, uncommon, and/or the like) ECG leads (e.g., of certain wearable systems/devices) may result in ECG signals and/or portions thereof that are unfamiliar, difficult for human interpretation (e.g., difficult for human reviewers to see certain waves, such as P waves), and/or the like. As such, features of the disclosed subject matter allow for the use of biometric data obtained with atypical ECG leads without introducing additional difficulty in determining whether a human reviewer correctly identified and/or annotated cardiac events in the biometric data and/or in addressing disagreement between different human reviewers. Additionally, features of the disclosed subject matter recognize that machine learning models trained with data from typical (e.g., standard) ECG leads may be unsuitable for use with data from atypical ECG leads.

This disclosure relates to systems, methods, and computer program products for cardiac diagnosis and/or monitoring with electrocardiogram (ECG) signals. For example, one or more trained classifier(s), each of which including at least one neural network, may be used by a heart monitoring device (e.g., external, wearable, and/or the like heart monitoring device), a computer system, and/or the like to detect (e.g., identify and/or the like) a cardiac event (e.g., arrhythmia event, atrial fibrillation event, and/or the like) based on one or more ECG signals of one or more ECG channels. Example use scenarios include use of the systems, methods, and computer program products for cardiac diagnosis and/or monitoring in the context of mobile cardiac telemetry, cardiac holter monitoring (including extended cardiac holter monitoring), wearable cardiac monitors, wearable defibrillators, wearable cardioverter defibrillators, and other such ambulatory cardiac monitoring and/or treatment systems.

Figure 14A:
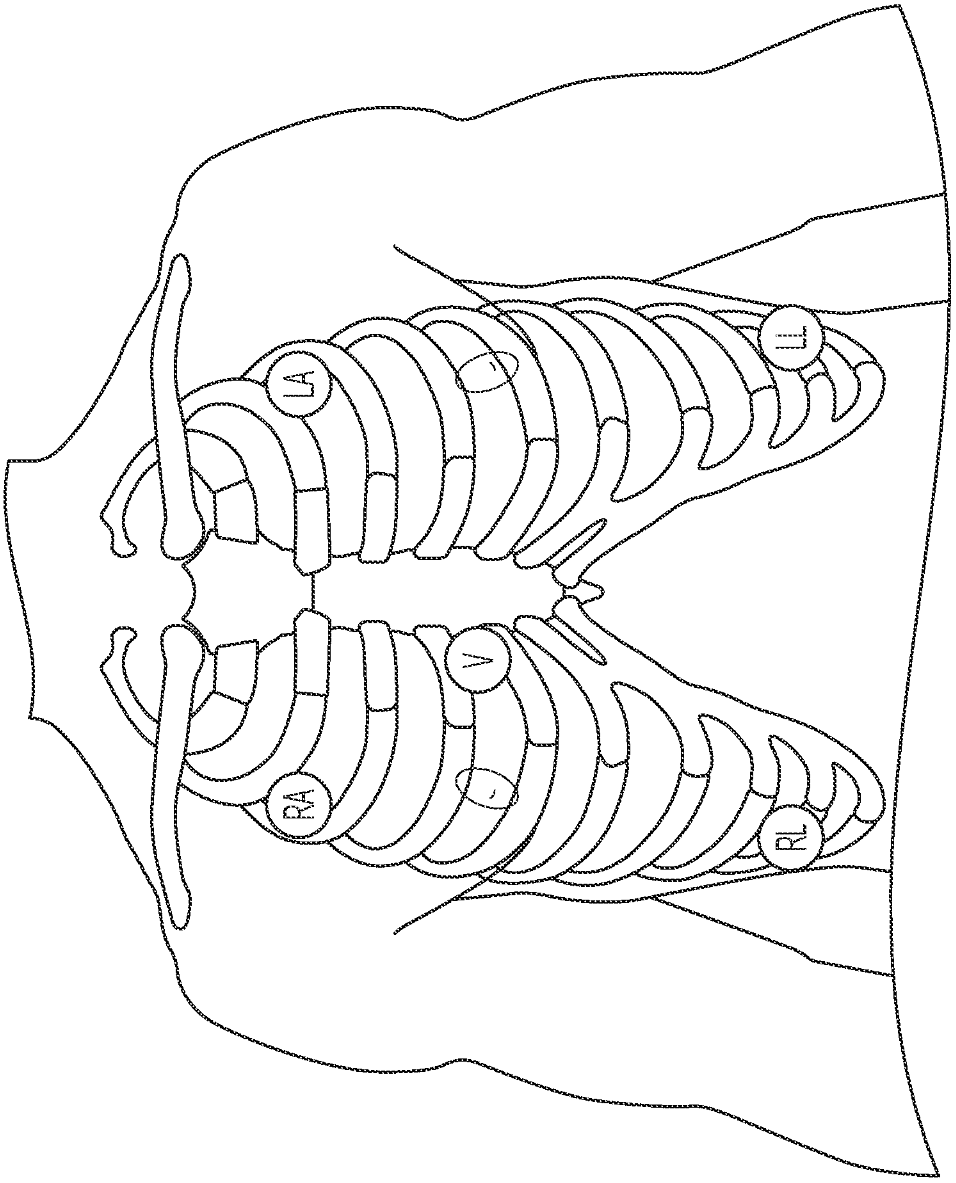
FIGS. 14A-14C illustrate example standard ECG lead placement, according to some embodiments.
Figure 14B:
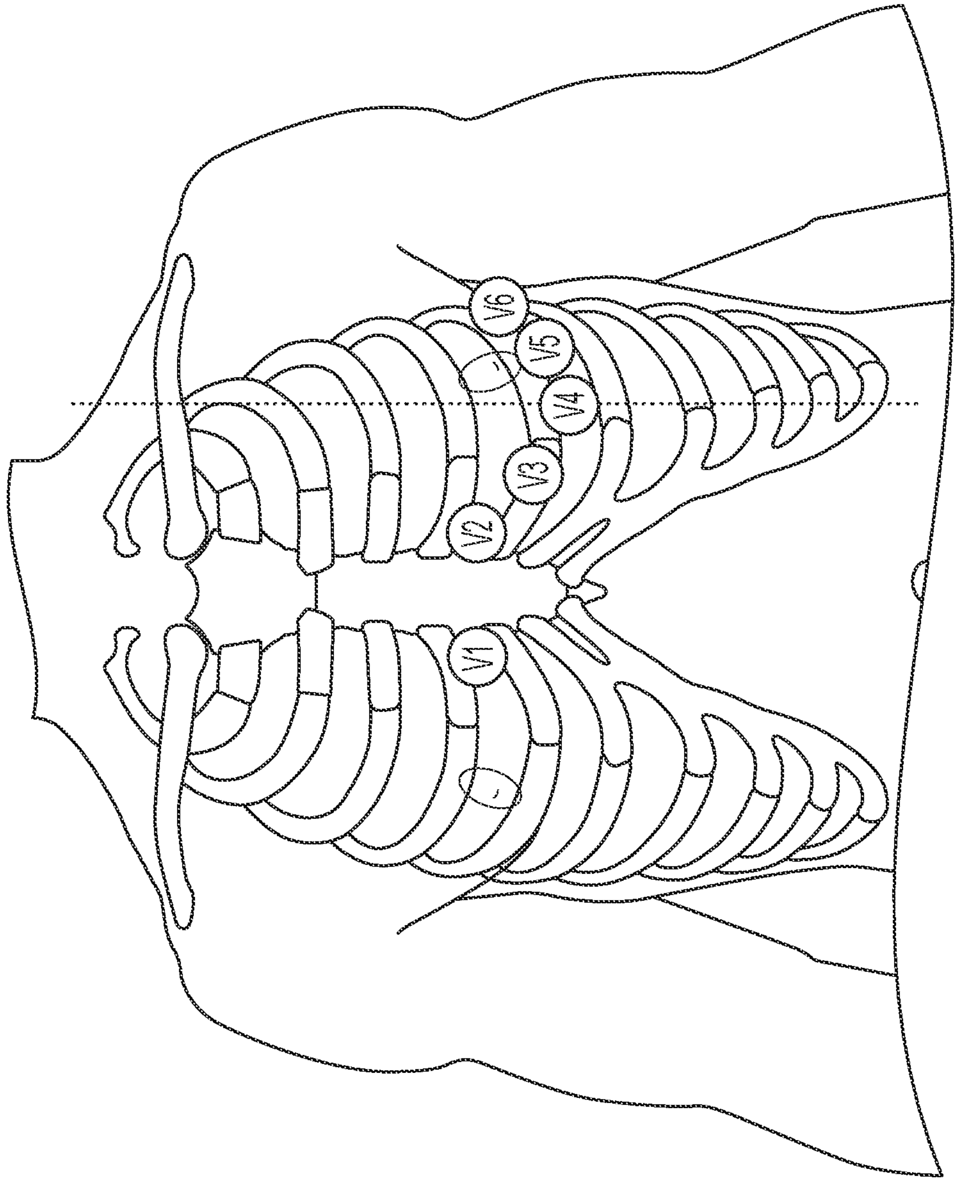

Referring to FIGS. 14A and 14B, example standard ECG lead systems include 3 lead systems, 5 lead systems, and 12 lead systems. For example, a 3 lead system may use 3 electrodes right are (RA), left arm (LA), and left leg (LL), and provide bipolar leads I, II, and III, as described herein. For example, a 5 lead system may use 5 electrodes RA, right leg (RL), LA, LL, and chest electrode (e.g., any of V1-V6), and provide a bipolar leads I, II, and II, and a single unipolar lead depending on position of chest electrode (e.g., any of positions V1-V6), as described herein. For example, a 12 lead ECG system may include six limb leads and six precordial leads, as described herein.

Figure 14C:
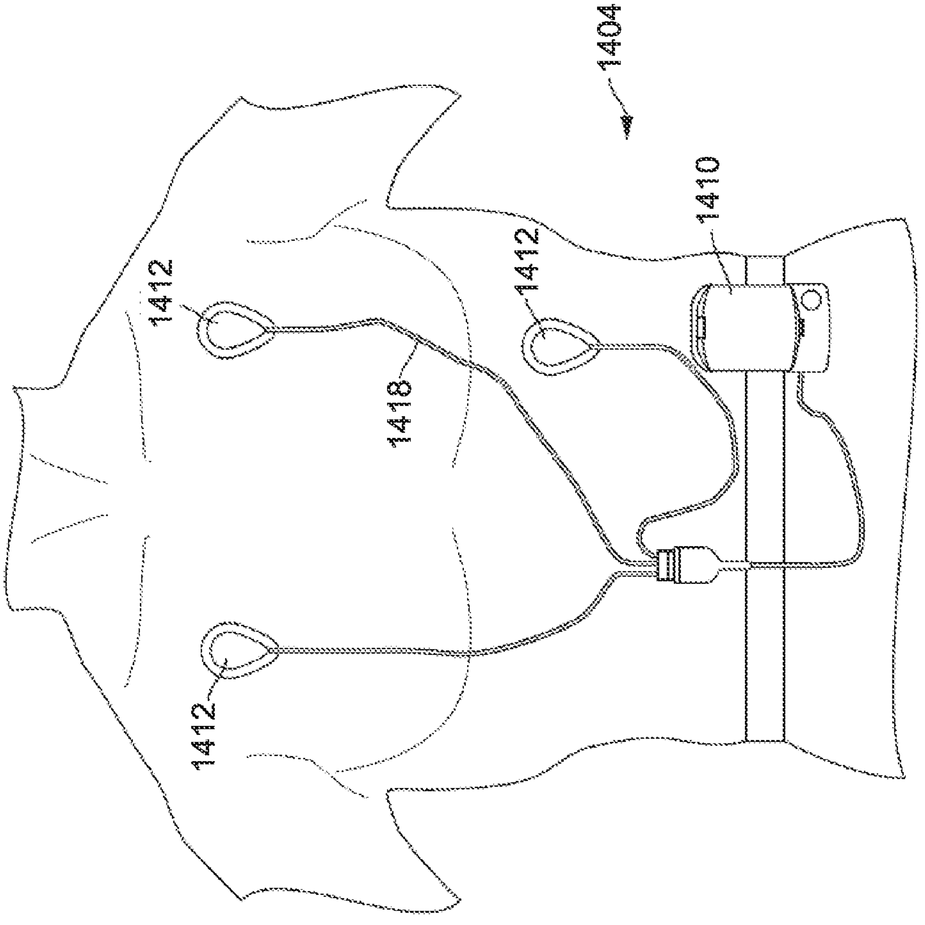

Referring to FIG. 14C, an exemplary wearable heart monitoring device 1400 is illustrated. As shown in FIG. 14C, in some embodiments, the wearable heart monitoring device 1400 may include a cardiac sensor 1404 that further includes individual electrodes 1412 configured to be adhered to the patient's body. Each individual electrode 1412 may be covered with a hydrogel for signal acquisition from the patient. The individual electrodes 1412 may be in wired communication with the sensor unit 1410 via cables 1418, as shown. The sensor unit 1410 may be worn, for example, on a belt of the patient via a belt clip attachment (not shown). In some embodiments, the sensor unit 1410 may communicate with a portable gateway (e.g., gateway device 160, as described herein, and/or the like), which may transmit signals from the sensor unit 1410 to a remote server (e.g., remote computer system 140, as described herein, and/or the like). In some embodiments, the sensor unit 1410 may communicate directly with the remote server (e.g., remote computer system 140, as described herein, and/or the like), as described herein.

In some embodiments, the individual electrodes 1412 may be positioned on the patient in a configuration suited for acquiring ECG signals from the patient. For example, as illustrated in FIG. 14C, the cardiac sensor 1404 may include three electrodes 1412, and two of the electrodes 1412 may be positioned near either side of the patient's collarbone and the third electrode 1412 may be positioned lower on the patient's thorax. Additionally or alternatively, in some embodiments, the cardiac sensor 1404 may include one or more motion sensors in the sensor unit 1410, similar to implementations of the cardiac sensor 1404 including the adhesive patch 1408 discussed above. In implementations, the cardiac sensor 1404 may include one or more motion sensors connected to the individual electrodes 1412. For instance, each electrode 1412 may have a connected motion sensor, or a particular electrode 1412 may have a connected motion sensor, such as the electrode 1412 configured to be positioned lower on the patient's thorax in FIG. 14C. In implementations, the cardiac sensor 1404 may include one or more motion sensors connected to the cables 1418.

In some embodiments, the external wearable heart monitoring device 1400 may be configured for continuous and long-term monitoring of a patient. A plurality of ECG electrodes 1412 and associated circuitry (e.g., of the sensor unit 1410 and/or the like) may be configured to sense surface ECG activity of the patient. For example, the ECG electrodes 1412 and associated circuitry (e.g., of the sensor unit 1410 and/or the like) may be configured to provide at least one ECG channel producing at least one ECG signal for the patient.

In some embodiments, the wearable heart monitoring device 1400 (e.g., the sensor unit 1410 thereof and/or the like) may include a non-transitory computer-readable medium comprising an arrhythmia (and/or atrial fibrillation) classifier comprising at least one neural network. The neural network may be trained based on a historical collection of a plurality of ECG signal portions with annotation data, as described herein. For example, the annotation data may include at least one respective annotation for each respective ECG signal portion of the plurality of ECG signal portions. The neural network may be further trained based on weight data for the annotation data of the plurality of ECG signal portions, as described herein. For example, the weight data may include a respective weight for each respective annotation based on a respective annotator of the respective annotation, as described herein.

In some embodiments, the wearable heart monitoring device 1400 (e.g., the sensor unit 1410 thereof and/or the like) may include at least one processor operatively connected to the at least one ECG channel and the non-transitory computer-readable medium. The processor(s) may be configured to receive the at least one ECG signal of the at least one ECG channel. The processor(s) may be configured to monitor the at least one ECG signal to detect at least one arrhythmia (and/or atrial fibrillation) event based on the arrhythmia (and/or atrial fibrillation) classifier. The processor(s) may be configured to transmit at least one communication based on the at least one arrhythmia (and/or atrial fibrillation) event to a remote server (e.g., remote computer system 140 and/or the like).

In some embodiments, the wearable heart monitoring device 1400 may include at least three ECG electrodes 1412. For example, the ECG electrodes 1412 may include an RA EGG electrode, an LA ECG electrode, and an LL ECG electrode, as described herein. Additionally or alternatively, the ECG channel(s) may include a lead I channel between the RA ECG electrode and the LA ECG electrode, a lead II channel between the RCA ECG electrode and the LL ECG electrode, and a lead III channel between the LA ECG electrode and the LL ECG electrode.

In some embodiments, the wearable heart monitoring device 1400 may include at least five ECG electrodes 1412. For example, the ECG electrodes 1412 may include an RA EGG electrode, an RL ECG electrode, an LA ECG electrode, an LL ECG electrode, and a chest ECG electrode, as described herein. Additionally or alternatively, the ECG channel(s) may include a (bipolar) lead I channel, a (bipolar) lead II channel, a (bipolar) lead III channel, and at least one unipolar lead channel.

In some embodiments, the wearable heart monitoring device 1400 may include at least 10 ECG electrodes 1412. For example, the ECG electrodes 1412 may include an RA EGG electrode, an RL ECG electrode, an LA ECG electrode, an LL ECG electrode, and six precordial (e.g., chest) ECG electrodes. In some embodiments, the ECG channel(s) may include at least six limb ECG channels and at least six precordial ECG channels. For example, the limb ECG channels may include a lead I channel, a lead II channel, a lead III channel, an augmented vector right (aVR) channel, an augmented vector left (aVL) channel, and an augmented vector foot (aVF) channel. Additionally or alternatively, the precordial ECG channels may include a V1 channel, a V2 channel, a V3 channel, a V4 channel, a V5 channel, and a V6 channel.

In some embodiments, the respective weight for each respective annotator may be based on a respective skill level of the respective annotator, as described herein. For example, the respective skill level for each respective annotator may include a skill score, as described herein. For example, the skill score may include one of an integer value from one to four; an integer value from one to five; an integer value from one to ten; an integer value from one to 100; one of 25, 50, 75, or 100; a value from zero to one; and/or the like.

In some embodiments, a remote server (e.g., the remote computer system 140 and/or the like) may be configured to receive a plurality of skill scores comprising a respective skill score for each respective annotator, as described herein. The remote server may determine the respective weight for each respective annotator based on the plurality of skill scores, as described herein. For example, the remote server may receive the historical collection of ECG signal portions with the annotation data and train the arrhythmia (and/or atrial fibrillation) classifier based on the historical collection of the plurality of ECG signal portions with the annotation data and based on the weight data, as described herein.

In some embodiments, the at least one communication (e.g., from wearable heart monitoring device 1400 to the remote server) may include at least one further ECG signal portion associated with the at least one arrhythmia (and/or atrial fibrillation) event, as described herein. The remote server may be further configured to receive the communication including the further ECG signal portion(s) and/or receive further annotation data associated with the further ECG signal portion(s) from at least one annotator of the plurality of annotators, as described herein.

In some embodiments, the remote server may be further configured to compare the further annotation data to the arrhythmia (and/or atrial fibrillation) event(s) detected based on the arrhythmia (and/or atrial fibrillation) classifier and/or determine an updated weight for each respective annotator of the at least one annotator based on comparing the further annotation data to the arrhythmia (and/or atrial fibrillation) event(s), as described herein.

In some embodiments, the remote server may be further configured to retrain the arrhythmia (and/or atrial fibrillation) classifier based on the further ECG signal portion(s), the further annotation data, and/or the updated weight data, as described herein.

In some embodiments, the remote computer system may be further configured to compare the further annotation data to the arrhythmia (and/or atrial fibrillation) event(s) detected based on the arrhythmia (and/or atrial fibrillation) classifier and/or transmit at least one further communication based on comparing the further annotation data to the arrhythmia (and/or atrial fibrillation) event(s), as described herein. For example, the at least one further communication may include at least one of a recommendation to retest one or more of the at least one annotator, a recommendation to increase the respective skill score of one or more of the at least one annotator, a recommendation to decrease the respective skill score of one or more of the at least one annotator, any combination thereof, and/or the like.

In some embodiments, the remote computer system may be further configured to retrain the arrhythmia (and/or atrial fibrillation) classifier based on the at least one further ECG signal portion, the further annotation data, and the weight data, as described herein.

In some embodiments, the remote computer system may be configured to receive at least one updated skill score comprising a respective updated skill score for each of at least one annotator of the plurality of annotators, as described herein. Additionally or alternatively, the remote computer system may be configured to determine a respective updated weight for each of the annotator(s) based on the updated skill score(s), as described herein. Additionally or alternatively, the remote computer system may be configured to retrain the arrhythmia (and/or atrial fibrillation) classifier based on the respective updated weight for each of the annotator(s), as described herein.

In some embodiments, training the arrhythmia (and/or atrial fibrillation) classifier may include adjusting a hyperparameter of a loss function of the arrhythmia (and/or atrial fibrillation) classifier based on the weight data, as described herein.

In some embodiments, training the arrhythmia (and/or atrial fibrillation) classifier may include adjusting the respective weight for each of at least one annotator of the plurality of annotators based on a hyperparameter tuning process, as described herein. For example, the respective weight for each annotator may be treated as a hyperparameter, and the initial value of the hyperparameter may be the initial weight determined based on the initial skill score (e.g., based on the initial test given to the respective annotator). The arrhythmia (and/or atrial fibrillation) classifier may be trained based on a training subset (e.g., a first subset of the historical collection of ECG signal portions, as described herein) and the initial value of the hyperparameter (e.g., the initial weights), and a metric (e.g., accuracy, loss, area under curve, precision, recall, F1 score, and/or the like) associated with the initial value of the hyperparameter may be determined based on a validation set (e.g., a second subset of the historical collection of ECG signal portions, as described herein). The value of the hyperparameter may be adjusted (e.g., within a search space, within a range around the initial value, within a range around the initial skill score, randomly, and/or the like), and the arrhythmia (and/or atrial fibrillation) classifier may be retrained based on the training subset and the adjusted value of the hyperparameter so that the metric associated with the adjusted value of the hyperparameter may be determined based on the validation set. The adjustment of the value of the hyperparameter, retraining of the arrhythmia (and/or atrial fibrillation) classifier, and determination of the metric associated with the adjusted value of the hyperparameter may be iteratively repeated until a value of the hyperparameter that optimizes the metric (e.g., increases and/or maximizes accuracy, reduces and/or minimizes loss, and/or the like over the validation set) is found (and/or until a maximum number of iterations is reached). The arrhythmia (and/or atrial fibrillation) classifier trained based on the optimized value of the hyperparameter may be considered to be the trained classifier (e.g., for communicating to and/or installing on the wearable heart monitoring device 1400).

Figure 15B:
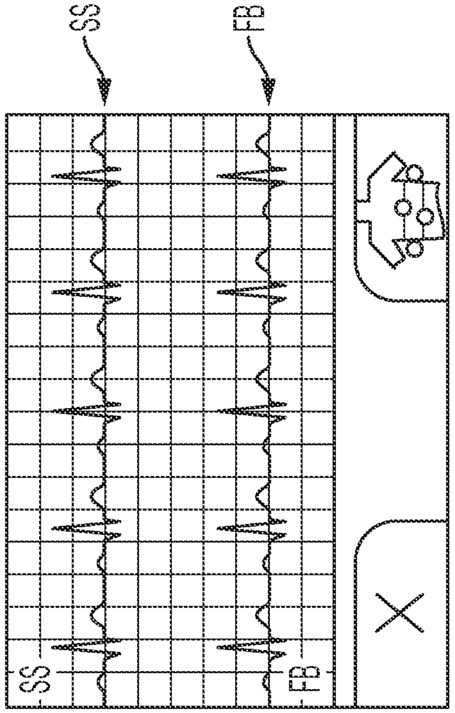
FIGS. 15A-15E illustrate example atypical ECG lead placement, according to some embodiments.
Figure 15A:
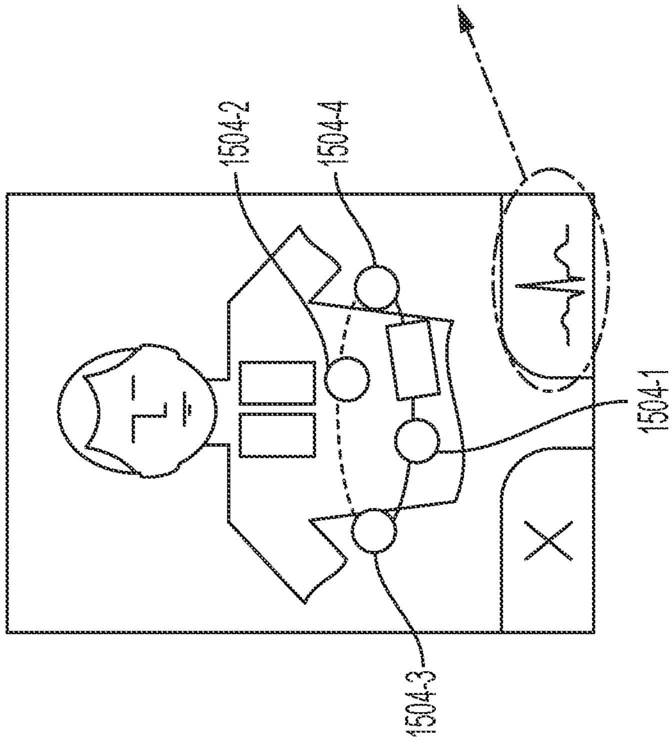
Figure 15D:
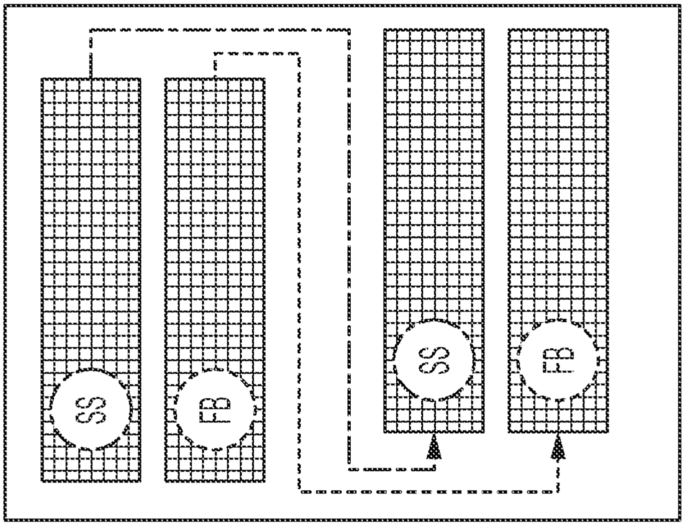
Figure 15C:
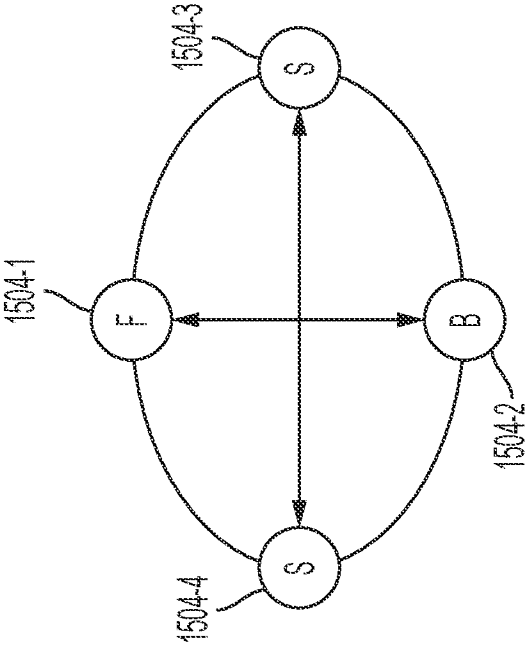
Figure 15E:
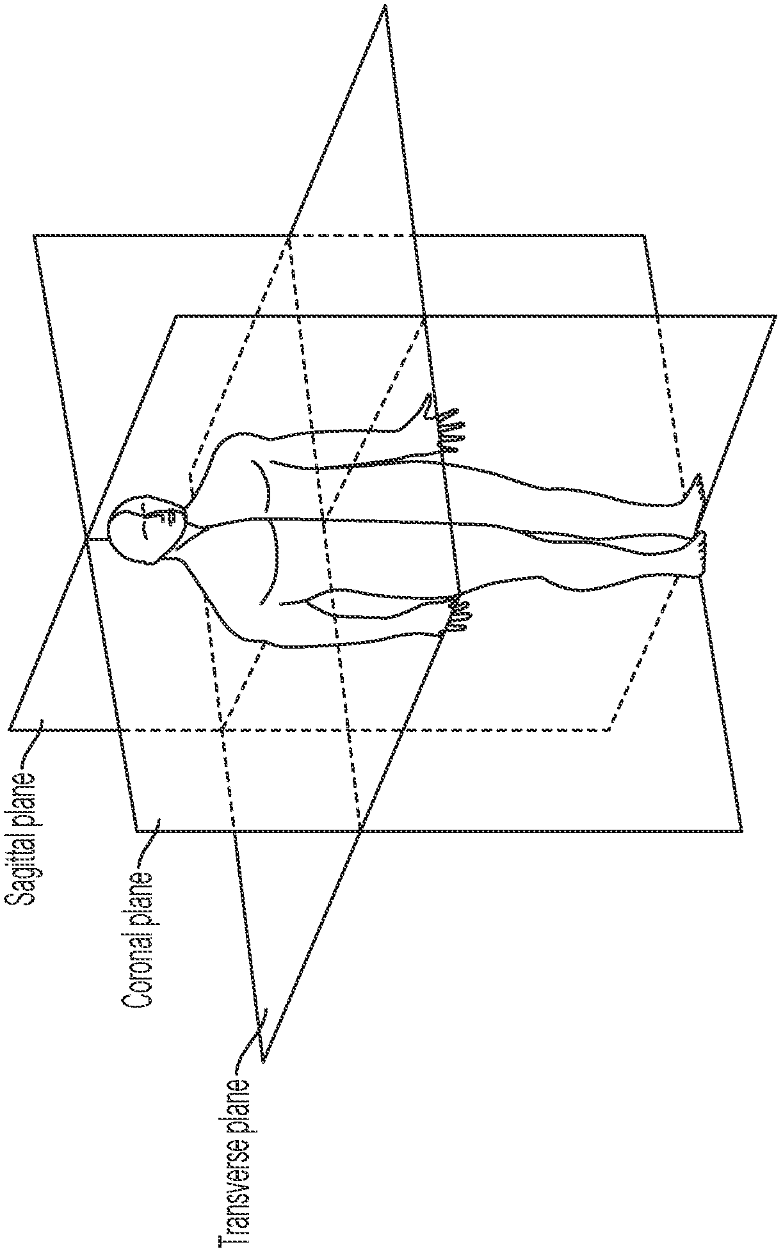

In some embodiments, atypical ECG signals may be used (e.g., as described in further detail below). For example, the atypical ECG leads may be based on ECG electrodes disposed on atypical (e.g., nonstandard) locations of the patient's body. For example, atypical ECG signals may include one or two ECG channels, as described herein. For the purpose of illustration and not limitation, referring to FIGS. 15A-15D, there are shown at least four ECG electrodes 1504-1, 1504-2, 1504-3, 1504-4 (collectively "ECG electrodes 1504"), which may be disposed on the sides of the patient's body and on an anterior and posterior position of the patient's body. The ECG electrodes 1504 may be located over the rib cage, just under the breast area. For example, the ECG electrodes may be positioned circumferentially at the level of the xiphoid process. In some embodiments, the ECG electrodes 1504 may be circumferentially placed along a transverse plane (e.g., as shown in FIG. 15E) at the level of the xiphoid process. The left-side ECG electrode 1504-4 and right-side ECG electrode 1504-3 may be positioned on the midaxillary line (e.g., left-side ECG electrode 1504-4 and right-side ECG electrode 1504-3 may each be labeled as side or S). The anterior (e.g., front or F) ECG electrode 1504-1 may be positioned right of the sternum in the mid-clavicular line. The posterior (e.g., back or B) electrode may be positioned between about 4 cm to about 12 cm left of the center of the spine, more particularly between about 6 cm to about 10 cm left of the center of the spine, and more particularly about 8 cm left of the center of the spine. Accordingly, two atypical ECG channels can include a side-side (SS) ECG channel and a front-back (FB) ECG channel (e.g., as shown in FIGS. 15B and 15D). Referring to FIG. 15C, in some embodiments, the four ECG electrodes 1504 may be configured as two ECG leads that project onto a transverse plane an angle that is substantially orthogonal. In some embodiments, the four ECG electrodes 1504 may be configured as two ECG leads that project onto a transverse plane an angle of between 50 and 150 degrees. For example, a first lead may extend from a first geometrical center of a first one of the first pair of ECG electrodes to a second geometrical center of a second pair of ECG electrodes. The second lead may extend from a third geometrical center of a first one of the second pair of ECG electrodes to a fourth geometrical center of a second one of the second pair of ECG electrodes. As such, projections of the first and second leads onto a transverse plane of the patient may include a substantially orthogonal angle. In some embodiments, projections of the first and second leads onto a coronal plane (e.g., as shown in FIG. 15E) of the patient may include a substantially orthogonal angle. Together, the two ECG leads (e.g., ECG channels) may provide atypical ECG signals, as described herein.

Figure 16A:
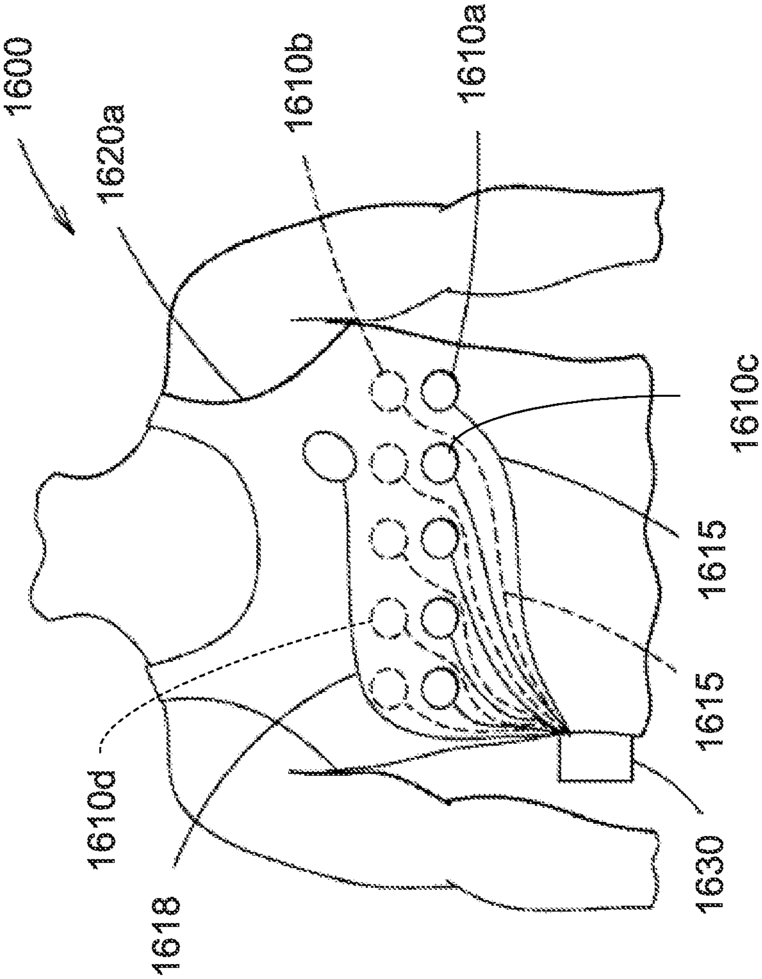
FIGS. 16A and 16B illustrate example atypical ECG lead placement, according to some embodiments.
Figure 16B:
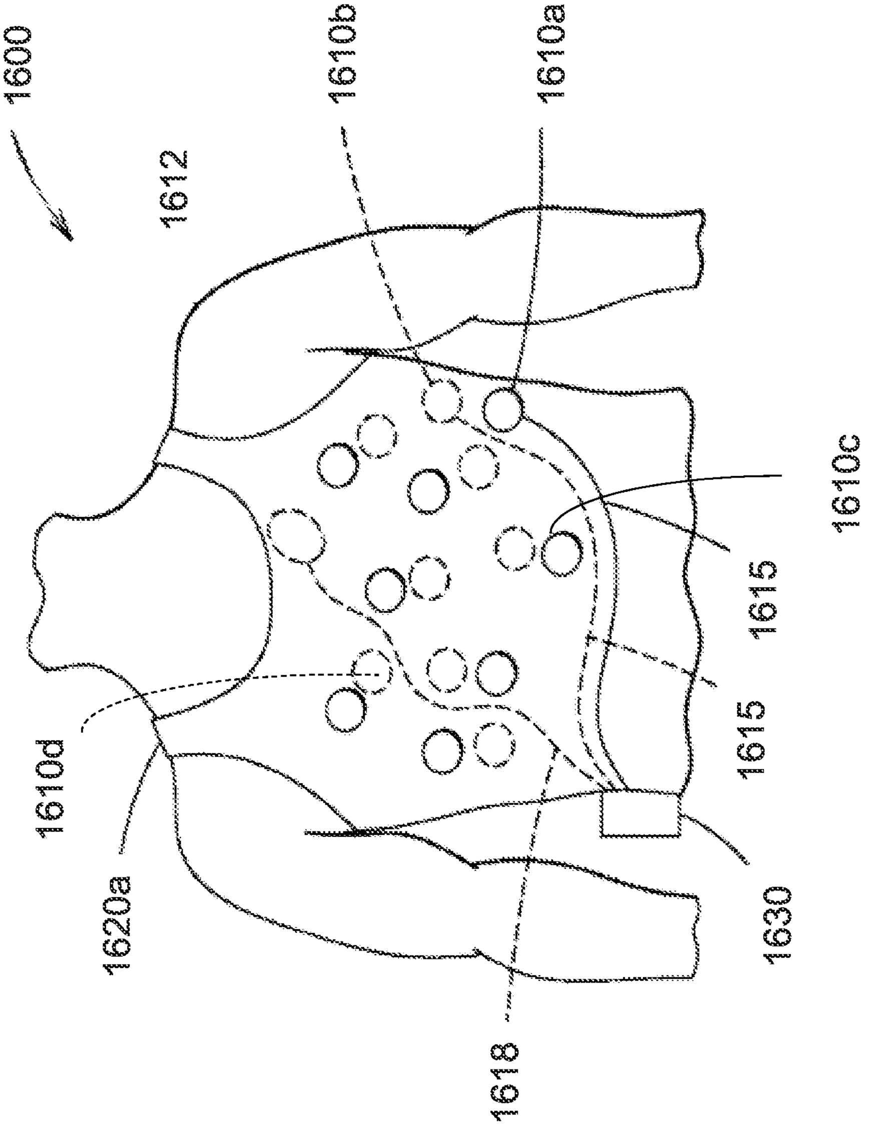

Referring to FIGS. 16A and 16B, in some implementations, an atypical ECG electrode system 1600 may not be coplanar, and each ECG electrode be located on different transverse planar locations on the torso of the patient. For example, as shown, there may be a plurality of ECG electrodes 1610 disposed within a garment 1620*a* on the patient's torso at various anatomical locations, e.g., 1610*a*, 1610*b*, 1610*c*, 1610*d*, and so on. Each of the ECG electrodes 1610 may be connected via cables or wires 1615, 1618 that are disposed in the garment 1620*a* and coupled to a controller 1630. For example, the cables or wires 1615, 1618 may be sewn into the garment, or otherwise permanently integrated into the garment.

In some embodiments, two or more atypical ECG channels may be provided based on dynamically pairing at least two ECG electrodes selected from the plurality of ECG electrodes disposed on the patient's torso. For example, a first ECG electrode 1610*a* may be dynamically paired with a second ECG electrode 1610*b* to form a first ECG channel, and a third ECG electrode 1610*c* may be dynamically paired with a fourth ECG electrode 1610*d* to form a second ECG channel. In some embodiments, the dynamic pairing may be based on a software atypical ECG lead selection process, for example, where a best set of ECG channels may be automatically determined during live monitoring of the patient's ECG based on the patient's current activity status, body posture, time of day, noise detected on the ECG channels, and/or other factors.

In some embodiments, three or more atypical ECG channels may be provided based on dynamically pairing at least four ECG electrodes. For example, a first side ECG electrode may be dynamically paired with an anterior ECG electrode to form a first ECG channel, a second side ECG electrode may be dynamically paired with a posterior ECG electrode to form a second ECG channel, a first side ECG electrode may be dynamically paired with a second side ECG electrode to form a third ECG channel, and an anterior ECG electrode may be dynamically paired with a posterior ECG electrode to form a fourth channel. In some embodiments, the dynamic pairing may be based on a software atypical ECG lead selection process, for example, where a best set of ECG channels may be automatically determined during live monitoring of the patient's ECG based on the patient's current activity status, body posture, time of day, noise detected on the ECG channels, and/or other factors.

In some embodiments, the atypical ECG signals may be from a single ECG channel based on a single pair of ECG electrodes. For example, two ECG electrodes may be disposed on a common patch adhesive backing configured to be attached to the side of the patient's body or on an upper anterior torso location of the patient's body (e.g., as shown in FIGS. 1C, 1D, and 8-10C, further described below). In some embodiments, the device (e.g., the patch) may be configured to be placed on the upper left chest, just below the collarbone. In some embodiments, the device (e.g., the patch) may be configured to be placed on a side location, for example, below the left armpit with the nipple aligned between the top and middle of the device. In such example atypical positions, applicants have performed clinical testing that demonstrated the ability of the atypical ECG signals as capturing P waves, QRS complexes, PR duration, QRS duration, and RR interval. For example, during a study, 43 volunteers (22 females, 21 males) wore an atypical ECG lead patch-based device (e.g., as described herein) and a standard lead-II device simultaneously in sitting, supine, and standing positions. There were no adverse effects of complications during the study. The study demonstrated that atypical ECG lead patch based device captured P waves, QRS complexes, PR duration, QRS duration, and RR interval aspects of the ECG waveform. In some embodiments, the adhesive patch may be disposable, made of biocompatible, non-woven material, and/or designed for application to skin according to expected use. In some embodiments, the atypical ECG lead patch-based device (e.g., as described herein) may consist of a plastic frame for the device attachment and two ECG electrodes embedded on each side of the patch. Attachment of the atypical ECG lead device to the adhesive patch may be performed using a latch mechanism, so the user may be able to autonomously perform the removal of the electronic sensor from the patch.

In some embodiments, the systems, techniques, and methods described herein may include a plurality of ECG electrodes and associated circuitry configured to provide at least one standard ECG channel producing at least one standard ECG signal for the patient and at least one atypical ECG channel producing at least one atypical ECG signal for the patient. For example, a cardiac monitoring and/or treatment device may be based on at least two ECG electrodes positioned at a right arm (RA) location and a left arm (LA) location to provide a lead I channel, and at least two additional ECG electrodes disposed on a common patch adhesive backing configured to be attached to the side of the patient's body or on an upper anterior torso location of the patient's body (e.g., similar to the patch configuration shown in FIGS. 1C, 1D, and 9A-E).

In some embodiments, the systems, techniques, and methods described herein include plurality of ECG electrodes and associated circuitry configured to provide at least one of a standard ECG channel producing at least one standard ECG signal for the patient or at least one atypical ECG channel producing at least one atypical ECG signal for the patient.

Accordingly, this disclosure also relates to systems, methods, and computer program products for cardiac diagnosis and/or monitoring with atypical electrocardiogram (ECG) signals. For example, one or more trained classifier(s), each of which including at least one neural network, may be used by an atypical ECG lead heart monitoring device such as those described above and described in further detail below (e.g., external, wearable, and/or the like heart monitoring device), a computer system, and/or the like to detect (e.g., identify and/or the like) a cardiac event (e.g., arrhythmia event, atrial fibrillation event, and/or the like) based on one or more atypical ECG signals of one or more atypical ECG channels derived from the atypical ECG lead heart monitoring device. Example use scenarios of the present devices, systems, techniques and methods include use of the systems, methods, and computer program products for cardiac diagnosis and/or monitoring in the context of atypical ECG lead arrhythmia monitoring systems, heart failure management systems, mobile cardiac telemetry systems, continuous event monitoring systems, cardiac holter monitoring systems (including extended cardiac holter monitoring), wearable cardiac monitors, wearable defibrillators, wearable cardioverter defibrillators, and other such ambulatory cardiac monitoring and/or treatment systems. Benefits of the devices, systems, methods, and techniques described herein include the ability to apply machine learning and deep learning techniques, as described herein, to the atypical ECG lead data from the devices as described herein. In examples, the training methodology for atypical ECG lead data relies on accurate or substantially accurate labeling of the training ECG data. Where atypical ECG leads are involved, human-based ECG interpretation for arrhythmia events such as atrial fibrillation, or ectopic beats may range based on the degree of skill, training, background knowledge, error rates, and/or reliability of the interpreting ECG technicians. In accordance with the principles described herein, devices, systems, methods, and techniques are disclosed that provide machine learning and deep learning techniques for assessing for arrhythmia events, including atrial fibrillation events, based on weights assigned to the labeled (e.g., annotated) training ECG data (e.g., ECG signal portions) to account for variable reliability in the training ECG data.

For example, some patients may include heart failure patients, e.g., congestive heart failure (CHF) patients. CHF is a condition in which the heart's function as a pump is inadequate to meet the body's needs. Generally, many disease processes may impair the pumping efficiency of the heart to cause congestive heart failure. The symptoms of congestive heart failure vary, but may include fatigue, diminished exercise capacity, shortness of breath, and swelling (edema). The diagnosis of congestive heart failure may be based on knowledge of the individual's medical history, a careful physical examination, and selected laboratory tests.

Additionally or alternatively, patients may suffer from cardiac arrhythmias. One of the most deadly cardiac arrhythmias is ventricular fibrillation. Additionally, atrial fibrillation is one of the most common types of arrhythmias, and atrial fibrillation contributes to hundreds of thousands of deaths each year and afflicts millions of patients. Fibrillation occurs when normal, regular electrical impulses are replaced by irregular and rapid impulses, causing the heart muscle to stop normal contractions and to begin to quiver. Normal blood flow ceases, and organ damage or death may result in minutes if normal heart contractions are not restored. Because the victim has no perceptible warning of the impending fibrillation, death often occurs before the necessary medical assistance can arrive. Other cardiac arrhythmias may include excessively slow heart rates, known as bradycardia, or excessively fast heart rates, known as tachycardia. Cardiac arrest may occur in a patient, for example, when various arrhythmias of the heart, such as atrial fibrillation, ventricular fibrillation, tachycardia, bradycardia, pulseless electrical activity (PEA), asystole (heart stops all electrical activity), and/or other arrhythmias, result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Fibrillation and/or tachycardia may be treated by an implanted or external defibrillator, e.g., by providing a therapeutic shock to the heart in an attempt to restore normal rhythm. To treat conditions such as bradycardia, an implanted or external pacing device may provide pacing stimuli to the patient's heart until intrinsic cardiac electrical activity returns. External pacemakers, defibrillators, and other medical monitors designed for ambulatory and/or long-term use have further improved the ability to timely detect and treat life-threatening conditions.

Accordingly, this disclosure also relates to systems, methods, and computer program products for cardiac diagnosis and/or monitoring with atypical electrocardiogram (ECG) signals. For example, a wearable atypical ECG lead arrhythmia monitoring system for identifying arrhythmias experienced by a patient may include an external wearable heart monitoring device configured for continuous and long-term monitoring of a patient. Such an external wearable heart monitoring device may include a plurality of ECG electrodes and associated circuitry configured to sense surface ECG activity of the patient. For example, each ECG electrode may be configured to be anatomically located within a circumferential atypical zone of the patient's torso in an uninhibiting manner so as to allow for the patient to be ambulatory. The ECG electrodes and associated circuitry may be configured to provide at least one atypical ECG channel producing at least one atypical ECG signal for the patient. Such atypical (e.g., non-standard, uncommon, and/or the like) ECG signal(s) may allow (e.g., be suitable for) machine detection (e.g., detection by a machine learning model, such as a classifier, a neural network, and/or the like) of an arrhythmia, even though human reviewers (e.g., annotators and/or the like) may face difficulty in identifying arrhythmias based on such atypical ECG signal(s) (e.g., due to unfamiliarity, lack of experience, lack of training, difficulty in visually perceiving certain waves, and/or the like with atypical ECG signal(s)). To address the potential inconsistency, inaccuracy, imprecision, disagreement, and/or the like among different annotators, a non-transitory computer-readable medium may include an arrhythmia classifier including at least one neural network trained based on both a historical collection of a plurality of atypical ECG signal portions with annotation data and weight data for the annotation. For example, the annotation data may include at least one respective annotation for each respective atypical ECG signal portion of the plurality of atypical ECG signal portions, and the weight data may include a respective weight for each respective annotation based on a respective annotator of the respective annotation (e.g., based on a respective skill level, skill score, and/or the like of the annotator). An arrhythmia classifier trained in this manner may be used to accurately detect the arrhythmia event(s) in the atypical ECG signal(s), for example, because the arrhythmia classifier was trained based on atypical ECG signal portion(s) (e.g., rather than standard ECG signals) while reducing (e.g., eliminating, decreasing, and/or the like) the potential inaccuracy, bias, lack of precision, and/or other difficulty from the different annotators (e.g., of different levels of skill) by weighting the annotations from each annotator. The external wearable heart monitoring device may, therefore, include one or more processors operatively connected to the at least one atypical ECG channel and the non-transitory computer-readable medium, and the processor(s) may receive the atypical ECG signal(s) of the atypical ECG channel(s) and monitor the atypical ECG signal(s) to detect at least one arrhythmia event based on the arrhythmia classifier. For example, arrhythmia events include bradycardia, tachycardia, bigeminy, atrial fibrillation, ventricular tachycardia, supraventricular tachycardia, 2nd degree AV block, 3rd degree AV block and pauses. In some embodiments, a pause arrhythmia event may be based on QRS detection. Accordingly, an RR interval longer than a configurable threshold may be deemed a pause arrhythmia event. Verified interval are declared as a pause. For example, a default threshold can be 3 seconds, 5 seconds, or 10 seconds. A physician, prescriber, or other authorized person may modify the default to a certain threshold. In some embodiments, arrhythmia events may include detection based on ectopic beats. Ectopic beats detected by the devices as disclosed herein may include ventricular ectopic beats (VEB), ventricular couplets, ventricular runs, and supraventricular ectopic beat (SVEB). Additionally, the processor(s) may transmit one or more communications based on the arrhythmia event(s), for example, to a remote computer system. For example, if communication is limited to when an arrhythmia is detected, resources (e.g., bandwidth, communication network resources, power resources, memory resources, and/or the like) may be preserved while still ensuring vital ECG signal information (e.g., atypical ECG signal portions including arrhythmia events and/or alerts based thereof) are communicated.

In some embodiments, the ECG electrodes may include at least four ECG electrodes. For example, the atypical ECG channel(s) may include at least two atypical ECG channels, and each atypical ECG channel may be associated with two respective ECG electrodes. In some embodiments, the ECG electrodes may include a front ECG electrode, a back ECG electrode, a first side ECG electrode, and a second side ECG electrode. Additionally or alternatively, the atypical ECG channel(s) may include a front-to-back (FB) ECG channel (e.g., associated with the front ECG electrode and the back ECG electrode) and/or a side-to-side (SS) ECG channel (e.g., associated with the first side ECG electrode and the second side ECG electrode). In some embodiments, the atypical ECG channel(s) may include a first atypical ECG channel (e.g., a FB ECG channel) and a second atypical ECG channel (e.g., an SS ECG channel) substantially orthogonal to the first atypical ECG channel. In some embodiments, the atypical ECG channel(s) may include at least three atypical ECG channels, at least four atypical ECG channels, etc.

In some embodiments, the atypical ECG channel(s) may include at least one dynamically defined atypical ECG channel. For example, the associated circuitry of the ECG electrodes may analyze surface ECG activity of the patient and select at least two of the ECG electrodes to define the at least one dynamically defined atypical ECG channel.

In some embodiments, the external wearable heart monitoring device may include a garment configured to be worn about a torso of the patient for an extended period of time and further configured to house the plurality of ECG electrodes. For example, the garment may include a plurality of receptacles configured to receive the ECG electrodes. In some embodiments, the external wearable heart monitoring device may include a plurality of therapy electrodes configured to be housed in the garment. For example, the external wearable heart monitoring device may determine whether the patient is experiencing a treatable cardiac arrhythmia and/or deliver one or more therapeutic shocks to the patient via the therapy electrodes upon determining that the patient is experiencing a (treatable) cardiac arrhythmia.

In some embodiments, the respective weight for each respective annotator may be based on a respective skill level of the respective annotator. For example, the respective skill level for each respective annotator may include a skill score (e.g., an integer value from one to four; an integer value from one to five; an integer value from one to ten; an integer value from one to 100; a value from zero to one; one of 25, 50, 75, or 100; and/or the like).

In some embodiments, the remote computer system may receive a plurality of skill scores comprising a respective skill score for each respective annotator and/or may determine the respective weight for each respective annotator based on the plurality of scores. In some embodiments, the remote computer system may receive the historical collection of the atypical ECG signal portions with the annotation data and/or may train the arrhythmia classifier based on the historical collection of the atypical ECG signal portions with the annotation data and based on the weight data.

In some embodiments, the communication(s) (e.g., from the external wearable heart monitoring device) may include at least one further atypical ECG signal portion associated with the at least one arrhythmia event. The remote computer system may receive the communication(s). Additionally, the remote computer system may receive further annotation data associated with the further atypical ECG signal portion(s) from at least one annotator. In some embodiments, the remote computer system may compare the further annotation data to the arrhythmia event(s) detected based on the arrhythmia classifier. In some embodiments, the remote computer system may determine an updated weight for each respective annotator of the at least one annotator based on comparing the further annotation data to the at least one arrhythmia event. Additionally or alternatively, the remote computer system may retrain the arrhythmia classifier based on the further atypical ECG signal portion(s), the further annotation data, and/or the updated weight data. Additionally or alternatively, the remote computer system may transmit at least one further communication, for example, based on comparing the further annotation data to the at least one arrhythmia event. For example, the at least one further communication may include at least one of a recommendation to retest one or more of the annotator(s), a recommendation to increase the respective skill score of one or more of the annotator(s), a recommendation to decrease the respective skill score of one or more of the annotator(s), any combination thereof, and/or the like.

In some embodiments, the remote computer system may retrain the arrhythmia classifier based on the further atypical ECG signal portion(s), the further annotation data, and/or the weight data.

In some embodiments, the remote computer system may receive at least one updated skill score comprising a respective updated skill score for each of at least one annotator (e.g., of the plurality of annotators). The remote computer system may determine a respective updated weight for each of the annotator(s) based on the updated skill score(s). In some embodiments, the remote computer system may retrain the arrhythmia classifier based on the respective updated weight for each of the at least one annotator.

In some embodiments, training (or retraining) the arrhythmia classifier may include adjusting a hyperparameter of a loss function of the arrhythmia classifier based on the weight data.

Embodiments of the current disclosure include a wearable atypical ECG lead arrhythmia monitoring system for identifying arrhythmias experienced by a patient, which may include an external wearable heart monitoring device configured for continuous and long-term monitoring of a patient. Such an external wearable heart monitoring device may include a plurality of ECG electrodes and associated circuitry configured to sense surface ECG activity of the patient, and each ECG electrode may be configured to be anatomically located on the patient's thorax superior to the patient's xiphoid process and lateral to the patient's sternum, in an uninhibiting manner so as to allow for the patient to be ambulatory. The ECG electrodes and associated circuitry may be configured to provide at least one atypical ECG channel producing at least one atypical ECG signal for the patient. Such atypical (e.g., non-standard, uncommon, and/or the like) ECG signal(s) may allow (e.g., be suitable for) machine detection (e.g., detection by a machine learning model, such as a classifier, a neural network, and/or the like) of an arrhythmia, even though human reviewers (e.g., annotators and/or the like) may face difficulty in identifying arrhythmias based on such atypical ECG signal(s) (e.g., due to unfamiliarity, lack of experience, lack of training, difficulty in visually perceiving certain waves, and/or the like with atypical ECG signal(s)). To address the potential inconsistency, inaccuracy, imprecision, disagreement, and/or the like among different annotators, a non-transitory computer-readable medium may include an arrhythmia classifier including at least one neural network trained based on both a historical collection of a plurality of atypical ECG signal portions with annotation data and weight data for the annotation. For example, the annotation data may include at least one respective annotation for each respective atypical ECG signal portion of the plurality of atypical ECG signal portions, and the weight data may include a respective weight for each respective annotation based on a respective annotator of the respective annotation (e.g., based on a respective skill level, skill score, and/or the like of the annotator). An arrhythmia classifier trained in this manner may be used to accurately detect the arrhythmia event(s) in the atypical ECG signal(s), for example, because the arrhythmia classifier was trained based on atypical ECG signal portion(s) (e.g., rather than standard ECG signals) while reducing (e.g., eliminating, decreasing, and/or the like) the potential inaccuracy, bias, lack of precision, and/or other difficulty from the different annotators (e.g., of different levels of skill) by weighting the annotations from each annotator. The external wearable heart monitoring device may, therefore, include one or more processors operatively connected to the at least one atypical ECG channel and the non-transitory computer-readable medium, and the processor(s) may receive the atypical ECG signal(s) of the atypical ECG channel(s) and monitor the atypical ECG signal(s) to detect at least one arrhythmia event based on the arrhythmia classifier. Additionally, the processor(s) may transmit one or more communications based on the arrhythmia event(s), for example, to a remote computer system. For example, if communication is limited to when an arrhythmia is detected, resources (e.g., bandwidth, communication network resources, power resources, memory resources, and/or the like) may be preserved while still ensuring vital ECG signal information (e.g., atypical ECG signal portions including arrhythmia events and/or alerts based thereof) are communicated.

In some embodiments, at least two ECG electrodes may be disposed within a predetermined distance on the patient's thorax superior to the patient's xiphoid process and lateral to the patient's sternum. For example, the predetermined distance may include 15 centimeters, and/or the ECG electrodes may be spaced less than 15 centimeters (e.g., less than 10 centimeters, 5-15 centimeters, less than 5 centimeters, and/or the like).

In some embodiments, the external wearable heart monitoring device may include a single adhesive patch.

In some embodiments, the ECG electrodes may be all on one side of the patient's sternum. In some embodiments, at least some (e.g., all) of the ECG electrodes may be left lateral to the patient's sternum. In some embodiments, at least some (e.g., all) of the ECG electrodes may be right lateral to the patient's sternum.

In some embodiments, the external wearable heart monitoring device may include a patch configured to be worn by the patient for an extended period of time. For example, the patch may be configured to be worn (e.g., continuously adhesively coupled to the skin of the patient) for at least one of: 3-5 days, 5-7 days, 7-10 days, 10-14 days, 14-30 days, and/or the like. In some embodiments, the patch may include the plurality of ECG electrodes. In some embodiments, the patch may be configured to be adhesively coupled to skin of the patient (e.g., an adhesive patch). In some embodiments, the adhesive patch may be disposable. In some embodiments, the external wearable heart monitoring device may further include a cardiac monitoring unit configured to be removably attached to the patch. For example, the cardiac monitoring unit may be configured to record the surface ECG activity of the patient sensed by the plurality of ECG electrodes and associated circuitry.

Embodiments of the current disclosure include an atypical ECG lead arrhythmia classification system. Such an atypical ECG lead arrhythmia classification system may include a non-transitory computer-readable medium including an arrhythmia classifier, which may include at least one neural network. At least one processor may be operatively connected to the non-transitory computer-readable medium. The processor(s) may receive a plurality of scores comprising a respective score for each respective annotator of a plurality of annotators and/or may determine a respective initial weight for each respective annotator of the plurality of annotators based on the plurality of scores. Additionally, the processor(s) may receive a historical collection of a plurality of atypical ECG signal portions with annotation data. For example, the annotation data may include at least one respective annotation for each respective atypical ECG signal portion of the plurality of atypical ECG signal portions. The processor(s) may train the arrhythmia classifier based on the historical collection of the plurality of atypical ECG signal portions with the annotation data and based on weight data for the annotation data of the plurality of atypical ECG signal portions. For example, the weight data may include and/or may be based on the respective initial weight for the respective annotator of each respective annotation. An arrhythmia classifier trained in this manner may be used to accurately detect arrhythmia event(s) in atypical ECG signal(s), for example, because the arrhythmia classifier was trained based on atypical ECG signal portion(s) (e.g., rather than standard ECG signals) while reducing (e.g., eliminating, decreasing, and/or the like) the potential inaccuracy, bias, lack of precision, and/or other difficulty from the different annotators (e.g., of different levels of skill) by weighting the annotations from each annotator.

In some embodiments, the processor(s) may receive at least one further atypical ECG signal portion with further annotation data from at least one annotator of the plurality of annotators. The processor(s) may analyze the at least one further atypical ECG signal portion to detect at least one arrhythmia event based on the arrhythmia classifier. The processor(s) may compare the further annotation data to the at least one arrhythmia event. The processor(s) may transmit at least one communication based on comparing the further annotation data to the at least one arrhythmia event. As such, the arrhythmia classifier may enable accurate determination of whether an annotator correctly identified and/or annotated an arrhythmia in the (further) atypical ECG signal portion.

In some embodiments, the processor(s) may retrain the arrhythmia classifier based on the at least one further atypical ECG signal portion, the further annotation data, and the initial weight data. In some embodiments, the processor(s)

may determine an updated weight for at least one annotator based on comparing the further annotation data to the at least one arrhythmia event. Additionally or alternatively, the processor(s) may retrain the arrhythmia classifier based on the at least one further atypical ECG signal portion, the further annotation data, the updated weight data, and/or any combination thereof. As such, the arrhythmia classifier may be improved (e.g., constantly improved, periodically improved, and/or the like) based on retraining.

In some embodiments, the communication(s) may include at least one of a recommendation to retest one or more of the annotator(s), a recommendation to increase the respective skill score of one or more of the annotator(s), a recommendation to decrease the respective skill score of one or more of the annotator(s), any combination thereof, and/or the like. In some embodiments, the processor(s) may receive at least one updated skill score comprising a respective updated skill score for each of at least one annotator of the plurality of annotators. The processors may determine a respective updated weight for each of the at least one annotator based on the at least one updated skill score, and/or the processors may retrain the arrhythmia classifier based on the respective updated weight for each of the at least one annotator. As such, the annotators may be reevaluated (e.g., constantly reevaluated, periodically reevaluated, and/or the like), and, therefore, the arrhythmia classifier trained based on the weights associated with the individual annotators also may be improved accordingly.

Embodiments of the current disclosure include a wearable atypical ECG lead atrial fibrillation monitoring system for identifying atrial fibrillation experienced by a patient, which may include an external wearable heart monitoring device configured for continuous and long-term monitoring of a patient. Such an external wearable heart monitoring device may include a plurality of ECG electrodes and associated circuitry configured to sense surface ECG activity of the patient. For example, each ECG electrode may be configured to be anatomically located within a circumferential atypical zone of the patient's torso in an uninhibiting manner so as to allow for the patient to be ambulatory. The ECG electrodes and associated circuitry may be configured to provide at least one atypical ECG channel producing at least one atypical ECG signal for the patient. Such atypical (e.g., non-standard, uncommon, and/or the like) ECG signal(s) may allow (e.g., be suitable for) machine detection (e.g., detection by a machine learning model, such as a classifier, a neural network, and/or the like) of an atrial fibrillation, even though human reviewers (e.g., annotators and/or the like) may face difficulty in identifying atrial fibrillations based on such atypical ECG signal(s) (e.g., due to unfamiliarity, lack of experience, lack of training, difficulty in visually perceiving certain waves, and/or the like with atypical ECG signal(s)). To address the potential inconsistency, inaccuracy, imprecision, disagreement, and/or the like among different annotators, a non-transitory computer-readable medium may include an atrial fibrillation classifier including at least one neural network trained based on both a historical collection of a plurality of atypical ECG signal portions with annotation data and weight data for the annotation. For example, the annotation data may include at least one respective annotation for each respective atypical ECG signal portion of the plurality of atypical ECG signal portions, and the weight data may include a respective weight for each respective annotation based on a respective annotator of the respective annotation (e.g., based on a respective skill level, skill score, and/or the like of the annotator). An atrial fibrillation classifier trained in this manner may be used to accurately detecting the atrial fibrillation event(s) in the atypical ECG signal(s), for example, because the atrial fibrillation classifier was trained based on atypical ECG signal portion(s) (e.g., rather than standard ECG signals) while reducing (e.g., eliminating, decreasing, and/or the like) the potential inaccuracy, bias, lack of precision, and/or other difficulty from the different annotators (e.g., of different levels of skill) by weighting the annotations from each annotator. The external wearable heart monitoring device may, therefore, include one or more processors operatively connected to the at least one atypical ECG channel and the non-transitory computer-readable medium, and the processor(s) may receive the atypical ECG signal(s) of the atypical ECG channel(s) and monitor the atypical ECG signal(s) to detect at least one atrial fibrillation event based on the atrial fibrillation classifier. Additionally, the processor(s) may transmit one or more communications based on the atrial fibrillation event(s), for example, to a remote computer system. For example, if communication is limited to when an atrial fibrillation is detected, resources (e.g., bandwidth, communication network resources, power resources, memory resources, and/or the like) may be preserved while still ensuring vital ECG signal information (e.g., atypical ECG signal portions including atrial fibrillation events and/or alerts based thereof) are communicated.

Embodiments of the current disclosure include a wearable atypical ECG lead atrial fibrillation monitoring system for identifying atrial fibrillations experienced by a patient, which may include an external wearable heart monitoring device configured for continuous and long-term monitoring of a patient. Such an external wearable heart monitoring device may include a plurality of ECG electrodes and associated circuitry configured to sense surface ECG activity of the patient, and each ECG electrode may be configured to be anatomically located on the patient's thorax superior to the patient's xiphoid process and lateral to the patient's sternum, in an uninhibiting manner so as to allow for the patient to be ambulatory. The ECG electrodes and associated circuitry are may be configured to provide at least one atypical ECG channel producing at least one atypical ECG signal for the patient. Such atypical (e.g., non-standard, uncommon, and/or the like) ECG signal(s) may allow (e.g., be suitable for) machine detection (e.g., detection by a machine learning model, such as a classifier, a neural network, and/or the like) of an atrial fibrillation, even though human reviewers (e.g., annotators and/or the like) may face difficulty in identifying atrial fibrillations based on such atypical ECG signal(s) (e.g., due to unfamiliarity, lack of experience, lack of training, difficulty in visually perceiving certain waves, and/or the like with atypical ECG signal(s)). To address the potential inconsistency, inaccuracy, imprecision, disagreement, and/or the like among different annotators, a non-transitory computer-readable medium may include an atrial fibrillation classifier including at least one neural network trained based on both a historical collection of a plurality of atypical ECG signal portions with annotation data and weight data for the annotation. For example, the annotation data may include at least one respective annotation for each respective atypical ECG signal portion of the plurality of atypical ECG signal portions, and the weight data may include a respective weight for each respective annotation based on a respective annotator of the respective annotation (e.g., based on a respective skill level, skill score, and/or the like of the annotator). An atrial fibrillation classifier trained in this manner may be used to accurately detect the atrial fibrillation event(s) in the atypical ECG signal(s), for example, because the atrial fibrillation classifier was trained based on atypical ECG signal portion (s) (e.g., rather than standard ECG signals) while reducing (e.g., eliminating, decreasing, and/or the like) the potential inaccuracy, bias, lack of precision, and/or other difficulty from the different annotators (e.g., of different levels of skill) by weighting the annotations from each annotator. The external wearable heart monitoring device may, therefore, include one or more processors operatively connected to the at least one atypical ECG channel and the non-transitory computer-readable medium, and the processor(s) may receive the atypical ECG signal(s) of the atypical ECG channel(s) and monitor the atypical ECG signal(s) to detect at least one atrial fibrillation event based on the atrial fibrillation classifier. Additionally, the processor(s) may transmit one or more communications based on the atrial fibrillation event(s), for example, to a remote computer system. For example, if communication is limited to when an atrial fibrillation is detected, resources (e.g., bandwidth, communication network resources, power resources, memory resources, and/or the like) may be preserved while still ensuring vital ECG signal information (e.g., atypical ECG signal portions including atrial fibrillation events and/or alerts based thereof) are communicated.

Referring now to FIGS. 1A-1F, FIGS. 1A-1F show example block diagrams of a system 100 for cardiac diagnosis and/or monitoring with atypical ECG signals, according to some embodiments. As shown in FIGS. 1A-1F, the system 100 may include a wearable heart monitoring device 102, a remote computer system 140, an annotator device 150, a gateway device 160, and/or a communication network 170.

The wearable heart monitoring device 102 may include one or more devices capable of receiving information from and/or communicating information to the remote computer system 140, the annotator device 150, and/or the gateway device 160 (e.g., directly via wired and/or wireless network, via the communication network 170, and/or any other suitable communication technique). In some embodiments, the wearable heart monitoring device 102 may include at least one ECG electrode. For example, the wearable heart monitoring device 102 may include a plurality of ECG electrodes, such as a first ECG electrode 104-1, a second ECG electrode 104-2, a third ECG electrode 104-3, a fourth second ECG electrode 104-4, and/or the like (collectively "ECG electrodes 104" and individually "ECG electrode 104"). In some embodiments, the wearable heart monitoring device 102 may include at least one controller 106. For example, a controller 106 may include associated circuitry of the plurality of ECG electrodes, as described herein. Additionally or alternatively, a controller 106 may include at least one processor and/or at least one non-transitory computer-readable medium, as described herein. In some embodiments, the controller 106 may include a computing device (e.g., computing device 700 and/or components thereof, as described herein).

In some embodiments, the wearable heart monitoring device 102 may include at least one (e.g., a plurality of) therapy electrode 108, as described herein. For example, the wearable heart monitoring device 102 (e.g., the controller 106 thereof) may determine whether a patient is experiencing a treatable cardiac arrhythmia. If so, the wearable heart monitoring device 102 (e.g., the controller 106 thereof) may deliver one or more therapeutic shocks to the patient via the therapy electrodes 108 upon determining that the patient is experiencing a treatable cardiac arrhythmia, as described herein.

The remote computer system 140 may include one or more devices capable of receiving information from and/or communicating information to the wearable heart monitoring device 102, the annotator device 150, and/or the gateway device 160 (e.g., directly via wired and/or wireless network, via the communication network 170, and/or any other suitable communication technique). In some embodiments, the remote computer system 140 may include at least one computing device, such as a server, a group of servers, and/or other like devices. Additionally or alternatively, the remote computer system 140 may include at least one other computing device separate from or including the server and/or group of servers, such as a portable and/or handheld device (e.g., a computer, a laptop, a personal digital assistant (PDA), a smartphone, a tablet, and/or the like), a desktop computer, and/or other like devices. In some embodiments, the remote computer system 140 may be associated with a cardiac monitoring facility and/or the like, as described herein. For example, the cardiac monitoring facility may be associated with a provider (e.g., manufacturer, distributor, and/or the like) of the wearable heart monitoring device 102, as described herein. In some embodiments, the remote computer system 140 may include at least one processor operatively connected to at least one non-transitory computer readable medium, as described herein. In some embodiments, the remote computer system 140 may be in communication with at least one data storage device, which may be local or remote to the remote computer system 140. In some embodiments, the remote computer system 140 may be capable of receiving information from, storing information in, communicating information to, or searching information stored in the data storage device.

The annotator device 150 may include one or more devices associated with an annotator and capable of receiving information from and/or communicating information to the wearable heart monitoring device 102, the remote computer system 140, and/or the gateway device 160 (e.g., directly via wired and/or wireless network, via the communication network 170, and/or any other suitable communication technique). In some embodiments, the annotator device 150 may include at least one computing device, such as a portable and/or handheld device (e.g., a computer, a laptop, a personal digital assistant (PDA), a smartphone, a tablet, and/or the like), a desktop computer, and/or other like devices, as described herein. In some embodiments, the annotator device 150 may be associated with a cardiac monitoring facility and/or the like, as described herein. In some embodiments, the annotator device 150 may be part of the remote computer system 140. Additionally or alternatively, the annotator device 150 may be local or remote to the remote computer system 140. In some embodiments, the annotator device 150 may include at least one input component that permits the annotator device 150 to receive information, such as via user input (e.g., a touch screen display, a keyboard, a keypad, a mouse, a button, a switch, a microphone, a camera, and/or the like). Additionally or alternatively, the annotator device 150 may include at least one output component that provides output information from the annotator device 150 (e.g., a display, a touch screen, a speaker, and/or the like). In some embodiments, the annotator device 150 may receive communications (e.g., messages, recommendations, alerts, and/or the like) associated with atypical ECG signals and/or portions thereof (e.g., from the remote computer system 140, the wearable heart monitoring device 102, and/or the like), as described herein. In some embodiments, the annotator device 150 may communicate annotation data associated with at least one annotation for a respective atypical ECG signal and/or portion thereof (e.g., to the remote computer system 140, the wearable heart monitoring device 102, and/or the like), as described herein. In some embodiments, annotator device 150 may include a plurality of annotator devices for a plurality of annotators. For example, each annotator may be associated with at least one annotator device 150, and/or each annotator device 150 may be associated with at least one annotator.

The gateway device 160 may include one or more devices capable of receiving information from and/or communicating information to the wearable heart monitoring device 102, the remote computer system 140, and/or the annotator device 150 (e.g., directly via wired and/or wireless network, via the communication network 170, and/or any other suitable communication technique). In some embodiments, the gateway device 160 may include at least one computing device, such as a portable and/or handheld device (e.g., a computer, a laptop, a personal digital assistant (PDA), a smartphone, a tablet, and/or the like), a desktop computer, and/or other like devices, as described herein. In some embodiments, the gateway device 160 may be associated with a patient, e.g., a respective patient associated with (e.g., wearing, connected to, and/or the like) the wearable heart monitoring device 102. In some embodiments, the gateway device 160 may be associated with a cardiac monitoring facility and/or the like, as described herein. In some embodiments, the gateway device 160 may be local or remote to the wearable heart monitoring device 102. Additionally or alternatively, the gateway device 160 may be local or remote to the remote computer system 140. In some embodiments, the gateway device 160 may include at least one input component that permits the gateway device 160 to receive information, such as via user input (e.g., a touch screen display, a keyboard, a keypad, a mouse, a button, a switch, a microphone, a camera, and/or the like). Additionally or alternatively, the gateway device 160 may include at least one output component that provides output information from the gateway device 160 (e.g., a display, a touch screen, a speaker, and/or the like). In some embodiments, the gateway device 160 may receive biometric data (e.g., atypical ECG signals, atypical ECG signal portions, non-ECG biometric data associated with at least one sensor, and/or the like) from the wearable heart monitoring device 102 and/or the like, as described herein. Additionally or alternatively, the gateway device 160 may communicate the biometric data to the remote computer system 140 and/or the like, as described herein. In some embodiments, an arrhythmia classifier (and/or an atrial fibrillation classifier) may be implemented (e.g., completely, partially, and/or the like) by a non-transitory computer readable medium of the gateway device 160 (e.g., independent of, in lieu of, in addition to, or in combination with the wearable heart monitoring device 102). Additionally or alternatively, a processor of the gateway device 160 may be configured to receive at least one atypical ECG signal of at least one atypical ECG channel(s) (e.g., from the wearable heart monitoring device 102), to monitor the atypical ECG signal(s) to detect at least one arrhythmia (and/or atrial fibrillation) event based on the arrhythmia (and/or atrial fibrillation) classifier, and/or to transmit at least one communication based on the atrial fibrillation event(s) to the remote computer system, as described herein. In some embodiments, the gateway device 160 may communicate with the wearable heart monitoring device 102 via a short-range wireless communication connection (e.g., a Bluetooth® communication connection, a Zigbee® communication connection, a near-field communication (NFC) communication connection, a radio frequency identification (RFID) communication connection, and/or the like). For example, the gateway device 160 may communicate with the wearable heart monitoring device 102 via a short-range wireless communication connection and/or may communicate with the remote computer system 140 via the communication network 170.

The communication network 170 may include one or more wired and/or wireless networks. For example, the communication network 170 may include a cellular network (e.g., a long-term evolution (LTE®) network, a third generation (3G) network, a fourth generation (4G) network, a fifth generation (5G) network, a code division multiple access (CDMA) network, and/or the like), a public land mobile network (PLMN), a local area network (LAN), a wide area network (WAN), a metropolitan area network (MAN), a telephone network (e.g., the public switched telephone network (PSTN)), a private network (e.g., a private network associated with a transaction service provider), an ad hoc network, an intranet, the Internet, a fiber optic-based network, a cloud computing network, and/or the like, and/or a combination of these or other types of networks.

Figure 1B:
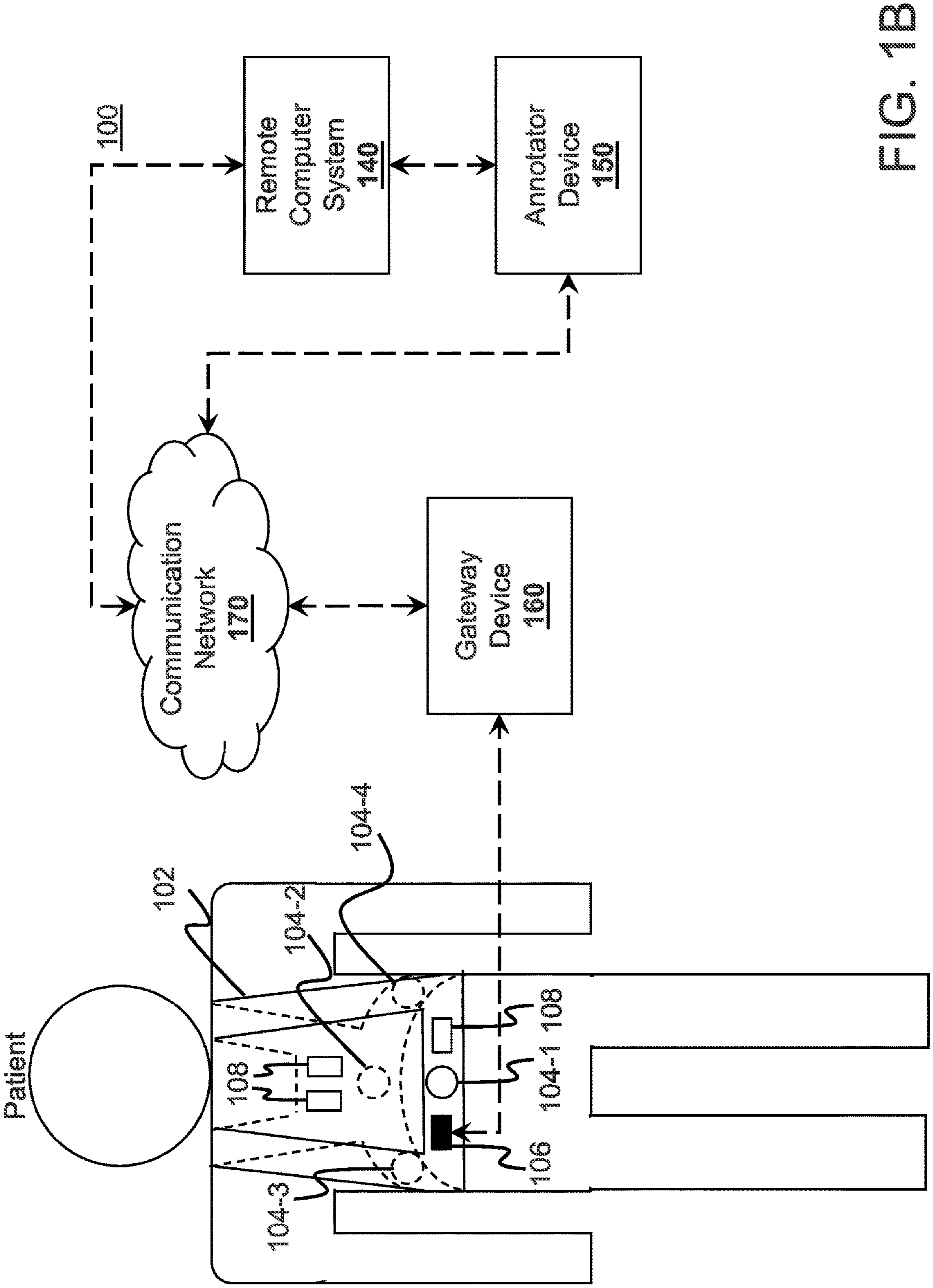

With reference to FIGS. 1A and 1B, in some embodiments, a wearable atypical ECG lead arrhythmia (and/or atrial fibrillation) monitoring system for identifying arrhythmias (and/or atrial fibrillations) experienced by a patient may include a wearable heart monitoring device 102, which may be an external wearable heart monitoring device configured for continuous and long-term monitoring of a patient. The wearable heart monitoring device 102 may include a plurality of ECG electrodes 104 and associated circuitry (e.g., circuitry of the controller 106 and/or a portion thereof) configured to sense surface ECG activity of the patient. Each ECG electrode 104 may be configured to be anatomically located within a circumferential atypical zone of the patient's torso in an uninhibiting manner so as to allow for the patient to be ambulatory. In some embodiments, the plurality of ECG electrodes 104 and associated circuitry (e.g., circuitry of the controller 106 and/or a portion thereof) may be configured to provide at least one atypical ECG channel producing at least one atypical ECG signal for the patient.

In some embodiments, the wearable heart monitoring device 102 (and/or the gateway device 160) may include a non-transitory computer-readable medium (e.g., of the controller 106 or a portion thereof, of the gateway device 160, and/or the like), which may include an arrhythmia (and/or atrial fibrillation) classifier comprising at least one neural network, as described herein. For example, the neural network may be trained based on a historical collection of a plurality of atypical ECG signal portions with annotation data. The annotation data may include at least one respective annotation for each respective atypical ECG signal portion of the plurality of atypical ECG signal portions. In some embodiments, the neural network may be further trained based on weight data for the annotation data. For example, the weight data may include a respective weight for each respective annotation based on a respective annotator of the respective annotation.

In some embodiments, the wearable heart monitoring device 102 (and/or the gateway device 160) may include at least one processor (e.g., of the controller 106 or a portion thereof, of the gateway device 160, and/or the like), which may be operatively connected to the at least one atypical ECG channel and the non-transitory computer-readable medium (e.g., both the processor(s) and the non-transitory computer-readable medium may be part of the controller 106 and/or a portion thereof). The processor(s) (e.g., of the controller 106 or a portion thereof, of the gateway device 160, and/or the like) may be configured to receive the atypical ECG signal(s) of the atypical ECG channel(s) and/or to monitor the atypical ECG signal(s) to detect at least one arrhythmia (and/or atrial fibrillation) event based on the arrhythmia (and/or atrial fibrillation) classifier. In some embodiments, the arrhythmia event(s) may include at least one of atrial fibrillation, flutter, supraventricular tachycardia, ventricular tachycardia, pause, atrioventricular (AV) block, ventricular fibrillation, bigeminy, trigeminy, ventricular ectopic beats, bradycardia, tachycardia, a change in heart rate, a change in morphology of the ECG signal(s), any combination thereof, and/or the like. In some embodiments, the processor(s) (e.g., of the controller 106 or a portion thereof, of the gateway device 160, and/or the like) may transmit at least one communication based on the arrhythmia (and/or atrial fibrillation) event(s) to a remote computer system 140 (e.g., via the communication network 170 and/or the like).

In some embodiments, the ECG electrodes 104 may include at least four ECG electrodes 104-1 to 104-4. Additionally or alternatively, the atypical ECG channel(s) may include at least two atypical ECG channels. For example, each atypical ECG channel may be associated with two respective ECG electrodes 104. In some embodiments, the four ECG electrodes 104 may include a front ECG electrode 104-1, a back ECG electrode 104-2, a first side ECG electrode 140-3, and a second side ECG electrode 104-4. The atypical ECG channels may include a front-to-back (FB) ECG channel associated with the front ECG electrode 104-1 and the back ECG electrode 104-2 and/or a side-to-side (SS) ECG channel associated with the first side ECG electrode 104-3 and the second side ECG electrode 104-4.

In some embodiments, the atypical ECG channels include a first atypical ECG channel and a second atypical ECG channel substantially orthogonal to the first atypical ECG channel. For example, the FB ECG channel (e.g., from the front ECG electrode 104-1 to the back ECG electrode 104-2) may be substantially orthogonal to the SS ECG channel (e.g., from the first side ECG electrode 104-3 to the second side ECG electrode 104-4). In some embodiments, substantially orthogonal may include at least one of about 90 degrees, within 10 degrees of 90 degrees, within 5 degrees of 90 degrees, within a tolerance range of 90 degrees, and/or the like.

In some embodiments, the atypical ECG channel(s) may include at least three atypical ECG channels. For example, the atypical ECG channel(s) may be associated with three ECG electrodes 104 (e.g., one channel from each ECG electrode 104), six ECG electrodes 104 (e.g., one channel from each pair of the ECG electrodes 104), and/or the like.

In some embodiments, the atypical ECG channel(s) may include at least four atypical ECG channels. For example, the atypical ECG channel(s) may be associated with four ECG electrodes 104 (e.g., one channel from each ECG electrode 104), eight ECG electrodes 104 (e.g., one channel from each pair of the ECG electrodes 104), and/or the like.

In some embodiments, the atypical ECG channel(s) may include at least one dynamically defined atypical ECG channel. For example, the associated circuitry (e.g., the controller 106 and/or a portion thereof) may be configured to analyze surface ECG activity of the patient and select at least two of the ECG electrodes 104 to define at least one dynamically defined atypical ECG channel.

In some embodiments, the (external) wearable heart monitoring device 102 may include a garment (e.g., a vest, a harness, a holter, at least one strap, a wearable cardioverter defibrillator, and/or the like) configured to be worn about a torso of the patient for an extended period of time, as described herein. In some embodiments, the garment may be further configured to house the ECG electrodes 104. For example, the garment may include a plurality of receptacles configured to receive the ECG electrodes 104 (e.g., a receptacle for each of the ECG electrodes 104).

In some embodiments, the (external) wearable heart monitoring device 102 may include a plurality therapy electrodes 108. For example, the therapy electrodes 108 may be housed in and/or configured to be housed in the garment. For example, the garment may include a plurality of receptacles configured to receive the therapy electrodes 108. In some embodiments, the (external) wearable heart monitoring device 102 (e.g., controller 106 thereof) may be configured to determine whether the patient is experiencing a treatable cardiac arrhythmia (and/or atrial fibrillation). For example, the (external) wearable heart monitoring device 102 (e.g., controller 106 thereof) may determine the patient is experiencing a treatable cardiac arrhythmia (and/or atrial fibrillation) based on identifying at least one arrhythmia (and/or atrial fibrillation) event with the (trained) classifier, as described herein. Additionally or alternatively, the (external) wearable heart monitoring device 102 (e.g., controller 106 thereof) may determine the patient is experiencing a treatable cardiac arrhythmia (and/or atrial fibrillation) based on other criteria (e.g., other programming, logic, rules, and/or the like). In some embodiments, the wearable heart monitoring device 102 (e.g., controller 106 thereof) may deliver one or more therapeutic shocks to the patient via the therapy electrodes 108 upon determining that the patient is experiencing a treatable cardiac arrhythmia (and/or atrial fibrillation). Additionally or alternatively, the wearable heart monitoring device 102 (e.g., controller 106 thereof) may deliver one or more therapeutic shocks to the patient via the therapy electrodes 108 upon receiving an input (e.g., from the controller 106, from the remote system 140, from the gateway device 160, and/or the like).

Figure 1C:
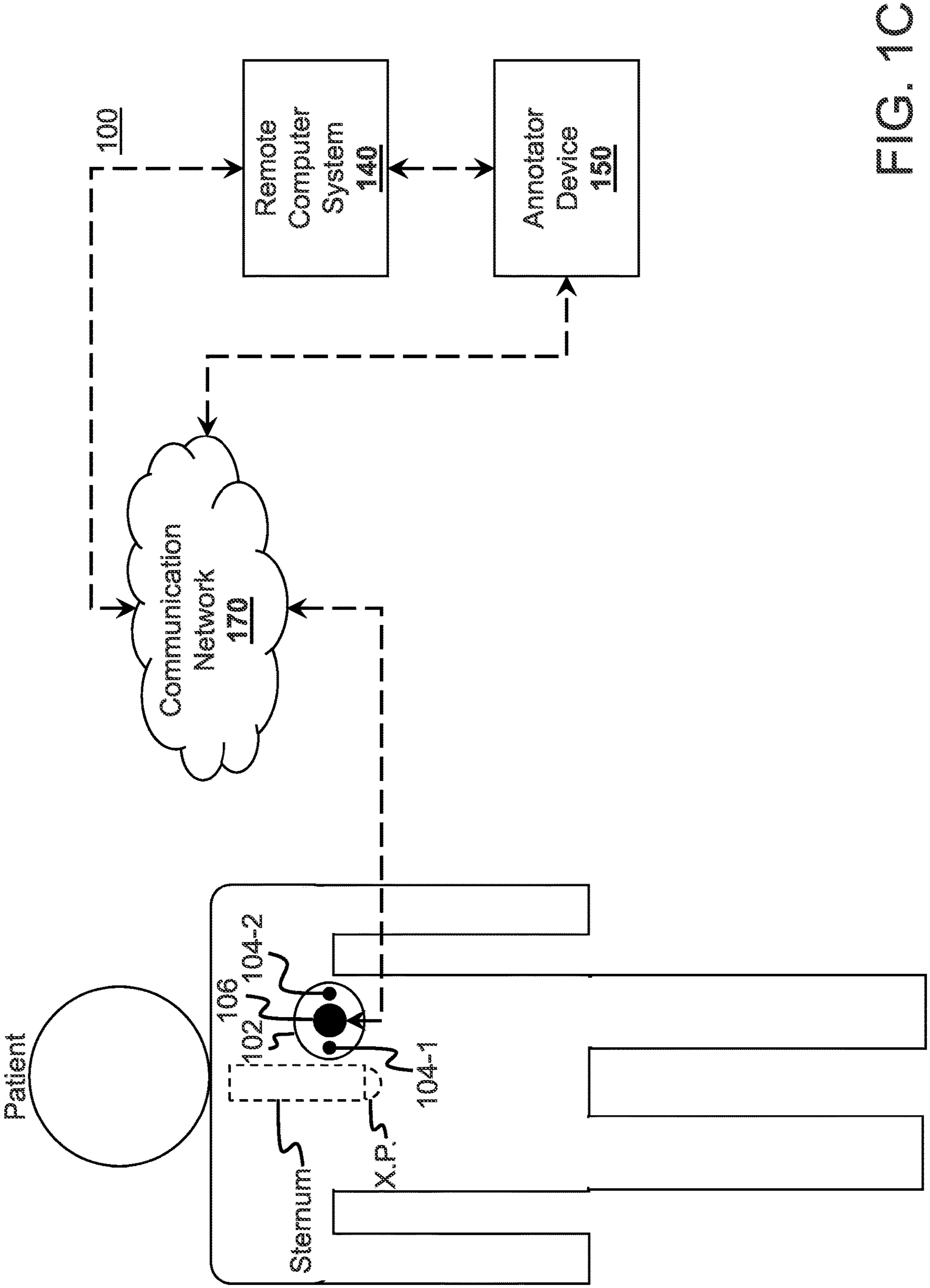
Figure 1D:
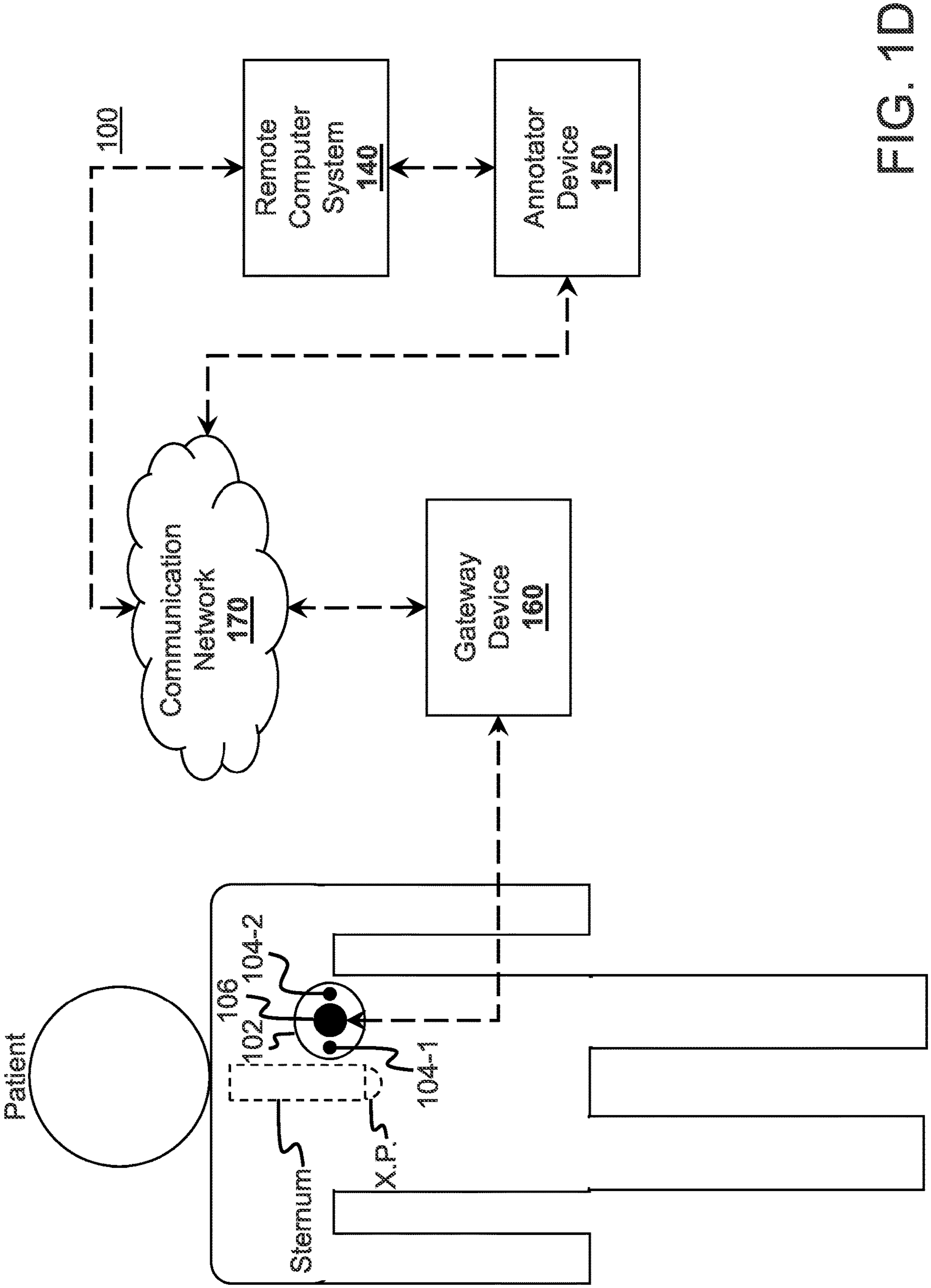
Figure 1E:
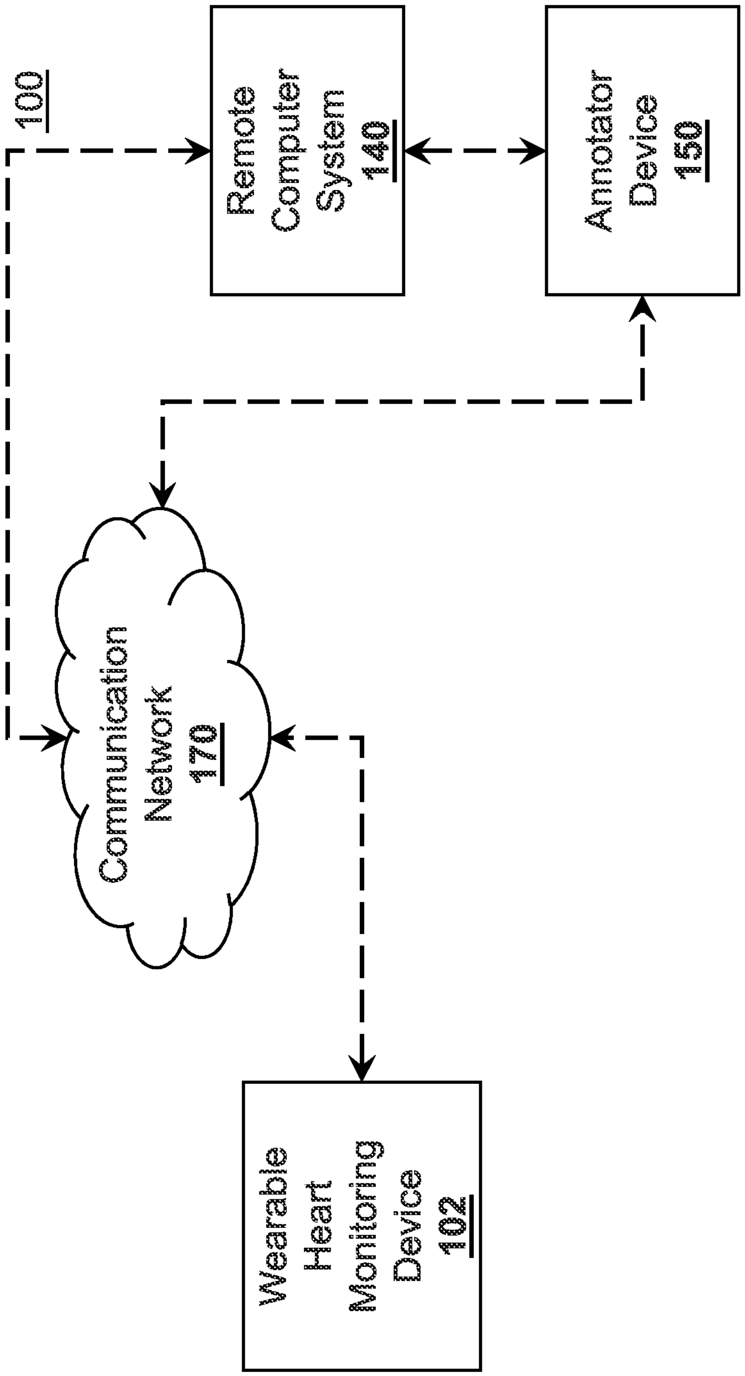
Figure 1F:
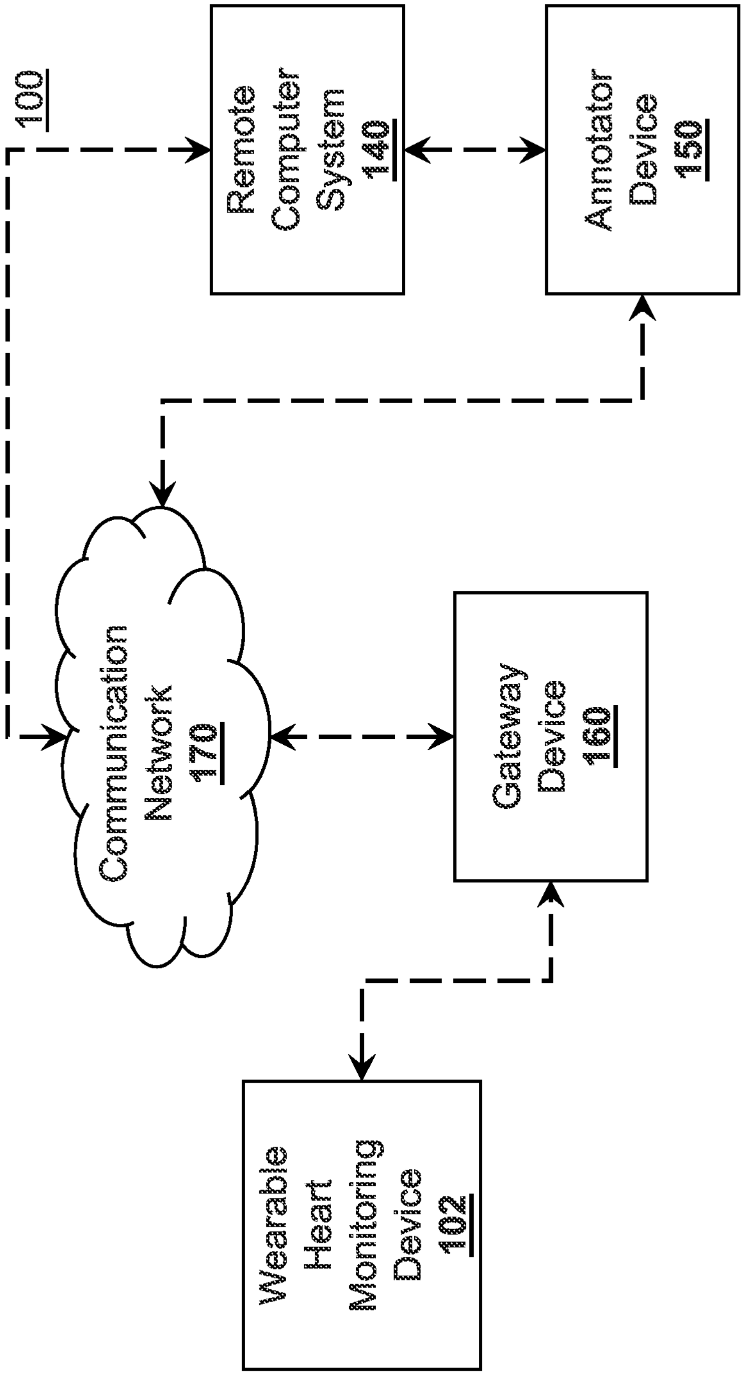

With reference to FIGS. 1C and 1D, in some embodiments, a wearable atypical ECG lead arrhythmia monitoring system for identifying arrhythmias experienced by a patient may include wearable heart monitoring device 102, which may include an external wearable heart monitoring device configured for continuous and long-term monitoring of a patient comprising. The wearable heart monitoring device 102 may include a plurality of ECG electrodes 104 and associated circuitry (e.g., circuitry of the controller 106 and/or a portion thereof) configured to sense surface ECG activity of the patient. In some embodiments, each ECG electrode 104 may be configured to be anatomically located on the patient's thorax superior to the patient's xiphoid process (e.g., "X.P.") and lateral to the patient's sternum (e.g., "sternum"), in an uninhibiting manner so as to allow for the patient to be ambulatory. In some embodiments, the plurality of ECG electrodes 104 and associated circuitry (e.g., circuitry of the controller 106 and/or a portion thereof) are configured to provide at least one atypical ECG channel producing at least one atypical ECG signal for the patient.

In some embodiments, the wearable heart monitoring device 102 (and/or the gateway device 160) may include a non-transitory computer-readable medium (e.g., of the controller 106 or a portion thereof, of the gateway device 160, and/or the like), which may include an arrhythmia (and/or atrial fibrillation) classifier comprising at least one neural network, as described herein. For example, the neural network may be trained based on a historical collection of a plurality of atypical ECG signal portions with annotation data. The annotation data may include at least one respective annotation for each respective atypical ECG signal portion of the plurality of atypical ECG signal portions. In some embodiments, the neural network may be further trained based on weight data for the annotation data. For example, the weight data may include a respective weight for each respective annotation based on a respective annotator of the respective annotation.

In some embodiments, the wearable heart monitoring device 102 (and/or the gateway device 160) may include at least one processor (e.g., of the controller 106 or a portion thereof, of the gateway device 160, and/or the like), which may be operatively connected to the at least one atypical ECG channel and the non-transitory computer-readable medium (e.g., both the processor(s) and the non-transitory computer-readable medium may be part of the controller 106 and/or a portion thereof). The processor(s) (e.g., of the controller 106 or a portion thereof, of the gateway device 160, and/or the like) may be configured to receive the atypical ECG signal(s) of the atypical ECG channel(s) and/or to monitor the atypical ECG signal(s) to detect at least one arrhythmia (and/or atrial fibrillation) event based on the arrhythmia (and/or atrial fibrillation) classifier. In some embodiments, the arrhythmia event(s) may include at least one of the types of arrhythmia event(s) described herein. In some embodiments, the processor(s) (e.g., of the controller 106 or a portion thereof, of the gateway device 160, and/or the like) may transmit at least one communication based on the arrhythmia (and/or atrial fibrillation) event(s) to a remote computer system 140 (e.g., via the communication network 170 and/or the like).

In some embodiments, at least two ECG electrodes 104 (e.g., first ECG electrode 104-1 and second ECG electrode 104-2) may be disposed within a predetermined distance on the patient's thorax superior to the patient's xiphoid process and lateral to the patient's sternum. In some embodiments, the predetermined distance may include 15 centimeters, and the ECG electrodes 104 (e.g., first ECG electrode 104-1 and second ECG electrode 104-2) may be spaced less than 15 centimeters. For example, ECG electrodes 104 (e.g., first ECG electrode 104-1 and second ECG electrode 104-2) may be spaced less than 10 centimeters. Additionally or alternatively, the ECG electrodes 104 (e.g., first ECG electrode 104-1 and second ECG electrode 104-2) may be spaced 5-15 centimeters. Additionally or alternatively, the ECG electrodes 104 (e.g., first ECG electrode 104-1 and second ECG electrode 104-2) may be spaced less than 5 centimeters.

In some embodiments, the wearable heart monitoring device 102 may include a single adhesive patch. For example, no wires may be used (e.g., no wires may be necessary) to connect the ECG electrodes 104 to the patch. For example, the ECG electrodes 104 and the associated circuitry (e.g., circuitry of the controller 106 and/or a portion thereof) each may be part of a single adhesive patch. For example, the ECG electrodes 104, the associated circuitry (e.g., circuitry of the controller 106 and/or a portion thereof), the processor(s), and the non-transitory computer readable medium all may be part of a single adhesive patch.

In some embodiments, the ECG electrodes 104 are all on one side of the patient's sternum. For example, at least some (e.g., all) of the ECG electrodes 104 may be left lateral to the patient's sternum. Additionally or alternatively, at least some (e.g., all) of the ECG electrodes 104 may be right lateral to the patient's sternum.

In some embodiments, the wearable heart monitoring device 102 may include a patch configured to be worn by the patient for an extended period of time. For example, the adhesive patch may be configured to be worn by (e.g., continuously adhesively coupled to the skin of) the patient for at least one of: 3-5 days, 5-7 days, 7-10 days, 10-14 days, or 14-30 days. In some embodiments, the patch may include the ECG electrodes 104. Additionally or alternatively, the patch may be configured to be adhesively coupled to skin of the patient. In some embodiments, the adhesive patch (or at least a portion thereof) may be disposable.

In some embodiments, the wearable heart monitoring device 102 may include controller 106, which may include and/or be a part of a cardiac monitoring unit. For example, the cardiac monitoring unit (e.g., the controller 106) may be configured to be removably attached to the patch. In some embodiments, the cardiac monitoring unit (e.g., the controller 106) may be configured to record the surface ECG activity of the patient sensed by the plurality of ECG electrodes 104 and associated circuitry (e.g., circuitry of the controller 106 and/or a portion thereof).

Referring again to FIGS. 1A-1F, in some embodiments, the respective weight for each respective annotator (e.g., of a plurality of annotators) may be based on a respective skill level of the respective annotator. For example, the respective skill level for each respective annotator may include a skill score. In some embodiments, the skill score may include at least one of an integer value from one to four; an integer value from one to five; an integer value from one to ten; an integer value from one to 100; one of 25, 50, 75, or 100; a value from zero to one, and/or the like. In some embodiments, the annotators may be given an initial test (e.g., a written test, a test on the annotator device 150, and/or the like), and each respective annotator's skill score may be based on that annotator's performance on the test (e.g., score, grade, assessment, and/or the like). Additionally or alternatively, each annotator may annotate (e.g., with annotator device 150 and/or the like) at least a subset of the historical collection of ECG signal portions (e.g., in addition to, in lieu of, or as part of the initial test), and each respective annotator's skill score may be based on that annotator's performance (e.g., accuracy, precision with respect to other annotators, and/or the like) annotating the (subset of the) historical collection of ECG signal portions. In some embodiments, a subset (e.g., a second subset) of the historical collection of ECG signal portions may be annotated (e.g., with the annotator device 150 and/or the like) by at least one annotator with a high skill level (e.g., an annotator with a high skill score; a committee of such annotators with high skill scores; an expert, such as a cardiologist, an electrophysiologist, a very experienced technician, and/or the like; a committee of such experts; any combination thereof, and/or the like). This (second) subset may be used for testing and validation of the trained model (e.g., arrhythmia and/or atrial fibrillation classifier) after training.

In some embodiments, the remote computer system 140 (and/or the wearable heart monitoring device 102 and/or the gateway device 160) may receive a plurality of skill scores (e.g., initial skill scores, updated skill scores as described herein, and/or the like) including a respective skill score for each respective annotator (e.g., of a plurality of annotators). The remote computer system 140 (and/or wearable heart monitoring device 102 and/or gateway device 160) may determine the respective weight for each respective annotator based on the plurality of scores. For example, the remote computer system 140 (and/or the wearable heart monitoring device 102 and/or the gateway device 160) may determine (e.g., calculate, look up, and/or the like) a weight for each respective annotator based on the respective skill score associated with the respective annotator.

In some embodiments, the remote computer system 140 (and/or the wearable heart monitoring device 102 and/or the gateway device 160) may receive (e.g., retrieve from a data storage device, receive from the annotator device 150, have stored on the remote computer system 140, and/or the like) the historical collection of the plurality of atypical ECG signal portions with the annotation data (e.g., at least one respective annotation from at least one of the plurality of annotators for each respective atypical ECG signal portion of the plurality of atypical ECG signal portions). In some embodiments, the remote computer system 140 (and/or the wearable heart monitoring device 102 and/or the gateway device 160) may train the arrhythmia (and/or atrial fibrillation) classifier based on the historical collection of the plurality of atypical ECG signal portions with the annotation data and based on the weight data (e.g., for each annotator of the plurality of annotators).

In some embodiments, training the arrhythmia (and/or atrial fibrillation) classifier may include adjusting (e.g., by the remote computer system 140, the wearable heart monitoring device 102, and/or the gateway device 160) a hyper-parameter of a loss function of the arrhythmia (and/or atrial fibrillation) classifier based on the weight data.

In some embodiments, training the arrhythmia (and/or atrial fibrillation) classifier may include adjusting (e.g., by the remote computer system 140, the wearable heart monitoring device 102, and/or the gateway device 160) the respective weight for each of at least one annotator based on a hyperparameter tuning process. For example, the respective weight for each annotator may be treated as a hyper-parameter, and the initial value of the hyperparameter may be the initial weight determined based on the initial skill score (e.g., based on the initial test given to the respective annotator). The arrhythmia (and/or atrial fibrillation) classifier may be trained based on a training subset (e.g., the first subset of the historical collection of atypical ECG signal portions, as described herein) and the initial value of the hyperparameter (e.g., the initial weights), and a metric (e.g., accuracy, loss, area under curve, precision, recall, F1 score, and/or the like) associated with the initial value of the hyperparameter may be determined based on a validation set (e.g., the second subset of the historical collection of atypical ECG signal portions, as described herein). The value of the hyperparameter may be adjusted (e.g., within a search space, within a range around the initial value, within a range around the initial skill score, randomly, and/or the like), and the arrhythmia (and/or atrial fibrillation) classifier may be retrained based on the training subset and the adjusted value of the hyperparameter so that the metric associated with the adjusted value of the hyperparameter may be determined based on the validation set. The adjustment of the value of the hyperparameter, retraining of the arrhythmia (and/or atrial fibrillation) classifier, and determination of the metric associated with the adjusted value of the hyperparameter may be iteratively repeated until a value of the hyperparameter that optimizes the metric (e.g., increases and/or maximizes accuracy, reduces and/or minimizes loss, and/or the like) is found (and/or until a maximum number of iterations is reached). The arrhythmia (and/or atrial fibrillation) classifier trained based on the optimized value of the hyperparameter may be considered to be the trained classifier (e.g., for communicating to and/or installing on the wearable heart monitoring device 102).

In some embodiments, the remote computer system 140 (and/or the wearable heart monitoring device 102 and/or the gateway device 160) may train the arrhythmia (and/or atrial fibrillation) classifier by generating, with the arrhythmia (and/or atrial fibrillation) classifier, predicted arrhythmia (and/or atrial fibrillation) event data (e.g., a prediction, a classification, a confidence score, and/or the like) for each atypical ECG signal portion of the historical collection (or a first subset thereof). For example, the remote computer system 140 (and/or the wearable heart monitoring device 102 and/or the gateway device 160) may input each atypical ECG signal portion of the historical collection (or a first subset thereof) into the arrhythmia (and/or atrial fibrillation) classifier to generate predicted arrhythmia (and/or atrial fibrillation) event data associated with at least one arrhythmia (and/or atrial fibrillation) event (or with the lack of such event, e.g., NSR) predicted to be within the respective atypical ECG signal portion (e.g., forward propagation and/or the like). The predicted arrhythmia (and/or atrial fibrillation) event data may be compared (e.g., by the remote computer system 140, the wearable heart monitoring device 102, and/or the gateway device 160) to the respective annotation data (e.g., from at least one annotator) for the respective atypical ECG signal portion, and/or the remote computer system 140 (and/or the wearable heart monitoring device 102 and/or the gateway device 160) may determine (e.g., calculate) a loss based on the predicted arrhythmia (and/or atrial fibrillation) event data and the annotation data. For example, the remote computer system 140 (and/or the wearable heart monitoring device 102 and/or the gateway device 160) may calculate the loss based on the predicted arrhythmia (and/or atrial fibrillation) event data, the respective annotation data, and at least one loss function (e.g., an objective function, an error calculation, a prediction error, a contrastive loss, and/or the like). In some embodiments, a hyperparameter of the loss function may be based on the weight associated with the respective annotator of the respective annotation data. For example, the remote computer system 140 (and/or the wearable heart monitoring device 102 and/or the gateway device 160) may calculate the loss based on the predicted arrhythmia (and/or atrial fibrillation) event data, the respective annotation data, the loss function, and the hyperparameter of the loss function (e.g., based on the weight associated with the respective annotator). As such, the hyperparameter of the loss function may be updated for each calculation of loss (e.g., for each respective atypical ECG signal portion) based on the weight associated with the respective annotator. In some embodiments, the remote computer system 140 (and/or the wearable heart monitoring device 102 and/or the gateway device 160) may update (e.g., adjust) the parameters (e.g., weights, connection values, and/or the like) of the arrhythmia (and/or atrial fibrillation) classifier (e.g., the neural network(s) thereof) based on the loss (e.g., using back propagation, gradient calculations, and/or the like).

In some embodiments, the arrhythmia (and/or atrial fibrillation) classifier may include at least one of a convolutional neural network, a stacked convolutional neural network, a densely connected convolutional network, a recurrent neural network, a residual neural network, a bidirectional long short-term memory network, a neural additive model, a neural network with an attention mechanism (e.g., additive dot product attention, scaled dot product attention, and/or the like), any combination thereof, and/or the like.

In some embodiments, the at least one communication (e.g., communicated by the wearable heart monitoring device 102 and/or the gateway device 160) may include at least one further atypical ECG signal portion associated with the at least one arrhythmia (and/or atrial fibrillation) event. For example, the remote computer system 140 (and/or the wearable heart monitoring device 102 and/or the gateway device 160) may be further configured to receive the communication(s) and receive (e.g., from the annotator device 150, from a data storage device of the remote computer system 140, and/or the like) further annotation data associated with the at least one further atypical ECG signal portion from at least one annotator of the plurality of annotators.

In some embodiments, the remote computer system 140 (and/or the wearable heart monitoring device 102 and/or the gateway device 160) may be further configured to compare the further annotation data to the at least one arrhythmia (and/or atrial fibrillation) event detected based on the arrhythmia (and/or atrial fibrillation) classifier. Additionally or alternatively, the remote computer system 140 (and/or the wearable heart monitoring device 102 and/or the gateway device 160) may determine an updated weight for each respective annotator based the further annotation data and the at least one arrhythmia (and/or atrial fibrillation) event (e.g., based on comparing the further annotation data to the at least one arrhythmia (and/or atrial fibrillation) event).

In some embodiments, the remote computer system 140 (and/or the wearable heart monitoring device 102 and/or the gateway device 160) may be further configured to retrain the arrhythmia (and/or atrial fibrillation) classifier based on the at least one further atypical ECG signal portion, the further annotation data, and the updated weight data. For example, retraining may be similar to training except at least some of the input data may be new and/or different (e.g., the at least one further atypical ECG signal portion, the further annotation data, the updated weight data, and/or the like).

In some embodiments, the remote computer system 140 (and/or the wearable heart monitoring device 102 and/or the gateway device 160) may be further configured to compare the further annotation data to the at least one arrhythmia (and/or atrial fibrillation) event detected based on the arrhythmia (and/or atrial fibrillation) classifier and/or transmit at least one further communication based on the further annotation data and the at least one arrhythmia (and/or atrial fibrillation) event (e.g., based on comparing the further annotation data to the at least one arrhythmia (and/or atrial fibrillation) event). For example, the at least one further communication may include a recommendation to retest one or more of the annotator(s), a recommendation to increase the respective skill score of one or more of the annotator(s), a recommendation to decrease the respective skill score of one or more of the annotator(s), any combination thereof, and/or the like.

In some embodiments, the remote computer system 140 (and/or the wearable heart monitoring device 102 and/or the gateway device 160) may be further configured to retrain the arrhythmia (and/or atrial fibrillation) classifier based on the at least one further atypical ECG signal portion, the further annotation data, and the weight data (e.g., the initial and/or original weight data).

In some embodiments, the remote computer system 140 (and/or the wearable heart monitoring device 102 and/or the gateway device 160) may be configured to receive at least one updated skill score comprising a respective updated skill score for each of at least one annotator of the plurality of annotators. Additionally or alternatively, the remote computer system 140 (and/or the wearable heart monitoring device 102 and/or the gateway device 160) may determine a respective updated weight for each of the annotator(s) based on the updated skill score(s). Additionally or alternatively, the remote computer system 140 (and/or the wearable heart monitoring device 102 and/or the gateway device 160) may retrain the arrhythmia (and/or atrial fibrillation) classifier based on the updated weight(s).

The number and arrangement of systems, devices, and/or networks shown in FIGS. 1A-1F are provided as an example. There may be additional systems, devices, and/or networks; fewer systems, devices, and/or networks; different systems, devices, and/or networks; and/or differently arranged systems, devices, and/or networks than those shown in FIGS. 1A-1F. Furthermore, two or more systems or devices shown in FIGS. 1A-1F may be implemented within a single system or device, or a single system or device shown in FIGS. 1A-1F may be implemented as multiple, distributed systems or devices. Additionally or alternatively, a set of systems (e.g., one or more systems) or a set of devices (e.g., one or more devices) of system 100 may perform one or more functions described as being performed by another set of systems or another set of devices of system 100.

Figure 2:
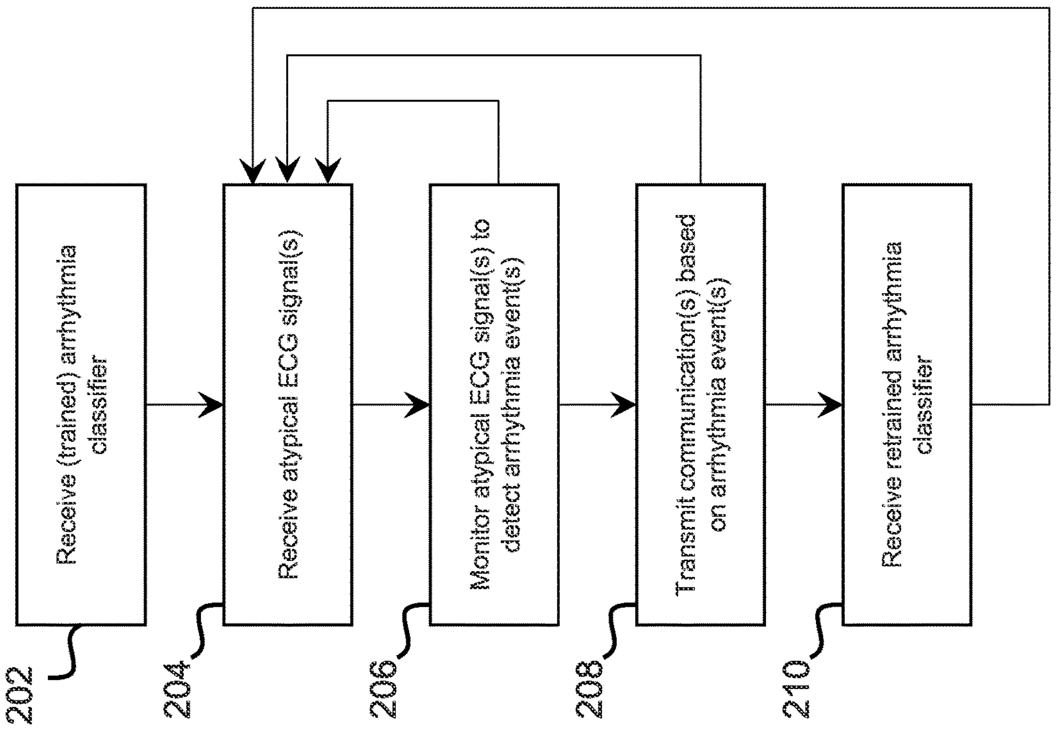
FIG. 2 shows an example flowchart of a process for cardiac diagnosis and/or monitoring with atypical ECG signals, according to some embodiments.

Referring now to FIG. 2, FIG. 2 is an example flowchart of a process 200 for cardiac diagnosis and/or monitoring with atypical electrocardiogram (ECG) signals, according to some embodiments. In some embodiments, one or more of the steps of the process 200 may be performed (e.g., completely, partially, and/or the like) by the wearable heart monitoring device 102. In some non-limiting embodiments, one or more of the steps of the process 200 may be performed (e.g., completely, partially, and/or the like) by another system, another device, another group of systems, or another group of devices, separate from or including the wearable heart monitoring device 102, such as the remote computer system 140, the annotator device 150, the gateway device 160, and/or the like. The number and arrangement of steps shown in FIG. 2 are provided as an example. In some non-limiting embodiments, the process 200 may include additional steps, fewer steps, different steps, or differently arranged steps than those shown in FIG. 2.

As shown in FIG. 2, at step 202, process 200 may include receiving an arrhythmia classifier. For example, the wearable heart monitoring device 102 may receive an arrhythmia classifier (e.g., communicated from the remote computer system 140, the gateway device 160, and/or the like). Additionally or alternatively, the arrhythmia classifier may be received by (e.g., installed on) the wearable heart monitoring device 102 as part of manufacturing and/or initial setup (e.g., by the manufacturer, a clinician, the patient, and/or the like).

In some embodiments, the remote computer system 140 may train the arrhythmia classifier, as described herein. Additionally or alternatively, the remote computer system 140 may communicate the trained arrhythmia classifier to the wearable heart monitoring device 102 (and/or the gateway device 160). In some embodiments, the gateway device 160 may communicate the trained arrhythmia classifier to the wearable heart monitoring device 102.

In some embodiments, the wearable heart monitoring device 102 (and/or the gateway device 160) may include a non-transitory computer-readable medium (e.g., of the controller 106 or a portion thereof, of the gateway device 160, and/or the like), which may include (e.g., store and/or the like) the arrhythmia classifier comprising at least one neural network, as described herein.

As shown in FIG. 2, at step 204, process 200 may include receiving at least one atypical ECG signal. For example, the wearable heart monitoring device 102 (e.g., the processor(s) and/or controller 106 thereof) may receive at least one atypical ECG signal of at least one atypical ECG channel, as described herein. Additionally or alternatively, the gateway device 160 (e.g., the processor(s) thereof) may receive at least one atypical ECG signal of at least one atypical ECG channel (e.g., from the wearable heart monitoring device 102).

In some embodiments, the wearable heart monitoring device 102 may include a plurality of ECG electrodes 104 and associated circuitry (e.g., circuitry of the controller 106 and/or a portion thereof) configured to sense surface ECG activity of the patient, as described herein. In some embodiments, the plurality of ECG electrodes 104 and associated circuitry (e.g., circuitry of the controller 106 and/or a portion thereof) may be configured to provide at least one atypical ECG channel producing at least one atypical ECG signal for the patient. For example, the wearable heart monitoring device 102 (e.g., the processor(s) and/or controller 106 thereof) may receive the atypical ECG signal(s) of the atypical ECG channel(s), as described herein.

In some embodiments, each ECG electrode 104 may be configured to be anatomically located within a circumferential atypical zone of the patient's torso in an uninhibiting manner so as to allow for the patient to be ambulatory, as described herein.

In some embodiments, each ECG electrode 104 may be configured to be anatomically located on the patient's thorax superior to the patient's xiphoid process (e.g., "X.P.") and lateral to the patient's sternum (e.g., "Sternum"), in an uninhibiting manner so as to allow for the patient to be ambulatory, as described herein.

As shown in FIG. 2, at step 206, process 200 may include monitoring the atypical ECG signal(s) to detect at least one arrhythmia event. For example, the wearable heart monitoring device 102 (e.g., the processor(s) and/or controller 106 thereof) may monitor the atypical ECG signal(s) to detect at least one arrhythmia event based on the arrhythmia classifier, as described herein. Additionally or alternatively, the gateway device 160 (e.g., the processor(s) thereof) may monitor the atypical ECG signal(s) (e.g., from the wearable heart monitoring device 102) to detect at least one arrhythmia event based on the arrhythmia classifier, as described herein.

In some embodiments, the wearable heart monitoring device 102 (e.g., the processor(s) and/or controller 106 thereof) may input the atypical ECG signal(s) and/or at least a portion thereof into the arrhythmia classifier to generate predicted arrhythmia event data associated with at least one arrhythmia event (or with the lack of such event, e.g., NSR) predicted to be within the respective atypical ECG signal portion (e.g., forward propagation and/or the like), as described herein. For example, the wearable heart monitoring device 102 (e.g., the processor(s) and/or controller 106 thereof) may detect at least one arrhythmia event based on the predicted arrhythmia event data.

In some embodiments, the arrhythmia event(s) may include at least one of atrial fibrillation, flutter, supraventricular tachycardia, ventricular tachycardia, pause, atrioventricular (AV) block, ventricular fibrillation, bigeminy, trigeminy, ventricular ectopic beats, bradycardia, tachycardia, a change in heart rate, a change in morphology of the ECG signal(s), any combination thereof, and/or the like.

In some embodiments, the wearable heart monitoring device 102 may include a plurality of therapy electrodes 108. For example, the wearable heart monitoring device 102 (e.g., controller 106 thereof) may determine the patient is experiencing a treatable cardiac arrhythmia based on identifying at least one arrhythmia event with the (trained) classifier, as described herein. Additionally or alternatively, the wearable heart monitoring device 102 (e.g., controller 106 thereof) may determine the patient is experiencing a treatable cardiac arrhythmia based on other criteria (e.g., other programming, logic, rules, and/or the like). In some embodiments, the wearable heart monitoring device 102 may deliver one or more therapeutic shocks to the patient via the therapy electrodes 108 (e.g., upon determining that the patient is experiencing a treatable cardiac arrhythmia), as described herein.

As shown in FIG. 2, at step 208, process 200 may include transmitting at least one communication based on the arrhythmia event(s). For example, the wearable heart monitoring device 102 (e.g., the processor(s) and/or controller 106 thereof) may transmit at least one communication based on the arrhythmia event(s) (e.g., to the remote computer system 140 and/or the gateway device 160), as described herein. Additionally or alternatively, the gateway device 160 (e.g., the processor(s) thereof) may transmit at least one communication based on the arrhythmia event(s) (e.g., to the remote computer system 140), as described herein.

In some embodiments, the at least one communication (e.g., communicated by the wearable heart monitoring device 102 and/or the gateway device 160) may include at least one further atypical ECG signal portion associated with the at least one arrhythmia event, as described herein.

As shown in FIG. 2, at step 210, process 200 may include receiving a retrained arrhythmia classifier. For example, the remote computer system 140 (and/or the wearable heart monitoring device 102 and/or the gateway device 160) may retrain the arrhythmia classifier and/or communicate the retrained arrhythmia classifier, as described herein. Additionally or alternatively, the wearable heart monitoring device 102 (and/or the gateway device 160) may receive the retrained the arrhythmia classifier, as described herein.

In some non-limiting embodiments, process 200 may include repeating at least some steps (e.g., steps 204-206, 204-208, 204-210, and/or the like). For example, at least some such steps may be repeated continuously, periodically, and/or the like. For example, the atypical ECG signal(s) may be received (step 204) continuously. Additionally or alternatively, the received atypical ECG signals may be analyzed using the arrhythmia classifier to continuously monitor the atypical ECG signal(s) to detect arrhythmia events (step 206). In some embodiments, upon detection of at least one arrhythmia event, the communication(s) may be transmitted, e.g., as often as arrhythmia events occur and/or are detected (step 208). In some embodiments, the arrhythmia classifier may be retrained (and/or communicated to the wearable heart monitoring device 102) periodically, continuously, and/or the like (step 210).

Figure 3:
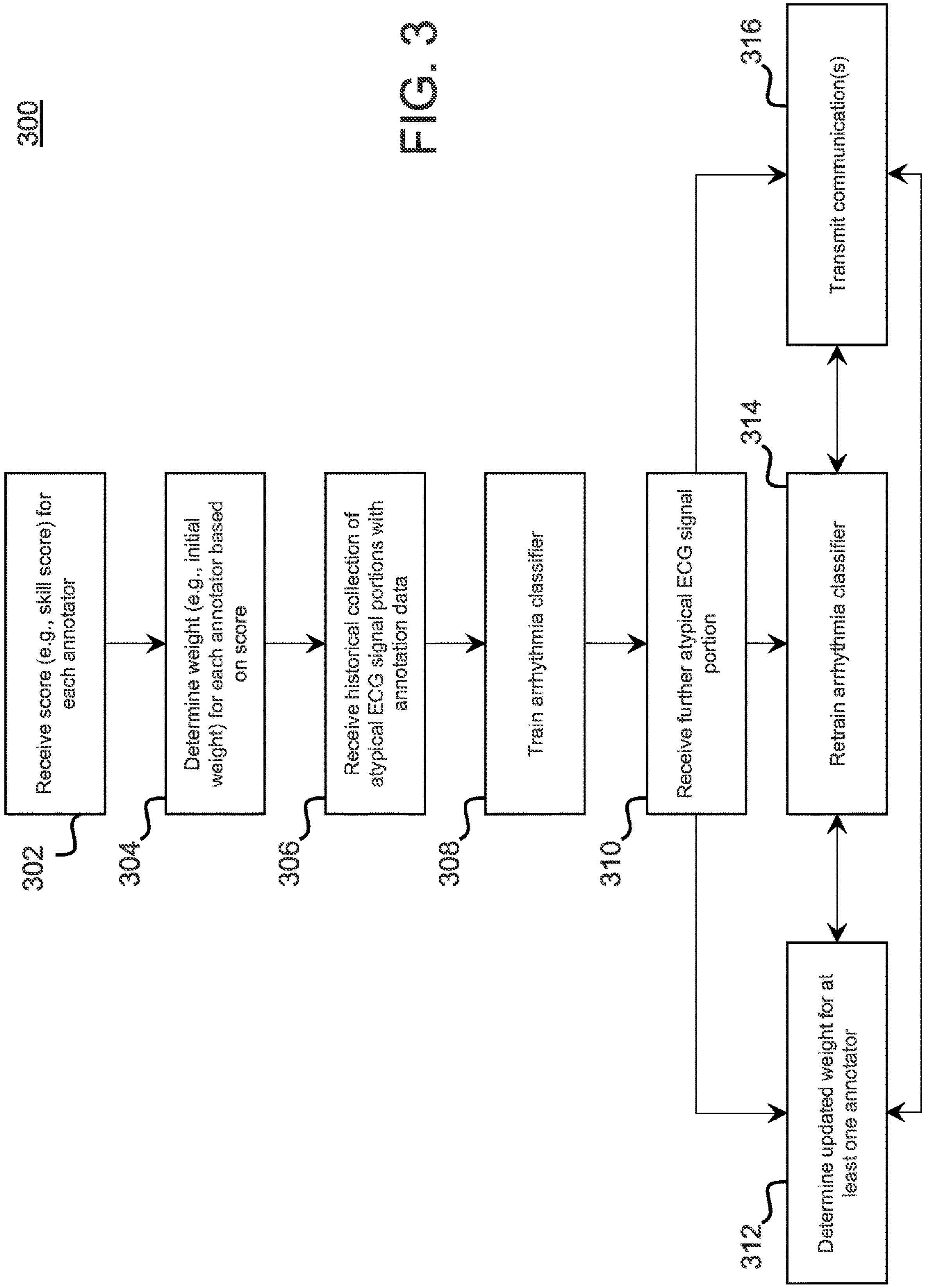
FIG. 3 shows an example flowchart of a process for cardiac diagnosis and/or monitoring with atypical ECG signals, according to some embodiments.

Referring now to FIG. 3, FIG. 3 is an example flowchart of a process 300 for cardiac diagnosis and/or monitoring with atypical electrocardiogram (ECG) signals, according to some embodiments. In some embodiments, one or more of the steps of the process 300 may be performed (e.g., completely, partially, and/or the like) by the remote computer system 140. In some non-limiting embodiments, one or more of the steps of the process 300 may be performed (e.g., completely, partially, and/or the like) by another system, another device, another group of systems, or another group of devices, separate from or including the remote computer system 140, such as the wearable heart monitoring device 102, the annotator device 150, the gateway device 160, and/or the like. The number and arrangement of steps shown in FIG. 3 are provided as an example. In some non-limiting embodiments, the process 300 may include additional steps, fewer steps, different steps, or differently arranged steps than those shown in FIG. 3.

As shown in FIG. 3, at step 302, process 300 may include receiving at least one score (e.g., a skill score) for each annotator of a plurality of annotators. For example, remote computer system 140 may receive a plurality of scores including a respective score for each respective annotator of a plurality of annotators, as described herein.

In some embodiments, the remote computer system 140 may receive a plurality of skill scores (e.g., initial skill scores, updated skill scores as described herein, and/or the like) including a respective skill score for each respective annotator (e.g., of a plurality of annotators), as described herein.

In some embodiments, the annotators may be given an initial test (e.g., a written test, a test on the annotator device 150, and/or the like), and each respective annotator's skill score may be based on that annotator's performance on the test (e.g., score, grade, assessment, and/or the like), as described herein. Additionally or alternatively, each annotator may annotate (e.g., with annotator device 150 and/or the like) at least a subset of the historical collection of ECG signal portions (e.g., in addition to, in lieu of, or as part of the initial test), and each respective annotator's skill score may be based on that annotator's performance (e.g., accuracy, precision with respect to other annotators, and/or the like) annotating the (subset of the) historical collection of ECG signal portions, as described herein.

As shown in FIG. 3, at step 304, process 300 may include determining a weight for each annotator based on the scores. For example, remote computer system 140 may determine a weight (e.g., initial weight, updated weight, and/or the like) for each respective annotator based on the respective scores (e.g., skill score) of the respective annotator.

In some embodiments, the remote computer system 140 may determine the respective weight for each respective annotator based on the plurality of scores. For example, the remote computer system 140 (and/or the wearable heart monitoring device 102 and/or the gateway device 160) may determine (e.g., calculate, look up, and/or the like) a weight for each respective annotator based on the respective skill score associated with the respective annotator.

In some embodiments, the respective weight for each respective annotator (e.g., of the plurality of annotators) may be based on a respective skill level of the respective annotator, as described herein. For example, the respective skill level for each respective annotator may include and/or be based on the skill score of the respective annotator.

In some embodiments, the skill score may include at least one of an integer value from one to four; an integer value from one to five; an integer value from one to ten; an integer value from one to 100; one of 25, 50, 75, or 100; a value from zero to one, and/or the like.

As shown in FIG. 3, at step 306, process 300 may include receiving a historical collection of atypical ECG signal portions with annotation data. For example, the remote computer system 140 may receive a historical collection of a plurality of atypical electrocardiogram (ECG) signal portions with annotation data, as described herein. For example, the annotation data may include at least one respective annotation for each respective atypical ECG signal portion of the plurality of atypical ECG signal portions.

In some embodiments, the remote computer system 140 may retrieve at least a portion of the historical collection of the plurality of atypical ECG signal and/or the annotation data from a data storage device, as described herein. In some embodiments, the remote computer system 140 may receive at least a portion of the historical collection of the plurality of atypical ECG signal and/or the annotation data from the annotator device 150, as described herein.

As shown in FIG. 3, at step 308, process 300 may include training the arrhythmia classifier. For example, the remote computer system 140 may train the arrhythmia classifier based on the historical collection of the plurality of atypical ECG signal portions with the annotation data and based on the weight data for the annotation data, as described herein.

In some embodiments, the remote computer system 140 training the arrhythmia classifier may include adjusting (e.g., by the remote computer system 140) a hyperparameter of a loss function of the arrhythmia (and/or atrial fibrillation) classifier based on the weight data, as described herein.

In some embodiments, training the arrhythmia (and/or atrial fibrillation) classifier may include adjusting (e.g., by the remote computer system 140, the wearable heart monitoring device 102, and/or the gateway device 160) the respective weight for each of at least one annotator based on a hyperparameter tuning process. For example, the respective weight for each annotator may be treated as a hyperparameter, and the initial value of the hyperparameter may be the initial weight determined based on the initial skill score (e.g., based on the initial test given to the respective annotator). The arrhythmia (and/or atrial fibrillation) classifier may be trained based on a training subset (e.g., the first subset of the historical collection of atypical ECG signal portions, as described herein) and the initial value of the hyperparameter (e.g., the initial weights), and a metric (e.g., accuracy, loss, area under curve, precision, recall, F1 score, and/or the like) associated with the initial value of the hyperparameter may be determined based on a validation set (e.g., the second subset of the historical collection of atypical ECG signal portions, as described herein). The value of the hyperparameter may be adjusted (e.g., within a search space, within a range around the initial value, within a range around the initial skill score, randomly, and/or the like), and the arrhythmia (and/or atrial fibrillation) classifier may be retrained based on the training subset and the adjusted value of the hyperparameter so that the metric associated with the adjusted value of the hyperparameter may be determined based on the validation set. The adjustment of the value of the hyperparameter, retraining of the arrhythmia (and/or atrial fibrillation) classifier, and determination of the metric associated with the adjusted value of the hyperparameter may be iteratively repeated until a value of the hyperparameter that optimizes the metric (e.g., increases and/or maximizes accuracy, reduces and/or minimizes loss, and/or the like) is found (and/or until a maximum number of iterations is reached). The arrhythmia (and/or atrial fibrillation) classifier trained based on the optimized value of the hyperparameter may be considered to be the trained classifier (e.g., for communicating to and/or installing on the wearable heart monitoring device 102).

In some embodiments, the remote computer system 140 may train the arrhythmia classifier by generating, with the arrhythmia classifier, predicted arrhythmia event data (e.g., a prediction, a classification, a confidence score, and/or the like) for each atypical ECG signal portion of the historical collection (or a first subset thereof), as described herein. For example, the remote computer system 140 may input each atypical ECG signal portion of the historical collection (or a first subset thereof) into the arrhythmia classifier to generate predicted arrhythmia event data associated with at least one arrhythmia event (or with the lack of such event, e.g., NSR) predicted to be within the respective atypical ECG signal portion (e.g., forward propagation and/or the like), as described herein. The predicted arrhythmia event data may be compared (e.g., by the remote computer system 140) to the respective annotation data (e.g., from at least one annotator) for the respective atypical ECG signal portion, and/or the remote computer system 140 may determine (e.g., calculate) a loss based on the predicted arrhythmia event data and the annotation data. For example, the remote computer system 140 may calculate the loss based on the predicted arrhythmia event data, the respective annotation data, at least one loss function, and/or a hyperparameter of the loss function based on the weight associated with the respective annotator of the respective annotation data, as described herein. In some embodiments, the remote computer system 140 may update (e.g., adjust) the parameters (e.g., weights, connection values, and/or the like) of the arrhythmia classifier (e.g., the neural network(s) thereof) based on the loss (e.g., using back propagation, gradient calculations, and/or the like).

In some embodiments, a subset (e.g., a second subset) of the historical collection of ECG signal portions may be annotated (e.g., with the annotator device 150 and/or the like) by at least one annotator with a high skill level (e.g., an annotator with a high skill score; a committee of such annotators with high skill scores; an expert, such as a cardiologist, an electrophysiologist, a very experienced technician, and/or the like; a committee of such experts; any combination thereof, and/or the like). This (second) subset may be used for testing and validation of the trained model (e.g., arrhythmia and/or atrial fibrillation classifier) after training. For example, the performance (e.g., accuracy (ACC), loss (LOSS), area under curve (AUC), precision (PRE), recall (REC), F1 score (F1), specificity (SPEC), number of parameters (#P), latency (LAT) and/or the like) of the trained arrhythmia classifier may be tested, e.g., based on comparing the output (e.g., predicted arrhythmia event) of the trained arrhythmia classifier for each atypical ECG signal portion in the (second) subset with the annotation data from the (highly skilled) annotator(s). For the purpose of illustration and not limitation, the following table (Table 1) shows the aforementioned exemplary performance metrics determined based on using each of the following types of neural networks for the arrhythmia classifier: a stacked convolutional neural network (Stacked CNN), a residual network (ResNet), a densely connected convolutional network (DenseNet), a bidirectional long short-term memory network (Bi-LSTM), a neural network with additive dot product attention (Additive), and a neural network with scaled dot product attention (SDP):

TABLE 1

| Model | ACC | LOSS | AUC | PRE | REC | F1 | SPEC | # P | LAT (s) |
|---|---|---|---|---|---|---|---|---|---|
| Stacked CNN | 0.9651 | 0.0898 | 0.9737 | 0.7781 | 0.8288 | 0.8027 | 0.9779 | 1,609,057 | 1.50 |
| ResNet | 0.9624 | 0.1048 | 0.9656 | 0.7535 | 0.8322 | 0.7909 | 0.9745 | 1,118,549 | 0.72 |
| DenseNet | 0.9579 | 0.1032 | 0.9719 | 0.7260 | 0.8168 | 0.7687 | 0.9711 | 335,611 | 0.93 |
| Bi-LSTM | 0.9564 | 0.0999 | 0.9650 | 0.7260 | 0.7894 | 0.7564 | 0.9721 | 217,369 | 0.75 |
| Additive | 0.9588 | 0.1105 | 0.9708 | 0.7356 | 0.8099 | 0.7710 | 0.9727 | 200,408 | 0.75 |
| SDP | 0.9676 | 0.0929 | 0.9721 | 0.8212 | 0.7945 | 0.8077 | 0.9838 | 231,607 | 0.75 |

As shown in FIG. 3, at step 310, process 300 may include receiving at least one further atypical ECG signal portion. For example, the remote computer system 140 may receive (e.g., from wearable heart monitoring device 102, gateway device 160, annotator device 150, and/or a data storage device) at least one further atypical ECG signal portion and/or receive (e.g., from annotator device 150 and/or a data storage device) further annotation data from at least one annotator of the plurality of annotators (e.g., receive at least one further atypical ECG signal portion with further annotation data and/or the like), as described herein.

In some embodiments, the remote computer system 140 may analyze the further atypical ECG signal portion(s) to detect at least one arrhythmia event based on the arrhythmia classifier, as described herein.

In some embodiments, the remote computer system 140 may compare the further annotation data to the arrhythmia event(s), as described herein.

As shown in FIG. 3, at step 312, process 300 may include determining at least one updated weight for at least one annotator. For example, the remote computer system 140 may determine an updated weight for each of at least one annotator based on comparing the further annotation data to the at least one arrhythmia event, as described herein.

In some embodiments, the remote computer system 140 may be further configured to compare the further annotation data to at least one arrhythmia event detected based on the arrhythmia classifier. Additionally or alternatively, the remote computer system 140 may determine an updated weight for each respective annotator based on further annotation data and the arrhythmia event(s) (e.g., based on comparing the further annotation data to the arrhythmia events(s)).

As shown in FIG. 3, at step 314, process 300 may include retraining the arrhythmia classifier. For example, the remote computer system 140 may retrain the arrhythmia classifier based on the at least one further atypical ECG signal portion, the further annotation data, and/or the updated weight data.

In some embodiments, the remote computer system 140 may be further configured to retrain the arrhythmia classifier based on the further atypical ECG signal portion(s), the further annotation data, and the updated weight data. For example, retraining may be similar to training except at least some of the input data may be new and/or different (e.g., the further atypical ECG signal portion(s), the further annotation data, the updated weight data, and/or the like).

In some embodiments, the remote computer system 140 may be further configured to retrain the arrhythmia classifier based on the further atypical ECG signal portion(s), the further annotation data, and the weight data (e.g., the initial and/or original weight data).

As shown in FIG. 3, at step 316, process 300 may include transmitting at least one communication. For example, the remote computer system 140 may transmit at least one communication (e.g., based on comparing the further annotation data to the arrhythmia event(s)), as described herein.

In some embodiments, the remote computer system 140 may be further configured to compare the further annotation data to the at least one arrhythmia event detected based on the arrhythmia classifier and/or transmit at least one further communication based on the further annotation data and the at least one arrhythmia event (e.g., based on comparing the further annotation data to the at least one arrhythmia event), as described herein. For example, the at least one further communication may include a recommendation to retest one or more of the annotator(s), a recommendation to increase the respective skill score of one or more of the annotator(s), a recommendation to decrease the respective skill score of one or more of the annotator(s), any combination thereof, and/or the like, as described herein.

Figure 4:
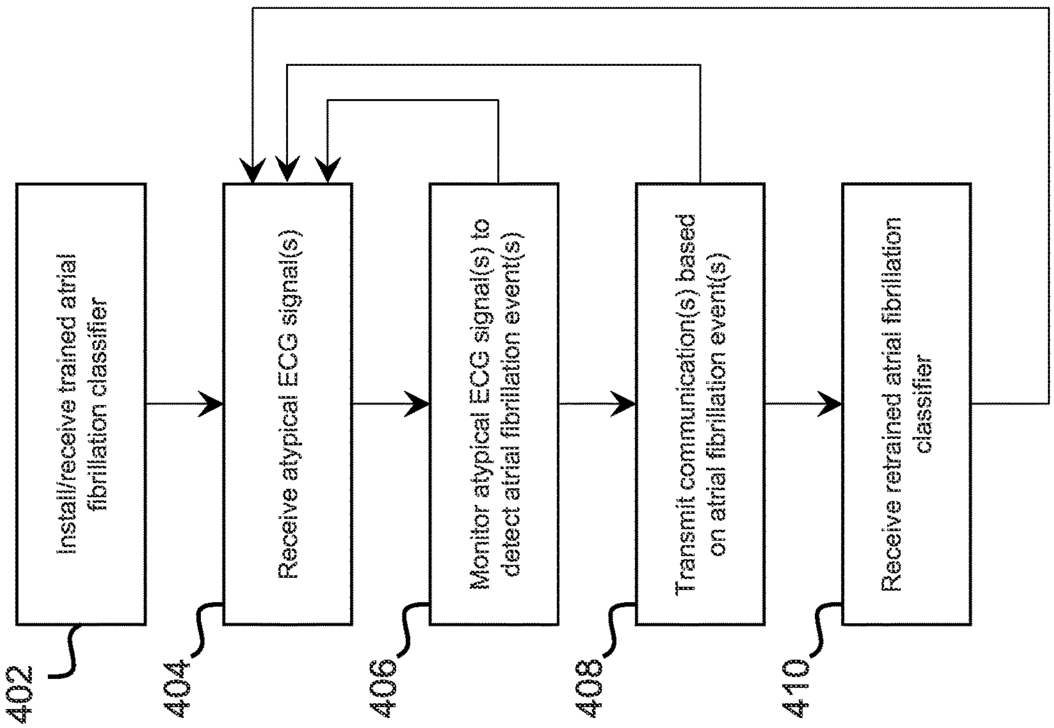
FIG. 4 shows an example flowchart of a process for cardiac diagnosis and/or monitoring with atypical ECG signals, according to some embodiments.

Referring now to FIG. 4, FIG. 4 is an example flowchart of a process 400 for cardiac diagnosis and/or monitoring with atypical electrocardiogram (ECG) signals, according to some embodiments. In some embodiments, one or more of the steps of the process 400 may be performed (e.g., completely, partially, and/or the like) by the wearable heart monitoring device 102. In some non-limiting embodiments, one or more of the steps of the process 400 may be performed (e.g., completely, partially, and/or the like) by another system, another device, another group of systems, or another group of devices, separate from or including the wearable heart monitoring device 102, such as the remote computer system 140, the annotator device 150, the gateway device 160, and/or the like. The number and arrangement of steps shown in FIG. 4 are provided as an example. In some non-limiting embodiments, the process 400 may include additional steps, fewer steps, different steps, or differently arranged steps than those shown in FIG. 4.

As shown in FIG. 4, at step 402, process 400 may include receiving an atrial fibrillation classifier. For example, the wearable heart monitoring device 102 may receive an atrial fibrillation classifier (e.g., communicated from the remote computer system 140, the gateway device 160, and/or the like). Additionally or alternatively, the atrial fibrillation classifier may be received by (e.g., installed on) the wearable heart monitoring device 102 as part of manufacturing and/or initial setup (e.g., by the manufacturer, a clinician, the patient, and/or the like).

In some embodiments, the remote computer system 140 may train the atrial fibrillation classifier, as described herein. Additionally or alternatively, the remote computer system 140 may communicate the trained atrial fibrillation classifier to the wearable heart monitoring device 102 (and/or the gateway device 160). In some embodiments, the gateway device 160 may communicate the trained atrial fibrillation classifier to the wearable heart monitoring device 102.

In some embodiments, the wearable heart monitoring device 102 (and/or the gateway device 160) may include a non-transitory computer-readable medium (e.g., of the controller 106 or a portion thereof, of the gateway device 160, and/or the like), which may include (e.g., store and/or the like) the atrial fibrillation classifier comprising at least one neural network, as described herein.

As shown in FIG. 4, at step 404, process 400 may include receiving at least one atypical ECG signal. For example, the wearable heart monitoring device 102 (e.g., the processor(s) and/or controller 106 thereof) may receive at least one atypical ECG signal of at least one atypical ECG channel, as described herein. Additionally or alternatively, the gateway device 160 (e.g., the processor(s) thereof) may receive at least one atypical ECG signal of at least one atypical ECG channel (e.g., from the wearable heart monitoring device 102).

In some embodiments, the wearable heart monitoring device 102 may include a plurality of ECG electrodes 104 and associated circuitry (e.g., circuitry of the controller 106 and/or a portion thereof) configured to sense surface ECG activity of the patient, as described herein. In some embodiments, the plurality of ECG electrodes 104 and associated circuitry (e.g., circuitry of the controller 106 and/or a portion thereof) may be configured to provide at least one atypical ECG channel producing at least one atypical ECG signal for the patient. For example, the wearable heart monitoring device 102 (e.g., the processor(s) and/or controller 106 thereof) may receive the atypical ECG signal(s) of the atypical ECG channel(s), as described herein.

In some embodiments, each ECG electrode 104 may be configured to be anatomically located within a circumferential atypical zone of the patient's torso in an uninhibiting manner so as to allow for the patient to be ambulatory, as described herein.

In some embodiments, each ECG electrode 104 may be configured to be anatomically located on the patient's thorax superior to the patient's xiphoid process (e.g., "X.P.") and lateral to the patient's sternum (e.g., "Sternum"), in an uninhibiting manner so as to allow for the patient to be ambulatory, as described herein.

As shown in FIG. 4, at step 406, process 400 may include monitoring the atypical ECG signal(s) to detect at least one atrial fibrillation event. For example, the wearable heart monitoring device 102 (e.g., the processor(s) and/or controller 106 thereof) may monitor the atypical ECG signal(s) to detect at least one atrial fibrillation event based on the atrial fibrillation classifier, as described herein. Additionally or alternatively, the gateway device 160 (e.g., the processor(s) thereof) may monitor the atypical ECG signal(s) (e.g., from the wearable heart monitoring device 102) to detect at least one atrial fibrillation event based on the atrial fibrillation classifier, as described herein.

In some embodiments, the wearable heart monitoring device 102 (e.g., the processor(s) and/or controller 106 thereof) may input the atypical ECG signal(s) and/or at least a portion thereof into the atrial fibrillation classifier to generate predicted atrial fibrillation event data associated with at least one atrial fibrillation event (or with the lack of such event, e.g., NSR) predicted to be within the respective atypical ECG signal portion (e.g., forward propagation and/or the like), as described herein. For example, the wearable heart monitoring device 102 (e.g., the processor(s) and/or controller 106 thereof) may detect at least one atrial fibrillation event based on the predicted atrial fibrillation event data.

In some embodiments, the atrial fibrillation event(s) may include at least one of atrial fibrillation, flutter, supraventricular tachycardia, ventricular tachycardia, pause, atrioventricular (AV) block, ventricular fibrillation, bigeminy, trigeminy, ventricular ectopic beats, bradycardia, tachycardia, a change in heart rate, a change in morphology of the ECG signal(s), any combination thereof, and/or the like.

In some embodiments, the wearable heart monitoring device 102 may include a plurality of therapy electrodes 108. For example, the wearable heart monitoring device 102 (e.g., controller 106 thereof) may determine the patient is experiencing a treatable cardiac atrial fibrillation based on identifying at least one atrial fibrillation event with the (trained) classifier, as described herein. Additionally or alternatively, the wearable heart monitoring device 102 (e.g., controller 106 thereof) may determine the patient is experiencing a treatable cardiac atrial fibrillation based on other criteria (e.g., other programming, logic, rules, and/or the like). In some embodiments, the wearable heart monitoring device 102 may deliver one or more therapeutic shocks to the patient via the therapy electrodes 108 (e.g., upon determining that the patient is experiencing a treatable cardiac atrial fibrillation), as described herein.

As shown in FIG. 4, at step 408, process 400 may include transmitting at least one communication based on the atrial fibrillation event(s). For example, the wearable heart monitoring device 102 (e.g., the processor(s) and/or controller 106 thereof) may transmit at least one communication based on the atrial fibrillation event(s) (e.g., to the remote computer system 140 and/or the gateway device 160), as described herein. Additionally or alternatively, the gateway device 160 (e.g., the processor(s) thereof) may transmit at least one communication based on the atrial fibrillation event(s) (e.g., to the remote computer system 140), as described herein.

In some embodiments, the at least one communication (e.g., communicated by the wearable heart monitoring device 102 and/or the gateway device 160) may include at least one further atypical ECG signal portion associated with the at least one atrial fibrillation event, as described herein.

As shown in FIG. 4, at step 410, process 400 may include receiving a retrained atrial fibrillation classifier. For example, the remote computer system 140 (and/or the wearable heart monitoring device 102 and/or the gateway device 160) may retrain the atrial fibrillation classifier and/or communicate the retrained atrial fibrillation classifier, as described herein. Additionally or alternatively, the wearable heart monitoring device 102 (and/or the gateway device 160) may receive the retrained the atrial fibrillation classifier, as described herein.

In some non-limiting embodiments, process 400 may include repeating at least some steps (e.g., steps 404-406, 404-408, 404-410, and/or the like). For example, at least some such steps may be repeated continuously, periodically, and/or the like. For example, the atypical ECG signal(s) may be received (step 404) continuously. Additionally or alternatively, the received atypical ECG signals may be analyzed using the atrial fibrillation classifier to continuously monitor the atypical ECG signal(s) to detect atrial fibrillation events (step 406). In some embodiments, upon detection of at least one atrial fibrillation event, the communication(s) may be transmitted, e.g., as often as atrial fibrillation events occur and/or are detected (step 408). In some embodiments, the atrial fibrillation classifier may be retrained (and/or communicated to the wearable heart monitoring device 102) periodically, continuously, and/or the like (step 410).

Figure 5:
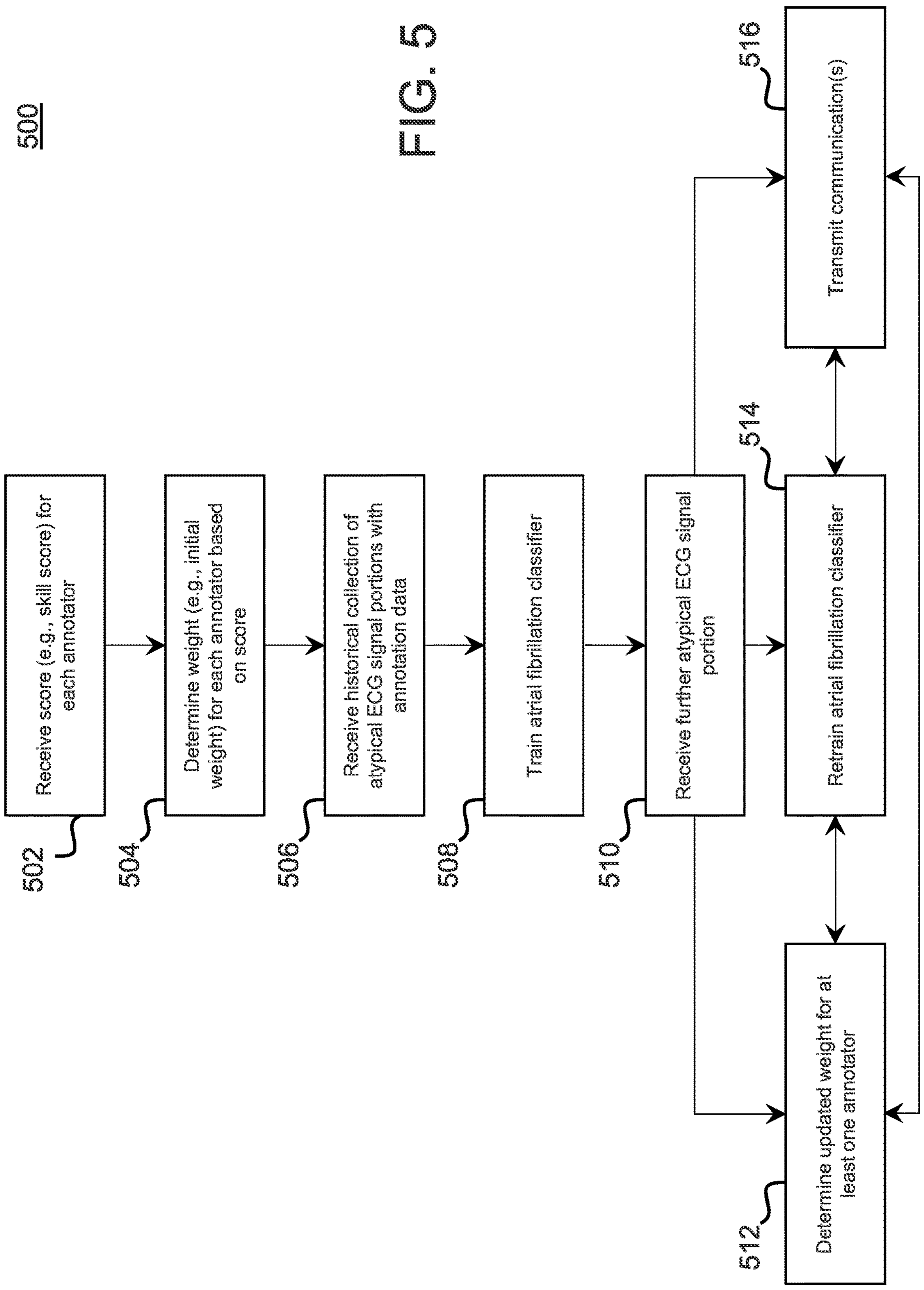
FIG. 5 shows an example flowchart of a process for cardiac diagnosis and/or monitoring with atypical ECG signals, according to some embodiments.

Referring now to FIG. 5, FIG. 5 is an example flowchart of a process 500 for cardiac diagnosis and/or monitoring with atypical electrocardiogram (ECG) signals, according to some embodiments. In some embodiments, one or more of the steps of the process 500 may be performed (e.g., completely, partially, and/or the like) by the remote computer system 140. In some non-limiting embodiments, one or more of the steps of the process 500 may be performed (e.g., completely, partially, and/or the like) by another system, another device, another group of systems, or another group of devices, separate from or including the remote computer system 140, such as the wearable heart monitoring device 102, the annotator device 150, the gateway device 160, and/or the like. The number and arrangement of steps shown in FIG. 5 are provided as an example. In some non-limiting embodiments, the process 500 may include additional steps, fewer steps, different steps, or differently arranged steps than those shown in FIG. 5.

As shown in FIG. 5, at step 502, process 500 may include receiving at least one score (e.g., a skill score) for each annotator of a plurality of annotators. For example, remote computer system 140 may receive a plurality of scores including a respective score for each respective annotator of a plurality of annotators, as described herein.

In some embodiments, the remote computer system 140 may receive a plurality of skill scores (e.g., initial skill scores, updated skill scores as described herein, and/or the like) including a respective skill score for each respective annotator (e.g., of a plurality of annotators), as described herein.

In some embodiments, the annotators may be given an initial test (e.g., a written test, a test on the annotator device 150, and/or the like), and each respective annotator's skill score may be based on that annotator's performance on the test (e.g., score, grade, assessment, and/or the like), as described herein. Additionally or alternatively, each annotator may annotate (e.g., with annotator device 150 and/or the like) at least a subset of the historical collection of ECG signal portions (e.g., in addition to, in lieu of, or as part of the initial test), and each respective annotator's skill score may be based on that annotator's performance (e.g., accuracy, precision with respect to other annotators, and/or the like) annotating the (subset of the) historical collection of ECG signal portions, as described herein.

As shown in FIG. 5, at step 504, process 500 may include determining a weight for each annotator based on the scores. For example, remote computer system 140 may determine a weight (e.g., initial weight, updated weight, and/or the like) for each respective annotator based on the respective scores (e.g., skill score) of the respective annotator.

In some embodiments, the remote computer system 140 may determine the respective weight for each respective annotator based on the plurality of scores. For example, the remote computer system 140 (and/or the wearable heart monitoring device 102 and/or the gateway device 160) may determine (e.g., calculate, look up, and/or the like) a weight for each respective annotator based on the respective skill score associated with the respective annotator.

In some embodiments, the respective weight for each respective annotator (e.g., of the plurality of annotators) may be based on a respective skill level of the respective annotator, as described herein. For example, the respective skill level for each respective annotator may include and/or be based on the skill score of the respective annotator.

In some embodiments, the skill score may include at least one of an integer value from one to four; an integer value from one to five; an integer value from one to ten; an integer value from one to 100; one of 25, 50, 75, or 100; a value from zero to one, and/or the like.

As shown in FIG. 5, at step 506, process 500 may include receiving a historical collection of atypical ECG signal portions with annotation data. For example, the remote computer system 140 may receive a historical collection of a plurality of atypical electrocardiogram (ECG) signal portions with annotation data, as described herein. For example, the annotation data may include at least one respective annotation for each respective atypical ECG signal portion of the plurality of atypical ECG signal portions.

In some embodiments, the remote computer system 140 may retrieve at least a portion of the historical collection of the plurality of atypical ECG signal and/or the annotation data from a data storage device, as described herein. In some embodiments, the remote computer system 140 may receive at least a portion of the historical collection of the plurality of atypical ECG signal and/or the annotation data from the annotator device 150, as described herein.

As shown in FIG. 5, at step 508, process 500 may include training the atrial fibrillation classifier. For example, the remote computer system 140 may train the atrial fibrillation classifier based on the historical collection of the plurality of atypical ECG signal portions with the annotation data and based on the weight data for the annotation data, as described herein.

In some embodiments, the remote computer system 140 training the atrial fibrillation classifier may include adjusting (e.g., by the remote computer system 140) a hyperparameter of a loss function of the atrial fibrillation (and/or atrial fibrillation) classifier based on the weight data, as described herein.

In some embodiments, the remote computer system 140 may train the atrial fibrillation classifier by generating, with the atrial fibrillation classifier, predicted atrial fibrillation event data (e.g., a prediction, a classification, a confidence score, and/or the like) for each atypical ECG signal portion of the historical collection (or a first subset thereof), as described herein. For example, the remote computer system 140 may input each atypical ECG signal portion of the historical collection (or a first subset thereof) into the atrial fibrillation classifier to generate predicted atrial fibrillation event data associated with at least one atrial fibrillation event (or with the lack of such event, e.g., NSR) predicted to be within the respective atypical ECG signal portion (e.g., forward propagation and/or the like), as described herein. The predicted atrial fibrillation event data may be compared (e.g., by the remote computer system 140) to the respective annotation data (e.g., from at least one annotator) for the respective atypical ECG signal portion, and/or the remote computer system 140 may determine (e.g., calculate) a loss based on the predicted atrial fibrillation event data and the annotation data. For example, the remote computer system 140 may calculate the loss based on the predicted atrial fibrillation event data, the respective annotation data, at least one loss function, and/or a hyperparameter of the loss function based on the weight associated with the respective annotator of the respective annotation data, as described herein. In some embodiments, the remote computer system 140 may update (e.g., adjust) the parameters (e.g., weights, connection values, and/or the like) of the atrial fibrillation classifier (e.g., the neural network(s) thereof) based on the loss (e.g., using back propagation, gradient calculations, and/or the like).

In some embodiments, a subset (e.g., a second subset) of the historical collection of ECG signal portions may be annotated (e.g., with the annotator device 150 and/or the like) by at least one annotator with a high skill level (e.g., an annotator with a high skill score; a committee of such annotators with high skill scores; an expert, such as a cardiologist, an electrophysiologist, a very experienced technician, and/or the like; a committee of such experts; any combination thereof, and/or the like). This (second) subset may be used for testing and validation of the trained model (e.g., atrial fibrillation and/or atrial fibrillation classifier) after training. For example, the performance (e.g., accuracy (ACC), loss (LOSS), area under curve (AUC), precision (PRE), recall (REC), F1 score (F1), specificity (SPEC), number of parameters (#P), latency (LAT) and/or the like) of the trained atrial fibrillation classifier may be tested, e.g., based on comparing the output (e.g., predicted atrial fibrillation event) of the trained atrial fibrillation classifier for each atypical ECG signal portion in the (second) subset with the annotation data from the (highly skilled) annotator(s), as described herein.

As shown in FIG. 5, at step 510, process 500 may include receiving at least one further atypical ECG signal portion. For example, the remote computer system 140 may receive (e.g., from wearable heart monitoring device 102, gateway device 160, annotator device 150, and/or a data storage device) at least one further atypical ECG signal portion and/or receive (e.g., from annotator device 150 and/or a data storage device) further annotation data from at least one annotator of the plurality of annotators (e.g., receive at least one further atypical ECG signal portion with further annotation data and/or the like), as described herein.

In some embodiments, the remote computer system 140 may analyze the further atypical ECG signal portion(s) to detect at least one atrial fibrillation event based on the atrial fibrillation classifier, as described herein.

In some embodiments, the remote computer system 140 may compare the further annotation data to the atrial fibrillation event(s), as described herein.

As shown in FIG. 5, at step 512, process 500 may include determining at least one updated weight for at least one annotator. For example, the remote computer system 140 may determine an updated weight for each of at least one annotator based on comparing the further annotation data to the at least one atrial fibrillation event, as described herein.

In some embodiments, the remote computer system 140 may be further configured to compare the further annotation data to at least one atrial fibrillation event detected based on the atrial fibrillation classifier. Additionally or alternatively, the remote computer system 140 may determine an updated weight for each respective annotator based on further annotation data and the atrial fibrillation event(s) (e.g., based on comparing the further annotation data to the atrial fibrillation events(s)).

As shown in FIG. 5, at step 514, process 500 may include retraining the atrial fibrillation classifier. For example, the remote computer system 140 may retrain the atrial fibrillation classifier based on the at least one further atypical ECG signal portion, the further annotation data, and/or the updated weight data.

In some embodiments, the remote computer system 140 may be further configured to retrain the atrial fibrillation classifier based on the further atypical ECG signal portion(s), the further annotation data, and the updated weight data. For example, retraining may be similar to training except at least some of the input data may be new and/or different (e.g., the further atypical ECG signal portion(s), the further annotation data, the updated weight data, and/or the like).

In some embodiments, the remote computer system 140 may be further configured to retrain the atrial fibrillation classifier based on the further atypical ECG signal portion(s), the further annotation data, and the weight data (e.g., the initial and/or original weight data).

As shown in FIG. 5, at step 516, process 500 may include transmitting at least one communication. For example, the remote computer system 140 may transmit at least one communication (e.g., based on comparing the further annotation data to the atrial fibrillation event(s)), as described herein.

In some embodiments, the remote computer system 140 may be further configured to compare the further annotation data to the at least one atrial fibrillation event detected based on the atrial fibrillation classifier and/or transmit at least one further communication based on the further annotation data and the at least one atrial fibrillation event (e.g., based on comparing the further annotation data to the at least one atrial fibrillation event), as described herein. For example, the at least one further communication may include a recommendation to retest one or more of the annotator(s), a recommendation to increase the respective skill score of one or more of the annotator(s), a recommendation to decrease the respective skill score of one or more of the annotator(s), any combination thereof, and/or the like, as described herein.

Figure 6:
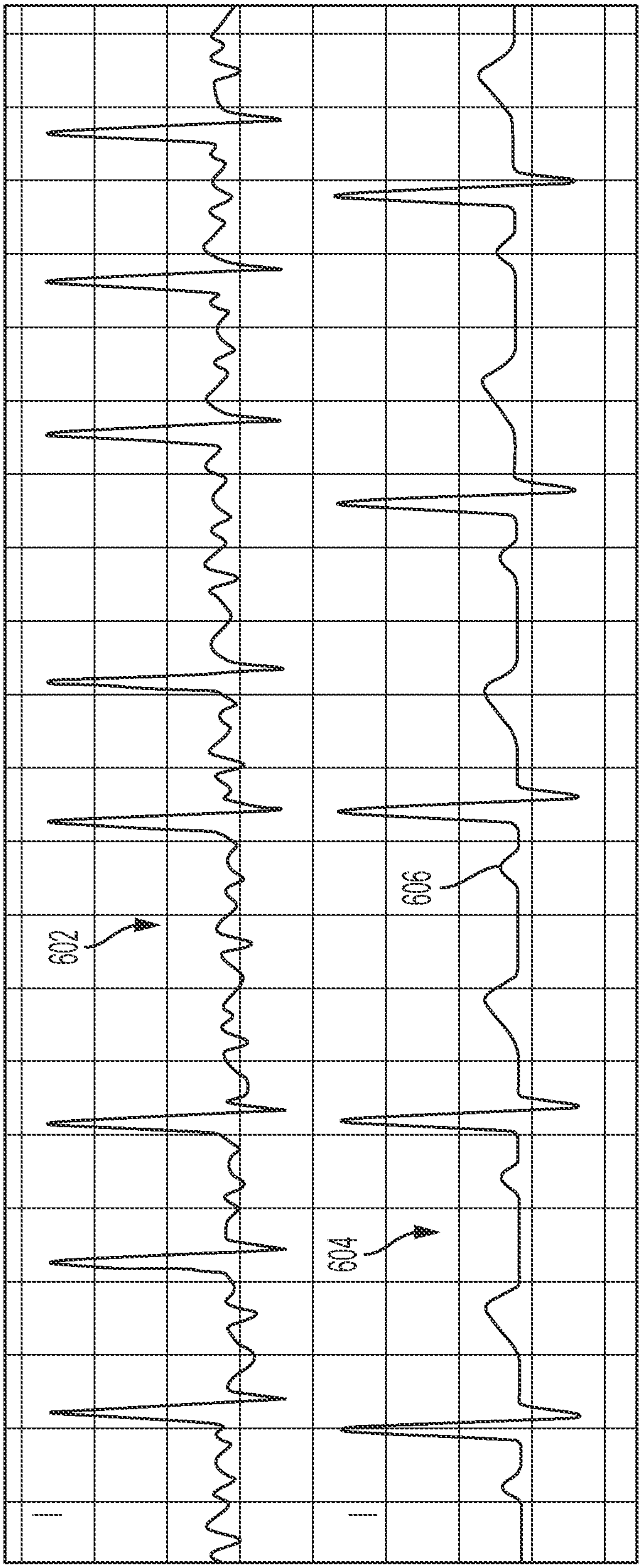
FIG. 6 shows an example graph of example atypical ECG signal portions, according to some embodiments.

Referring now to FIG. 6, FIG. 6 is an illustration of an example graph 600 of atypical ECG signal portions, according to some embodiments. As shown in FIG. 6, graph 600 may include first atypical ECG signal portion 602 and second atypical ECG signal portion 604. The number and arrangement of atypical ECG signal portions shown in FIG. 6 are provided as an example. In some non-limiting embodiments, the graph 600 may include additional atypical ECG signal portions, fewer atypical ECG signal portions, different atypical ECG signal portions, or differently arranged atypical ECG signal portions than those shown in FIG. 6.

In some embodiments, first atypical ECG signal portion 602 may be associated with an arrhythmia event. For example, first atypical ECG signal portion 602 may be associated with an atrial fibrillation event. In some embodiments, second atypical ECG signal portion 604 may be associated with NSR (e.g., no arrhythmia). For example, second atypical ECG signal portion 604 may include a P wave. In contrast, first atypical ECG signal portion 602 may not have a P wave, for example, because of the atrial fibrillation event.

Figure 7:
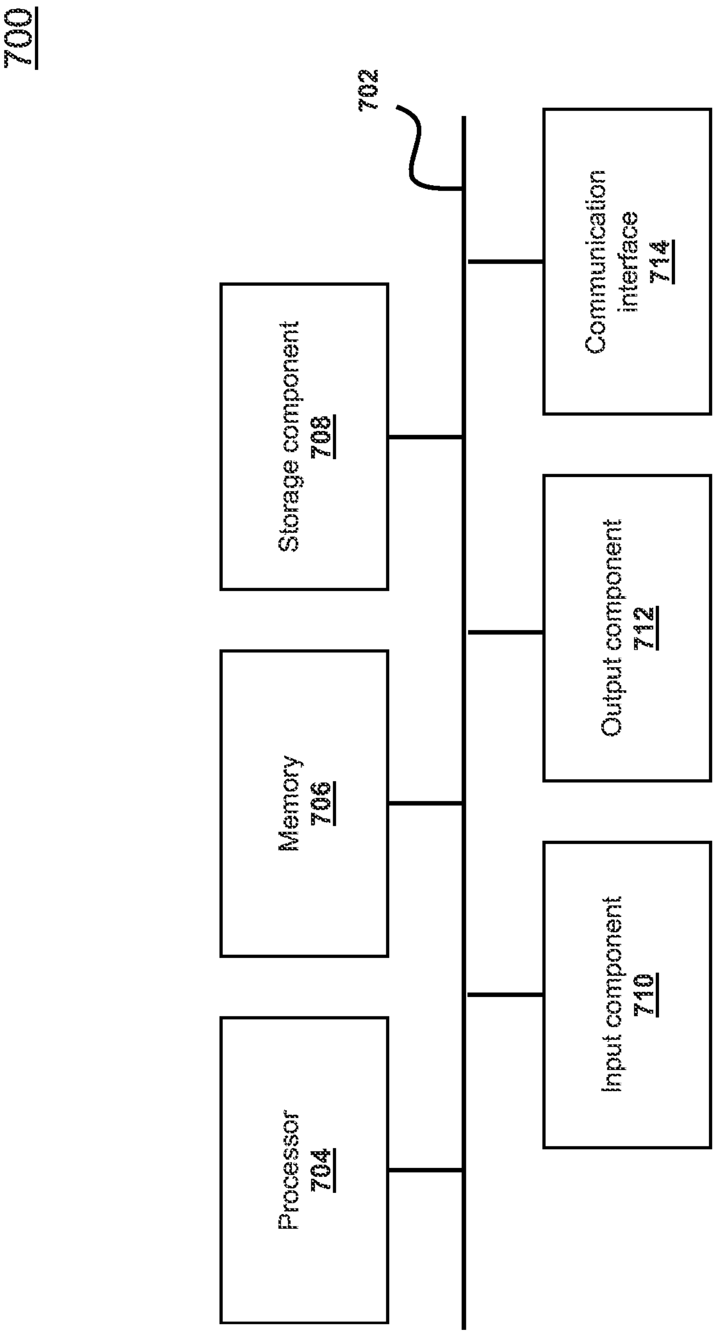
FIG. 7 shows an example block diagram of components of one or more computing devices on which the processes described herein can be implemented, according to some embodiments.

Referring now to FIG. 7, FIG. 7 is a diagram of example components of a computing device 700, according to some embodiments. The computing device 700 may correspond to one or more devices of the wearable heart monitoring device 102, the remote computer system 140, the annotator device 150, and/or the gateway device 160. In some non-limiting embodiments, the wearable heart monitoring device 102, the remote computer system 140, the annotator device 150, and/or the gateway device 160 may include at least one computing device 700 and/or at least one component of the computing device 700. As shown in FIG. 7, the computing device 700 may include a bus 702, a processor 704, a memory 706, a storage component 708, an input component 710, an output component 712, and/or a communication interface 714.

The bus 702 may include a component that permits communication among the components of the computing device 700. In some non-limiting embodiments, the processor 704 may be implemented in hardware, software, and/or a combination of hardware and software. For example, the processor 704 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), an application-specific standard product (ASSP), a system-on-a-chip (SOC), a tensor processing units (TPU), and/or the like), and/or the like, which can be programmed to perform a function. The memory 706 may include random access memory (RAM), read only memory (ROM), and/or another type of dynamic or static storage device (e.g., flash memory, magnetic memory, optical memory, and/or the like) that stores information and/or instructions for use by the processor 704.

The storage component 708 may store information and/or software related to the operation and use of the computing device 700. For example, the storage component 708 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

The input component 710 may include a component that permits the computing device 700 to receive information, such as via user input (e.g., a touch screen display, a keyboard, a keypad, a mouse, a button, a switch, a microphone, a camera, and/or the like). Additionally or alternatively, the input component 710 may include a sensor for sensing information (e.g., an ECG electrode and/or associated circuitry, a heart rate sensor, an oxygen saturation sensor, an actigraphy sensor (e.g., an accelerometer), a snoring sensor (e.g., a microphone, a vibration sensor, and/or the like), a chest motion sensor, a body position sensor, an arm position sensor, a sleep stage sensor, a global positioning system (GPS) component, an accelerometer, a gyroscope, an actuator, an electrode, any combination thereof, and/or the like). The output component 712 may include a component that provides output information from computing device 700 (e.g., a display, a speaker, one or more light-emitting diodes (LEDs), and/or the like).

The communication interface 714 may include a transceiver-like component (e.g., a transceiver, a receiver and transmitter that are separate, and/or the like) that enables the computing device 700 to communicate with other devices, such as via a wired connection, a wireless connection, or a combination of wired and wireless connections. The communication interface 714 may permit the computing device 700 to receive information from another device and/or provide information to another device. For example, the communication interface 714 may include an Ethernet interface, an optical interface, a coaxial interface, an infrared interface, a radio frequency (RF) interface, a universal serial bus (USB) interface, a Wi-Fi® interface, a Bluetooth® interface, a Zigbee® interface, a cellular network interface, and/or the like.

The computing device 700 may perform one or more processes described herein. The computing device 700 may perform these processes based on the processor 704 executing software instructions stored by a computer-readable medium, such as the memory 706 and/or the storage component 708. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into the memory 706 and/or the storage component 708 from another computer-readable medium or from another device via the communication interface 714. When executed, software instructions stored in the memory 706 and/or the storage component 708 may cause the processor 704 to perform one or more processes described herein. Additionally or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 7 are provided as an example. In some non-limiting embodiments, the computing device 700 may include additional components, fewer components, different components, or differently arranged components than those shown in FIG. 7. Additionally or alternatively, a set of components (e.g., one or more components) of the computing device 700 may perform one or more functions described as being performed by another set of components of the computing device 700.

Figure 8:
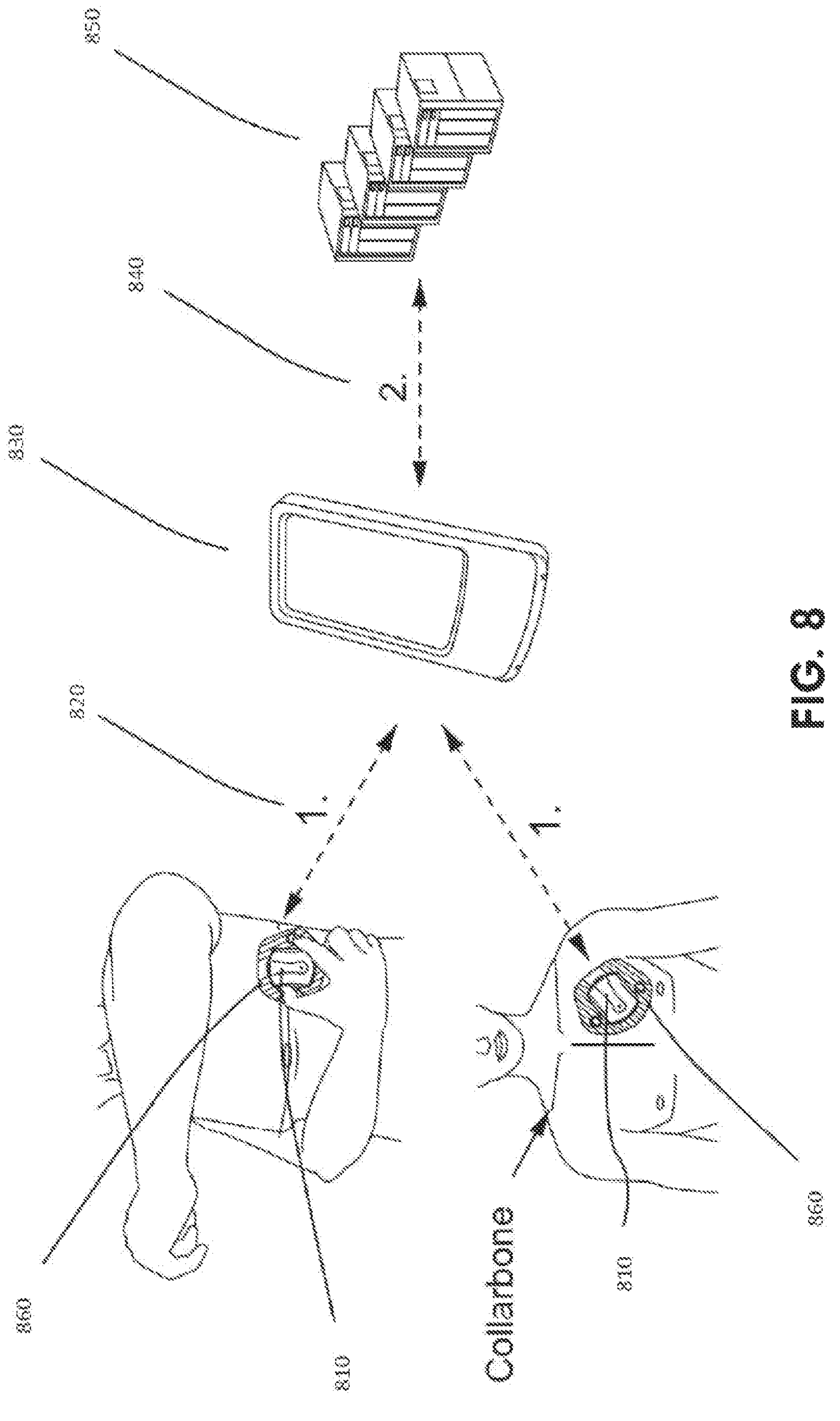
FIG. 8 shows an example schematic illustration of measurement and transmission of physiological data acquired via body-worn sensor(s) (e.g., external heart monitoring device(s)) disclosed herein, according to some embodiments.

Referring now to FIG. 8, FIG. 8 shows an example wearable heart monitoring device, e.g., an arrhythmia and fluid monitoring system that includes a physiological monitoring device 810, hereinafter referred to as "sensor(s)", and a wearable patch 860 configured to place the sensor(s) on, or in the vicinity of, a surface of a body (e.g., a patient). Further, the system may include a portable data transmission device (gateway) 830 that is capable of continuously transmitting data acquired by the sensor(s) 810 to a remote computer system (e.g., one or more servers 850) for processing and/or analysis. Thus, for example, the gateway device 830 may transmit to the server 850 data received from the sensor(s) 810 with little or no delay or latency. To this end, in the context of data transmission between the device(s) 810 and server(s) 850, "continuously" for the present disclosure includes continuous (without interruption), or near continuous, i.e., within one minute after completion of a measurement by and/or an occurrence of an event on the device. Continuity may also be achieved by repetitive successive bursts of transmission, e.g., high-speed transmission. Similarly, the term "immediate," according to the present disclosure, includes as occurring or done at once, or near immediate i.e., within one minute after the completion of a measurement by and/or an occurrence of an event occurring on the device.

Further, in the context of physiological data acquisition by the device(s) 810, "continuously" also includes uninterrupted collection of sensor data, such as ECG data and/or accelerometer data, with clinical continuity. In this case, short interruptions in data acquisition of up to 1-second several times an hour or longer interruptions of a few minutes several times a day may be tolerated and can still be seen as "continuous". As to latency as a result of such a continuous scheme as described herein, this relates to the overall budget of response time which can amount to between about 5 to about 15 minutes overall response time (e.g., time from when an event onset is detected to when a notification regarding the event is issued). As such, transmission/acquisition latency would, therefore, be in the order of minutes.

Further, the wearable devices described herein are configured for long-term and/or extended use or wear by, or attachment or connection to a patient. For example, devices as described herein may be capable of being used or worn by, or attached or connected to a patient, without substantial interruption, for example, up to 24 hours or beyond (e.g., weeks, months, or even years). In some implementations, such devices may be removed for a period of time before use, wear, attachment, or connection to the patient is resumed, e.g., to change batteries, carry out technical service, update the device software or firmware, and/or to take a shower or engage in other activities, without departing from the scope of the examples described herein.

In some embodiments, the transmission of data/signals 820 between the sensor(s) 810 and the gateway device 830 may be one way (e.g., from the sensor(s) 810 to the gateway device 830) or the transmission may be bi-directional. Similarly, the transmission of data/signals 820 between the gateway device 830 and the server 850 may be one way (e.g., from the gateway device 830 to the server 850) or bi-directional. The system may also include a charger (not shown) for powering the electronics of the system.

In some embodiments, the sensor(s) 810 is configured to monitor, record, and transmit to the gateway device 830 physiological data about the wearer of the sensor(s) 810 continuously. In particular, the sensor(s) 810 may not interrupt monitoring and/or recording additional data while transmitting already acquired data to the gateway device 830. Put another way, in some embodiments, both the monitoring/recording and the transmission processes occur at the same time or at least nearly at the same time.

As an another example, if the sensor(s) 810 does suspend monitoring and/or recording additional data while it is transmitting already acquired data to the gateway device 830, the sensor(s) 810 may then resume monitoring and/or recording additional data prior to all the already acquired data being transmitted to the gateway device 830. In other words, the interruption period for monitoring and/or recording may be less in comparison to the time it takes to transmit the already acquired data (e.g., between about 0% to about 80%, about 0% to about 60%, about 0% to about 40%, about 0% to about 20%, about 0% to about 10%, about 0% to about 5%, including values and subranges therebetween), facilitating the near-continuous monitoring and/or recording of additional data during transmission of already acquired physiological data. For example, in one specific scenario, when a measurement time duration is around 2 minutes, any period of suspension or interruption in the monitoring and/or recording of subsequent measurement data may range from a just few milliseconds to about a minute. Example reasons for such suspension or interruption of data may include allowing for the completion of certain data integrity and/or other on-line tests of previously acquired data, as described in further detail below. If the previous measurement data has problems, the sensor(s) 810 can notify the patient and/or remote technician of the problems so that appropriate adjustments can be made.

In some embodiments, the bandwidth of the link 820 between the sensor 810 and the gateway device 830 may be larger, and in some instances significantly larger, than the bandwidth of the acquired data to be transmitted via the link 820 (e.g., burst transmission). Such embodiments ameliorate issues that may arise during link interruptions, periods of reduced/absent reception, etc. In some embodiments, when transmission is resumed after interruption, the resumption may be in the form of last-in-first-out (LIFO). The gateway device 830 can be configured to operate in a store and forward mode where the data received from the sensor 810 is first stored in an onboard memory of the gateway device 830 and then forwarded to the external server. For example, such a mode can be useful where the link 820 with the server may be temporarily unavailable. In some embodiments, the gateway device 830 can function as a pipe line and pass through data from the sensor 810 immediately to the server 850. In further examples, the data from the sensor may be compressed using data compression techniques to reduce memory requirements, as well as transmission times and power consumptions.

In some embodiments, the sensor(s) 810 may be configured to monitor, record, and transmit some data in a continuous or near-continuous manner as discussed above, while monitoring, recording, and transmitting some other data in a non-continuous manner (e.g., periodically, no-periodically, etc.). For example, the sensor(s) 810 may be configured to record and transmit ECG data continuously or nearly continuously while radio-frequency (RF) based measurements and/or transmissions may be periodic. For example, ECG data may be transmitted to the gateway device 830 (and subsequently the server 850) continuously or near-continuously as additional ECG data is being recorded, while RF-based measurements may be transmitted once the measuring process is completed.

Monitoring and/or recording of physiological data by the sensor(s) 810 may be periodic, and in some embodiments, may be accomplished as scheduled (i.e., periodically) without delay or latency during the transmission of already acquired data to the gateway device 830. For example, the sensor(s) 810 may acquire physiological data from the patient (i.e., the wearer of the sensor(s) 810) in a periodic manner and transmit the data to the gateway device 830 in a continuous manner, as described above.

The sensor(s) 810 may be configured to transmit the acquired data to the servers 850 instead of, or in addition to, transmitting the data to the gateway device 830. The sensor(s) 810 may also be configured to store some or all of the acquired physiological data. In some embodiments, the transmission of data from the sensor(s) 810 to the gateway device 830 may be accomplished wirelessly (e.g., Bluetooth®, etc.) and/or via a wired connection, e.g., 820. The transmission of data from the gateway device 830 to the server 850 may also be accomplished wirelessly (e.g., Bluetooth®-to-TCP/IP access point communication, Wi-Fi®, cellular, etc.) and/or via a wired connection, e.g., 840.

As mentioned above, in some embodiments, the transmission of data and/or signals occurs via two links 820, 840, the links between the sensor(s) 810 and the gateway device 830 (e.g., Bluetooth® link) and between the gateway device 830 and the server 850 (e.g., Wi-Fi®, cellular). The Bluetooth® link can be a connection bus for sensor(s) 810 and server 850 communication, used for passing commands, information on status of the microprocessor of the sensor(s) 810, measurement data, etc. In some embodiments, the microprocessor of the sensor(s) 810 may initiate communication with the server 850 (and/or the gateway device 830), and once connection is established, the server 850 may be configured to initiate some or all other communications. In some embodiments, the gateway device 830 may be configured to conserve the power available to the sensor(s) 810, device 830, and/or servers 850. For example, one or both links 820, 840 may enter power saving mode (e.g., sleep mode, off-state, etc.) when the connections between the respective devices/servers are not available. As another example, the transmission of data may also be at least temporarily interrupted when the link quality (e.g., available bandwidth) is insufficient for at least a satisfactory transmission of the data. In such embodiments, the gateway device 830 may serve as a master device in its relationship to one or both of the sensor(s) 810 and the server 850.

In some embodiments, the gateway device 830 may be considered as a simple pipe, the sensor-gateway device-server path may be defined as a single link, i.e., the link performance may depend on the bottleneck between the sensor-gateway device and gateway device-server links. In some embodiments, at least the main bottleneck may be the gateway device-server link, since the gateway device is carried by the patient in close proximity to the device, while the gateway device-server link (e.g., cellular or Wi-Fi® coverage) is expected to be variable. In some embodiments, a "best effort delivery" quality-of-service may be sufficient for the Bluetooth link and/or the TCP/IP link, since the transmitted data is processed (with some latency, for example) and is used for displaying notifications (for example, instead of being presented online to a monitoring center). In some embodiments, a single gateway device 830 may be configured to serve a plurality of sensors, i.e., the plurality of sensors may be connected to a single gateway device 830 via respective links. In some embodiments, there may be a plurality of gateway devices 830 serving one or more sensor(s), i.e., each sensor of the one or more sensors may be connected to a plurality of gateway devices 830 via respective links.

In some embodiments, the transmission links 820, 840 may be configured to withstand co-existence interference from similar devices in the vicinity and from other devices using the same RF band (e.g., Bluetooth®, Cellular, Wi-Fi®). Standard Bluetooth® protocol and/or standard TCP/IP protocols, as well as the addition of cyclic redundancy check to the transmitted data, may be used to address any issue of interference. Further, to preserve the security of wireless signals and data, in some embodiments, data transfer between the sensor and the server may be done using a proprietary protocol. For example, TCP/IP link may use SSL protocol to maintain security, and the Bluetooth® link may be encrypted. As another example, UDP/HTTP may also be used for secure transmission of data. In some embodiments, only raw binary data may be sent, without any patient identification.

Examples of the types of physiological data that the arrhythmia and fluid monitoring sensor(s) 810 is configured to monitor and/or acquire from a patient wearing the sensor(s) 810 include one or more of electrocardiogram (ECG) data, thoracic impedance, heart rate, respiration rate, physical activity (e.g., movement), and patient posture. In some embodiments, the physiological data may be acquired and/or transmitted to the gateway device 830 or the server 850 by the sensor(s) 810 in a manner that is continuous, periodic, or as instructed by received signals (e.g., as instructed by signal received from the gateway device 830 and/or the server 850). For example, the wearer of the sensor or another party (e.g., a health professional) may activate the sensor(s) 810 and the sensor may start monitoring and/or recording any one of the above-noted physiological parameters automatically without further input from the wearer or the party. The sensor(s) 810, or the arrhythmia and fluid monitoring system in general, may request further input (e.g., selection of a setting identifying the physiological parameter to be measured) before initiating the monitoring and/or recording of physiological data. In any case, once the monitoring and/or recording starts, the sensor(s) 810 may transmit the acquired data to the gateway device 830 and/or the server 850 in at least a continuous manner as described above, for example.

In some embodiments, one or more of the above-noted physiological parameters may be measured periodically, and the sensor(s) 810 may transmit the measurements to the gateway device 830 in at least a continuous manner, as acquired. For example, the periodic measurements may proceed as scheduled and the transmission to the gateway device 830 may occur with little or no delay or latency after data is acquired.

In some embodiments, the sensor(s) 810, or the arrhythmia and fluid monitoring system in general, may be configured to operate some, but not all, of the available features discussed above. For example, the sensors 810 may be configured to monitor and/or acquire one or more of ECG data, thoracic impedance, heart rate, respiration rate, physical activity (e.g., movement), patient posture, etc., but not the others. For instance, the sensors may be configured to monitor and/or acquire data, such as ECG data, but not respiration rate, physical activity (e.g., movement), patient posture. Such embodiments may be effected, for example, by including controls in the sensors and/or the system that separately control components of the sensors/system responsible for the features. For example, the arrhythmia and fluid monitoring system may include controls (e.g., power buttons) that separately control the accelerometer and the ECG components of the sensor. By switching on the accelerometer power control and switching off the ECG power control, in some embodiments, one may allow the monitoring and/or acquiring of data related to respiration rate, physical activity, and patient posture while deactivating the monitoring and/or acquiring of ECG data.

In some embodiments, an adhesive patch 860 may be used to attach the sensor(s) 810 to a surface of the body of a patient. FIGS. 9A-9E show the sensor 970 disclosed herein, a patch 910 configured to attach the sensor 970 to a patient's body or at least hold the sensor 970 in proximity to skin of the body, and an illustration of a method of attaching the sensor 970 to the patch 910, according to some embodiments. The patch 910 may include a patch frame 930 (e.g., plastic frame) delineating the boundary of the region of the patch 910 that is configured for housing the sensor 970. The patch 910 may be disposable (e.g., single- or few-use patches), and may be made of biocompatible, non-woven material. In some embodiments, the sensor 970 may be designed for long-term usage. In such embodiments, the connection between the patch 910 and the sensor 970 may be configured to be reversible, i.e., the sensor 970 may be configured to be removably attached to the patch 910. For example, the sensor 970 may include components such as snap-in clips 940 that are configured to secure the sensor 970 to the patch 910 (e.g., the patch frame 930) upon attachment (and released the sensor 970 from the patch 910 when separation is desired). The sensor 970 may also include positioning tabs 960 that facilitate the attachment process between the sensor 970 and the patch 910. In some embodiments, the patch 910 may be designed to maintain attachment to skin of a patient for several days (e.g., in the range from about 4 days to about 10 days, from about 5 days to about 7 days, etc.).

In some embodiments, the patch 910 may include additional components that facilitate or aid with the monitoring and/or recording or acquiring of physiological data by the sensor 970. For example, the patch 910 may include conductive elements such as one or more ECG electrodes 920 (e.g., a single lead, two leads, etc.) that can be used when recording ECG data from the surface (e.g., skin contacted directly or through a covering) of a patient's body. The electrodes 920 may be coupled to the sensor 970 by dedicated wiring within the patch 910. In some embodiments, the ECG electrodes 920 may have a sampling rate in the range from about 950 Hz to about 500 Hz, from about 300 Hz to about 450 Hz, from about 350 Hz to about 400 Hz, including values and subranges therebetween. In some embodiments, the ECG signal may be sampled after bandpass filtering by a 12 bit ADC. During normal operation, data may be transferred to the server "as-is" and can then be used by the server algorithms for analysis. In some embodiments, an internal algorithm allows for real-time evaluation of the ECG signal quality upon each attachment of the device to the patient ("attachment test").

Figure 9C:
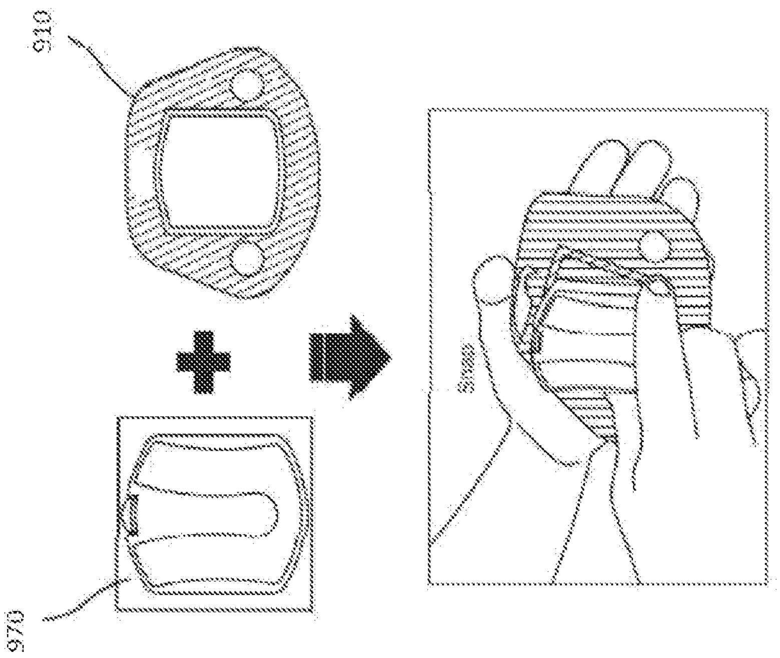
FIGS. 9A-9E show an example sensor(s) (e.g., of external heart monitoring device(s)) disclosed herein, a patch configured to hold the sensor(s) in proximity to a body, and attachment of a patch housing a sensor(s) onto skin of a patient, according to some embodiments.
Figure 9A:
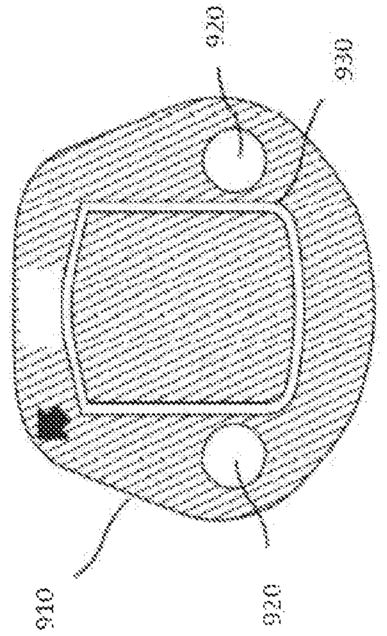
Figure 9B:
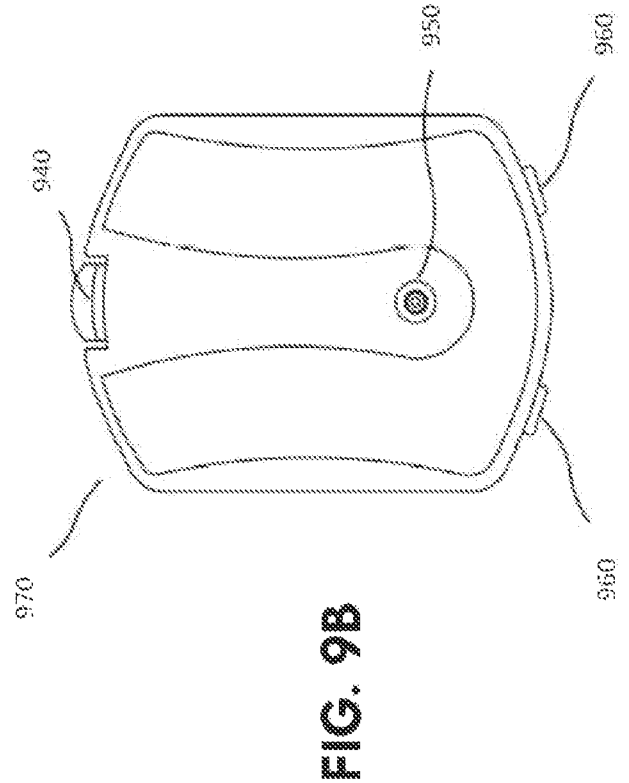
Figure 9E:
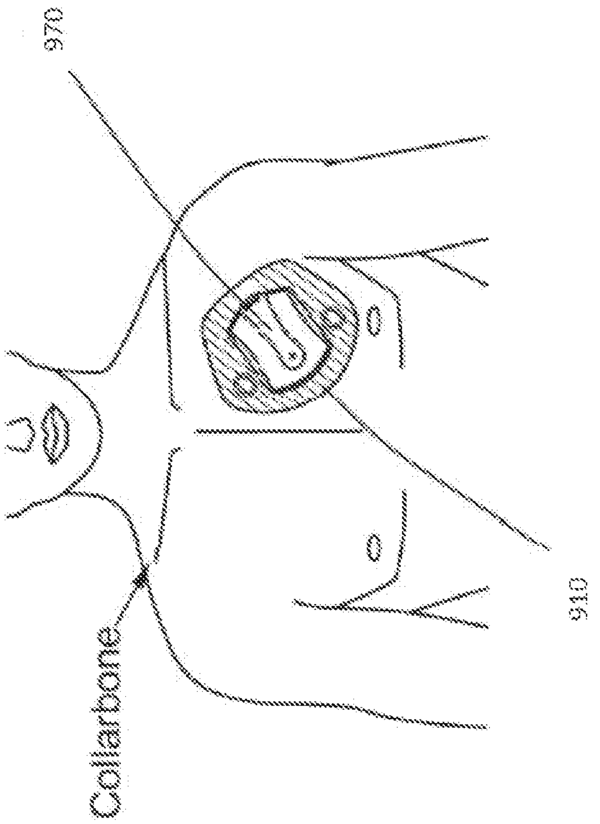
Figure 9D:
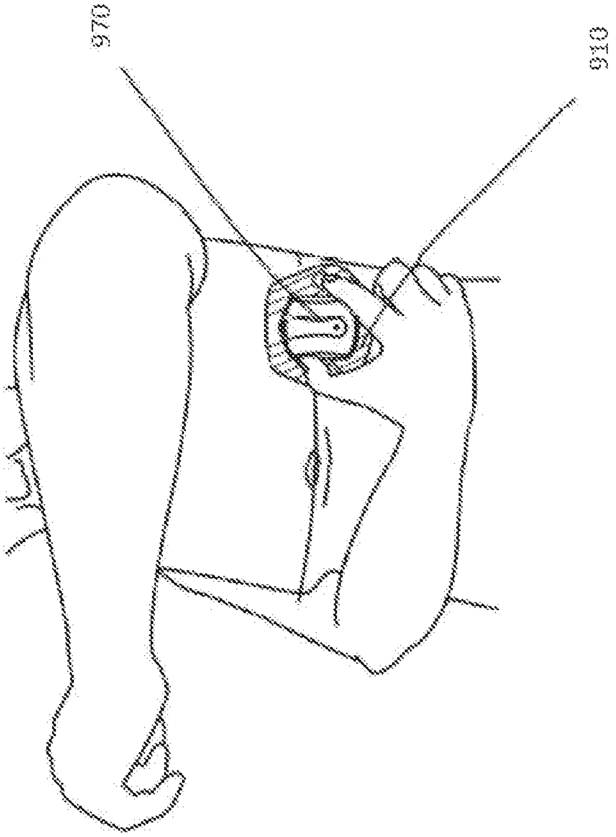

Examples of locations on a surface of a patient's body at which a patch may be placed are shown in FIGS. 9D and 9E, where a patch 910 housing sensor 970 is shown as placed at/on the side (below armpit, for example) (FIG. 9D) and upper chest (FIG. 9E) of the torso of a patient. It is to be noted that the patch 910 may be placed on any part of the surface of a patient's body that allows for efficient monitoring and recording of a physiological data (e.g., area of skin that allows for uniform attachment of the patch 910 to the skin). For example, one may place the patch 910 under an armpit at the nipple level for performing lung fluid level measurements. With respect to ECG measurements, the ECG signal at this location may be represented as the difference between standard V5 and V6 leads of an ECG.

Figure 10A:
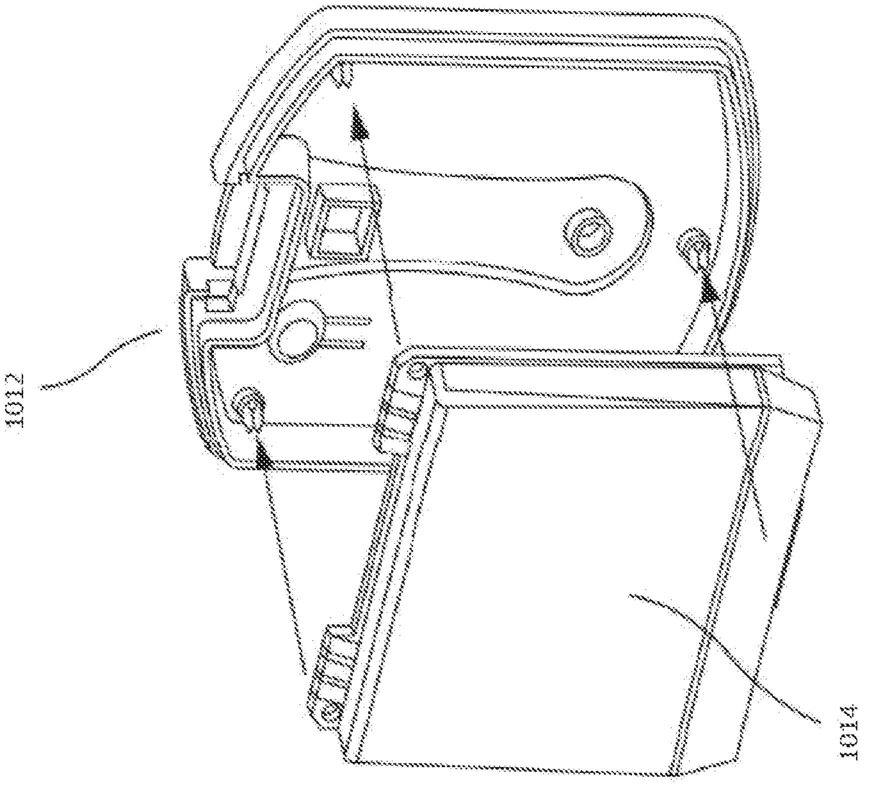
FIGS. 10A-10C show example front, back and exploded views, respectively, of the sensor(s) (e.g., of external heart monitoring device(s)) disclosed herein, according to some embodiments.
Figure 10B:
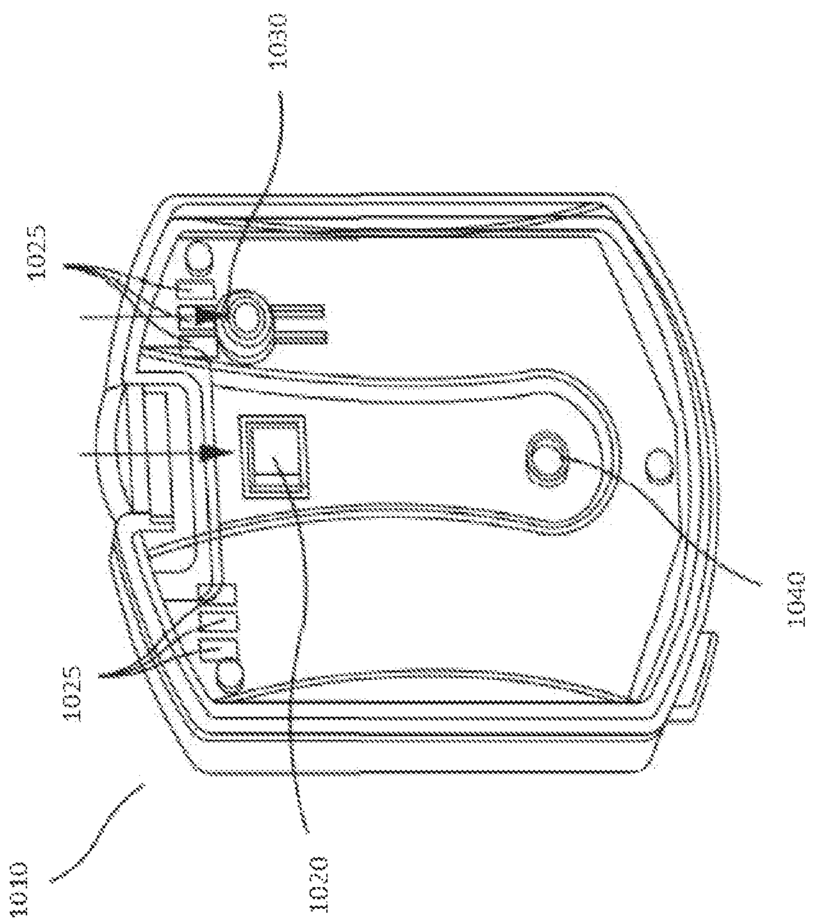
Figure 10C:
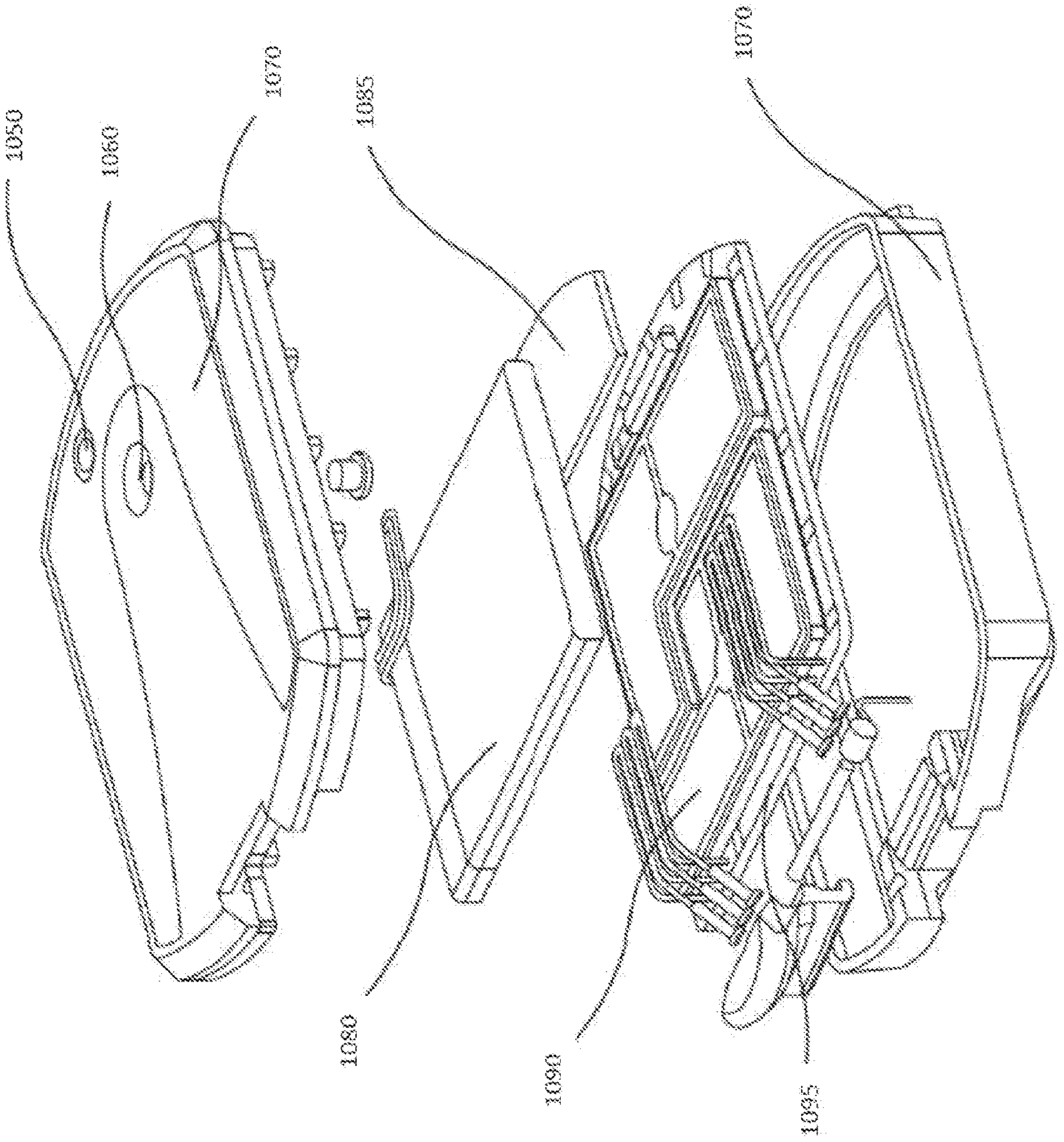

With reference to FIGS. 10A-10C, in some embodiments, front, back, and exploded views, respectively, of the sensor(s) disclosed herein are shown. FIG. 10A shows the front 1012 and back 1014 covers of the sensor 1010 (labelled as top and bottom covers 1070 in FIG. 10C). In some embodiments, such covers may couple to each other to seal the electrical components of the sensor 1010 from the surrounding environment (e.g., electrical sealing). In such embodiments, metallic tabs 1025 may protrude outside the covers to provide electrical connection for situations such as performing ECG measurements, charging power source, and/or the like.

FIG. 10B shows that the sensor 1010 may include one or more indicators that identify the status of the sensor 1010 to the user of the sensor 1010. Examples of such indicators include but are not limited to light indicator 1040 (e.g., a light emitting diode (LED) indicator) and sound indicators 1020. In some embodiments, the indicators 1020, 1040 provide feedback on the status of the sensor 1010 and components thereof, such as the charging and/or power level of the power source of the sensor 1010 (e.g., a battery), the attachment level of the sensor 1010 to the patch 910, the attachment level of the patch 910 to the surface of the body to which the patch 910 is attached, etc. As another example, the sensor 1010 may respond by blinking (e.g., via the light indicator 1040) or buzzing (e.g., via the sound indicator 1020) in response to an engagement by a patient to indicate possible symptoms.

In some embodiments, FIG. 10C provides an exploded view of the sensor 1010 depicting at least some of the components of the sensor 1010. For example, the sensor 1010 may comprise a power source such as a battery 1080, a light indicator 1060, a button 1050 for facilitating the interaction of a patient, a healthcare provider, and/or a technician with the sensor 1010, a wireless communications circuit 1085, a radio frequency shield 1090 (such as a metallic cover, e.g., to prevent interferences with the ECG processing and other digital circuitry), a digital circuitry board 1095, and/or the like. FIG. 10C shows a Bluetooth unit as an example of a wireless communications circuit 1085, although in addition to or alternatively to the Bluetooth unit, other modules facilitating other types of communications (examples of which include Wi-Fi®, cellular, etc.) may be included in the sensor 1010.

In some embodiments, the sensor 1010 may also include input interfaces such as buttons for interfacing with a user. For example, the sensor 1010 may include a button 1030/1050 that allows a patient or a health care professional to activate or deactivate the sensor 1010. Such input interfaces may be configured to avoid or at least minimize unintended interactions with a user. For example, a button 1030/1050 may be sized and shaped to avoid accidental activation (e.g., the button may be configured to require activation by being pushed in with an external object). This button 1030/1050 may be used to reset the sensor 1010 as well as pair the sensor 1010 to the gateway device and initiate communication. In some embodiments, the input interface of the sensor 1010 may include a touch screen configured to receive input from a user and/or provide information back to the user. For example, the input may allow the user to set the sensor in an "airplane mode," i.e., for example by deactivating any wireless communication (e.g., Wi-Fi, Bluetooth, etc.) with external devices and/or servers. For example, the button 1030/1050 can be implemented as a magnetic switch, e.g., an embedded magnetic switch, instead of a physical button. Such an implementation can be useful for designing the housing of the device and avoid exposing button components to the environment.

Figure 11A:
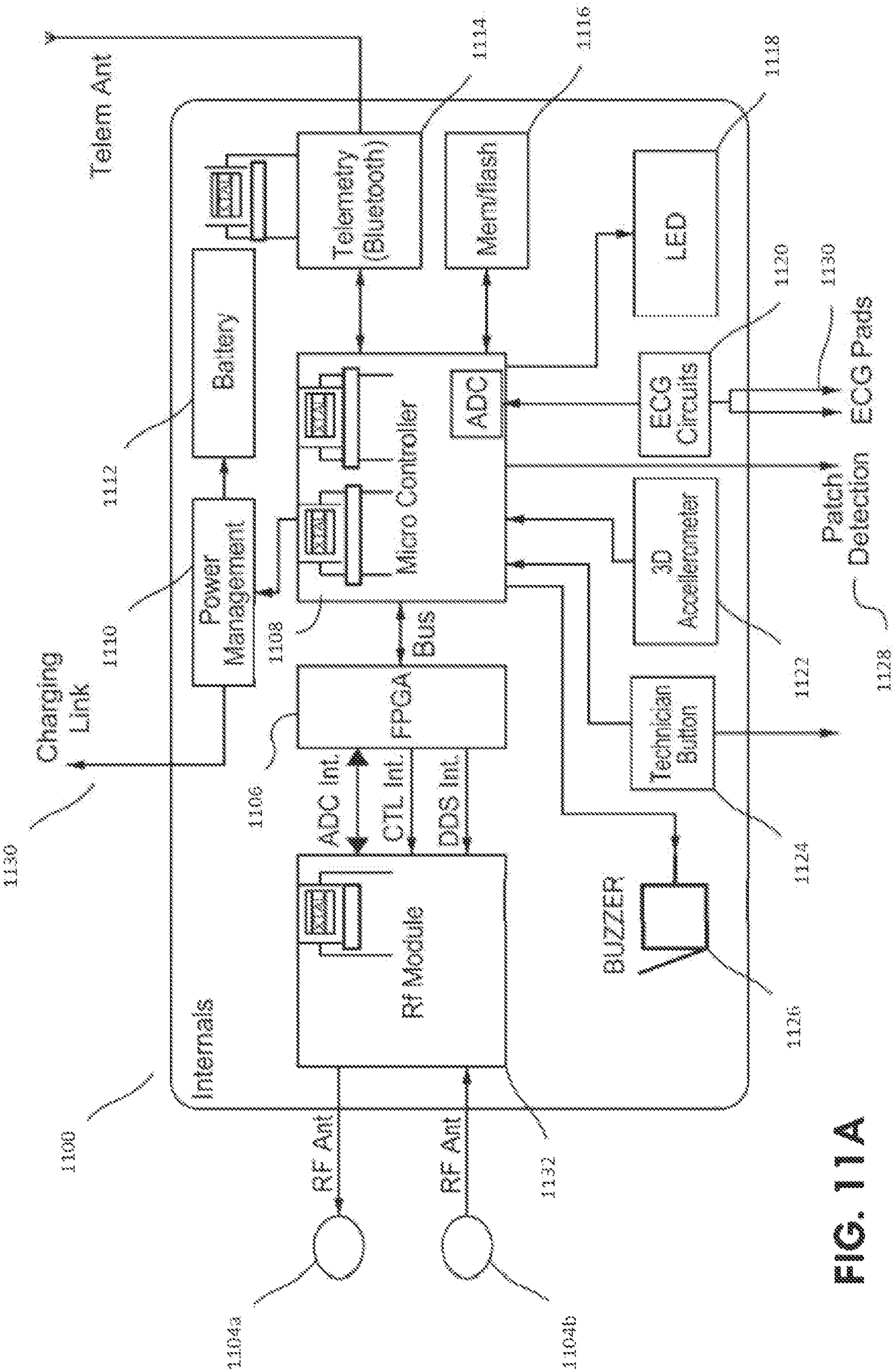
FIG. 11A shows an example illustration of device electronics architecture for measurements and transmission of patient physiological data (e.g., biometric data), according to some embodiments.

In some embodiments, as described above, the disclosed sensor 1010 is configured to monitor and/or acquire data on physiological parameters including but not limited to electrocardiogram (ECG) data, thoracic impedance, heart rate, respiration rate, physical activity, posture, and/or the like. To that effect, the sensor 1010 and/or the patch housing the sensor 1010 may include components that facilitate or undertake the monitoring and/or recording of at least some of these parameters. For example, as noted above, the patch housing the sensor 1010 may include ECG electrodes coupled to the sensors 1010 to facilitate the monitoring and/or acquiring of ECG data. As shown in FIG. 11A, which shows an example embodiment of device electronics architecture for measurements and transmission of patient physiological data, the sensor 1010 includes EGG processing circuitry configured to couple to the ECG electrodes embedded in the patch housing the sensor 1010 itself. The ECG processing circuitry is configured to, for example, perform filtering, amplification, and/or removal of noise, low frequency variations in the signal, and other signal artifacts.

As another example, the sensor may include a radio frequency (RF) antenna for directing electromagnetic waves into a body of a patient and receiving waves that are scattered and/or reflected from internal tissues. Further, the sensor may include RF circuitry or module configured to process the received waves so as to determine some properties of the tissues that are on the path of the transmitted and/or scattered/reflected waves. For example, the antenna may direct RF waves towards a lung of a patient and the RF circuitry may analyze the scattered/reflected waves to perform an RF-based measurement of the lung fluid level of the patient. FIG. 11A shows an example embodiment of a sensor comprising RF antennas, an RF module and circuits for controlling the module (e.g., field-programmable gate array (FPGA) circuits).

With reference to FIG. 11A, in some embodiments, the sensor 1100 includes external interfaces such as but not limited to RF antennas (e.g., bi-static) 1104*a*, 1104*b* for transmitting and receiving RF signals, a button or switch 1124 for activating or deactivating the sensor 1100, an LED 1118 and a buzzer 1126 for providing light and audio feedback to a user of the sensor 1100, a battery charging link 1130 coupled to a power management module 1110 for charging an onboard power source such as a battery 1112, and ECG pads 1130 for recording synchronization signal. In some embodiments, the sensor 1100 may also include a wireless link (e.g., Bluetooth®) (not shown) to provide an external server access to the sensor 1100 so as to exert at least some control on the sensor 1100.

Internally, in some embodiments, the sensor 1100 may include a microprocessor 1108 (which may be alternatively referred to as a micro-controller) that includes instructions thereon specifying how measurements (RF, ECG, accelerometer, etc.) are taken and the obtained data are transmitted, how to relay the status of the sensor 1100, how/when the sensor 1100 can enter the plurality of sleep levels, and/or the like. In some embodiments, the instructions may also specify the conditions for performing certain types of measurements. For example, the instructions may specify that the accelerometer may not commence measurements (for physical activity, and patient posture, for example) unless the user of the sensor is at rest or maintaining a certain posture. As another example, the instructions may identify the conditions that may have to be fulfilled before ECG measurements can commence, such conditions including at least sufficient attachment level between the sensor 1100 and the surface on the body to which the sensor 1100 is attached. In some embodiments, the microprocessor 1108 may have internal and external non-volatile memory banks that can be used for keeping measurement directory and data, scheduler information, and/or a log of actions and errors. This non-volatile memory allows saving power via a total power-down while retaining data and status information.

Figure 11B:
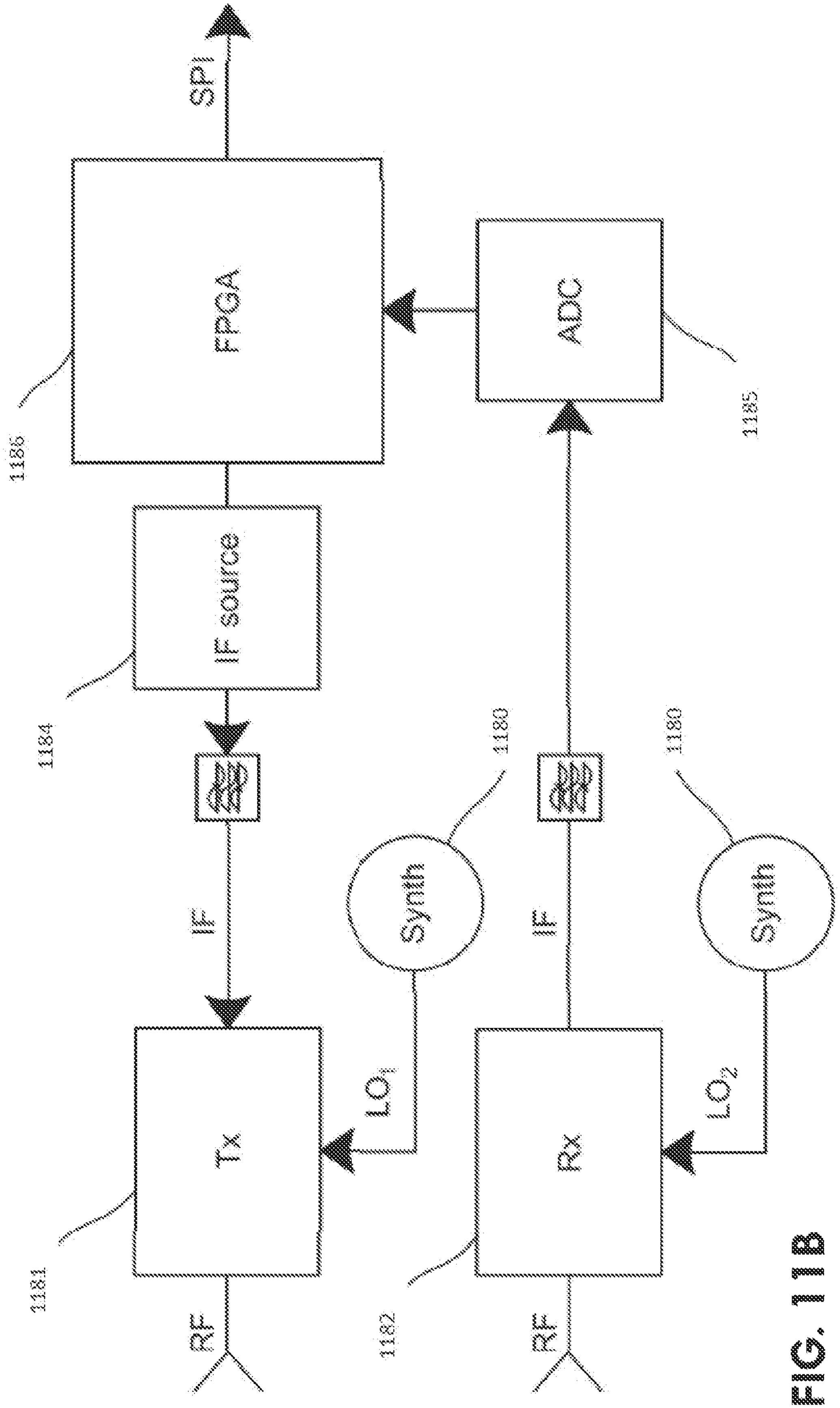
FIG. 11B shows a block diagram of example architecture of a radio frequency (RF) module, according to some embodiments.
Figure 11C:
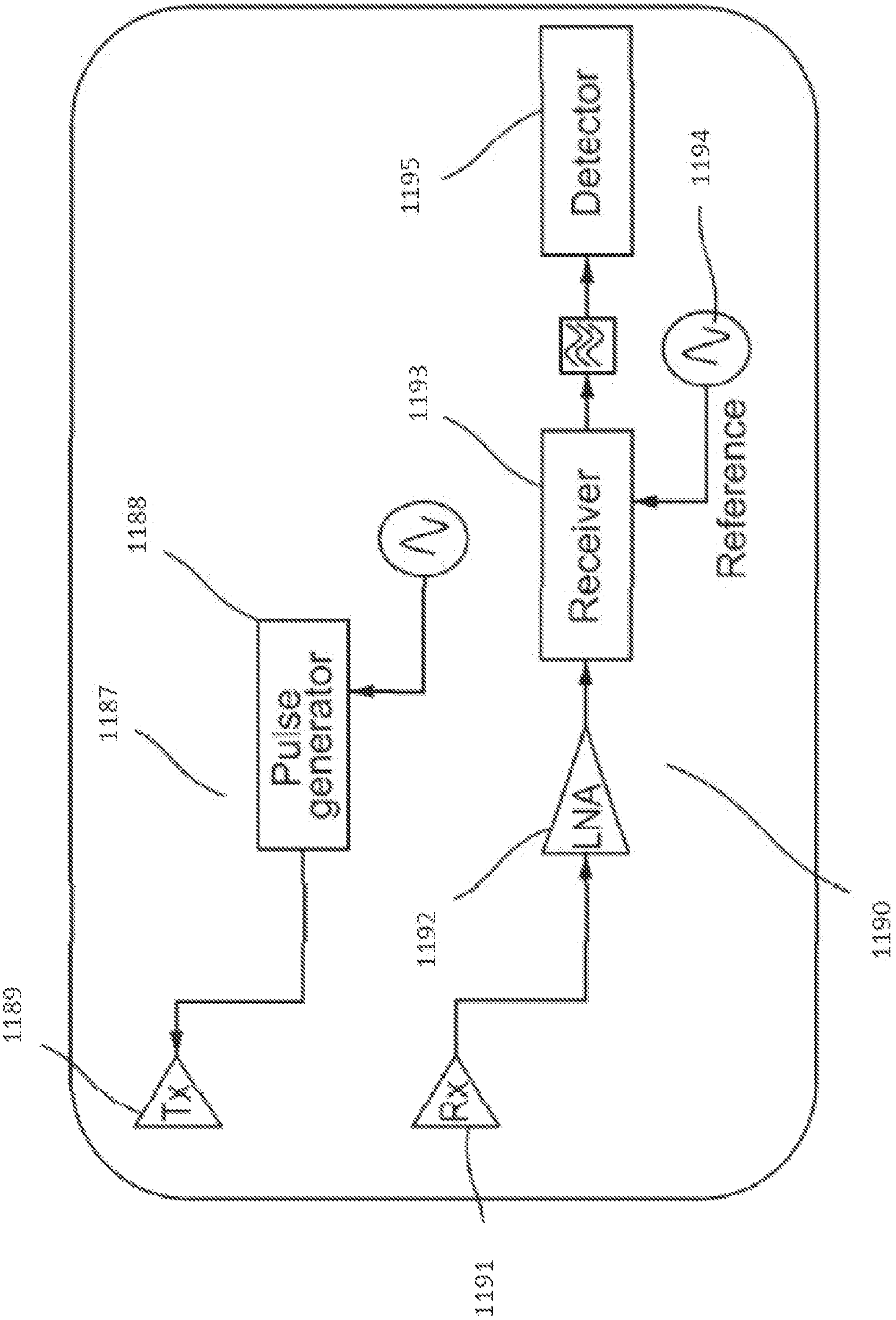
FIG. 11C shows a block diagram of another example architecture of an RF module, according to some embodiments.

FIGS. 11B and 11C are block diagrams that illustrate examples of RF sensor functionality disposed within an RF module (e.g., RF module 1132), according to some embodiments. As noted herein, such functionality may be used for RF based fluid monitoring of fluid accumulation/content in tissue in accordance with the techniques described herein. Referring first to FIG. 11B, initially, one or more RF signals (e.g., a single "LO" signal, or different "$LO_1$" and "$LO_2$" signals, collectively "LO" signals) can be generated by a broadband synthesizer 1180 (e.g., a pulse generator and synthesizer—LO). Such a synthesizer 1180 can preferably include moderate phase noise performance and fast settling time capabilities (in some embodiments, one or the other). The RF module 1132 includes a transmitter portion 1181, including a transmitting antenna (Tx) and associated circuitry for transmitting RF waves directed, for example, towards a tissue of interest in the patient's body, and a receiver portion 1182, including a receiver antenna (Rx) and associated circuitry for receiving reflected RF waves from, for example, the tissue of interest in the patient's body.

The LO signal at the transmitter (Tx) of the transmitter portion 1181 is multiplied with an external sine wave at a low frequency intermediate frequency (IF) signal, generated by an IF source 1184, and directed to the output of the transmitter (Tx). As noted above, the LO signal at the transmitter portion 1181 and the receiver portion 1182 can be generated by one or two LO sources (e.g., synthesizer(s) 1180). Output power can be controlled via digital control of a digitally controlled attenuator (DCA) on the RF transceiver path. An external reflected RF wave returning to a receiving antenna (Rx) is directed to the receiver portion and down-converted to an IF frequency by a down conversion mixer. The reflection characteristics (phase and amplitude) can be transformed to a new IF carrier (e.g., on the order of 250 KHz), filtered and amplified before the ADC 1185.

Digital control for the functionality in FIG. 11B may be achieved directly by a processor and/or digital logic (e.g., an FPGA 1186), which may be configured to control the transceiver's configuration process, IF signal adjustments, and associated switching.

Referring now to FIG. 11C, in some embodiments, the RF module 1132 may be implemented using a transmitting portion 1187 and receiver portion 1190 as shown. For example, the transmitting portion 1187 can include a pulse generator 1188 and a transmitting antenna Tx 1189 for transmitting the RF waves directed towards a tissue of interest in the patient's body. The receiver portion 1190 may include a receiving antenna Rx 1191, a low-noise RF amplifier 1192, a receiver 1193 that converts the reflected RF signals to an IF signal by using mixer and local oscillator 1194, which may be a monostatic (sheared LO) or a bi-static system. The signal can be filtered, amplified, and fed in to a detector 1195, the output of which may be connected to additional circuitry for further signal processing.

With respect to potential RF/ECG interference, in some embodiments the following steps can be taken:

Ground Separation between digital and RF components may be achieved by separating the digital and RF grounds, and utilizing a single connection point through ferrite bead.

RF module shielding may also be used, which may comprise a metallic cover, for example, radio frequency shield 1090 as shown in FIG. 10C.

Power circuitry considerations: different power paths may be utilized for different components/modules. Additionally, the power circuit may include filters to avoid noise.

ECG filtering may also be used to aid in minimizing RF interference which prevents high frequency signals interfering with the ECG circuitry/module.

Circuitry layout: ECG signal paths are physically separated from RF paths. In some embodiments, the ECG signal paths can also be physically separated from other lines that might interfere.

FIG. 11C shows an example general architecture of the RF module with low frequency IF and shared local oscillator (LO). As an example of some non-limiting embodiments, with reference to FIG. 11C, the transmitted RF signal may be mixed with the IF signal (e.g., about 250 KHz) before transmission, so the transmission is actually 2 tones around the carrier RF signal, separated by about 500 KHz.

In some embodiments, the RF module 1132 may include a calibration path (e.g., an electric reflector such as but not limited to a resistor on board) which generates a steady and constant or near-constant reflection uncorrelated with the external propagation path. This reflector generates a reflection profile with minimal dependencies to temperature, system noise, and device location on the body.

In some embodiments, the RF module 1132 itself may not have any processing components inside. For example, it may be controlled by a field-programmable gate array (FPGA) that defines in each or nearly each frequency point one or more of the frequency, output power levels, system gain, bypassing modes, and/or enable/disable transmissions.

In some embodiments, the RF module 1132 may support different types of waveform configurable options, including but not limited to normal operation, calibration frame operation, interleaved switching between normal and calibration frame operation, interleaved switching between normal and delayed path operation, and clear channel sensing. In some of these options, for example the normal and interleaved switching ones, the attenuation may be different per frequency, while in the case of clear channel sensing, there may not be any transmission. For the calibration frame operation, the attenuation can be the same for all frequencies but may be higher when compared to those of the normal operation.

In some embodiments, the transmit (Tx) and receive (Rx) switches may be respectively set to transmit and receive through a calibration path for the case of calibration frame operation, while for the clear channel sensing, Rx switch may be set to antenna and Tx to calibration path. For interleaved switching between normal and calibration frame operations and between normal and delayed path operations, in some embodiments, the Tx and Rx switches may alternate between calibration and antenna path per frequency, and normal and delayed path, respectively.

In some embodiments, the RF waves may be in the frequency ranges from about 100 MHz to about 1 GHz, 200 MHz to about 2.5 GHz, from about 200 MHz to about 3 GHz, from about 500 MHz to about 5 GHz, including values and subranges therebetween. In some embodiments, a thoracic fluid content (TFC) sensitivity may be configured to allow measurement of heart signals at distances up to about 25 cm, about 20 cm, about 15 cm, about 10 cm, about 5 cm, including values and subranges therebetween, inside the body onto which the disclosed sensor is attached. In some embodiments, the dynamic range is no less than 100 dB, measured in the presence of a strong coupling signal between transmission & reception. Further, the waveform may be stepped frequency (16-128 frequencies), arbitrary with 1 MHz accuracy and resolution. In some embodiments, actual frequencies selected may be contiguous or not, depending on regulatory requirements. In some embodiments, the dwell and settling times may be configurable to allow 16-128 frequencies within less than 5 to 20 ms, respectively.

Details on RF-based measurements of physiological parameters, such as thoracic fluid content, have been discussed in U.S. Patent Application Publication No.: US 2011/0130800, filed Apr. 14, 2010, titled "Methods and Systems for Determining Fluid Content of Tissue"; and PCT International Patent Publication No.: WO 2012/011066, filed Jul. 21, 2011, titled "Implantable Dielectrometer," the disclosures of which are incorporated by reference herein in their entireties.

It has been noted above that the sensor may include indicators providing information on the attachment level of the patch housing the sensor to a skin of the wearer of the sensor. Such information may be obtained from RF-based measurements as discussed in PCT International Patent Application Publication No. WO 2016/115175, filed Jan. 12, 2016, titled "Systems, Apparatuses, and Methods for Radio Frequency-Based Attachment Sensing," the disclosure of which is incorporated by reference herein in its entirety.

In some embodiments, the FPGA 1106, with a top-level view of which is shown in FIG. 11D, may be configured to interface with the RF module 1132. For example, the FPGA 1106 is configured to control one or more of the transceiver module, the RF discrete pins, the ADC module, generate the IF signal for the RF module 1132, and acquire ADC (analog-digital conversion) output samples, synchronized with the generated IF signal. Further, in some embodiments, the FPGA 1106 is configured to process the ADC output samples to generate the baseband data. In addition, in some embodiments, the FPGA 1106 may be configured to interface with the microcontroller or microprocessor 1108. For example, the FPGA 1106 may start RF transmission (per frame) upon command from microprocessor 1108, save baseband data to local RAM, per frame, for microprocessor 1108 to read, allow microprocessor 1108 read/write transactions towards configuration memory, provide a debug interface for the microprocessor 1108, and/or allow microprocessor 1108 to change configuration settings using a dedicated memory.

In some embodiments, the FPGA 1106 can support up to 128 frequencies, allowing for a different gain and dwell time per frequency. In some embodiments, power consumption can be minimized by using several clock frequencies within the design and gating unused clock signals. In some embodiments, microprocessor data acquisition can be performed using a separate clock, allowing the shut-down of the entire control and processing pipe while reading the data.

In some embodiments, the sensor disclosed herein may comprise an accelerometer and the accelerometer may be used to determine one or more of the physical activity, posture, and respiration rate of a patient wearing the sensor. For example, a three-axis (3D) accelerometer 1122 may be used to acquire data on patient movements and posture, as well as the respiration rate, and a processor (of the sensor or an external server, for example) receiving the acquired data may use the data (e.g., in conjunction with data obtained by the sensor such as ECG data or RF-based measurements) to determined physiological parameters of the patient, such as the lung fluid level of the patient. The 3D accelerometer 1122 may be used to aid RF and/or ECG analysis by detecting different types of motion segments in the recording so that the conditions of the measurements of the RF and/or the ECG may be interpreted/analyzed accordingly. For example, in some embodiments, RF and/or ECG measurements may be performed while the patient wearing the sensor is active or at rest. The analysis of the RF and/or ECG data may then depend on the state of the patient's physical activity (e.g., at rest, low intensity activity, high intensity activity, etc.). In such embodiments, the accelerometer 1122 may be used to identify the patient's physical state so as to properly analyze and interpret the RF and/or ECG measurements.

In some embodiments, the accelerometer 1122 may also contain an internal tap detector, which may be used for generating a patient triggered event (e.g., using "double tap" feature). The acceleration signal can be used to calculate respiration rate. FIG. 11A shows an example embodiment of a sensor comprising a 3D accelerometer 1122, RF antennas 1104*a*, 1104*b*, ECG processing circuitry coupled to ECG electrodes, a microcontroller 1108 (which may be alternatively referred to as microprocessor throughout this disclosure) and a telemetry (e.g., Bluetooth®) 1114. In such embodiments, for example, the microcontroller 1108 may receive data on patient respiration rate, movements, posture, and ECG, as well as RF-based measurements of the patient and process, and/or transmit to an external processor via the telemetry 1114 for further processing, to determine a physiological parameter of the patient. As an example, the microcontroller 1108 of the sensor may cause the Bluetooth® telemetry 1114 to transmit the noted data and measurements to an external server which in turn analyzes the RF measurements, the ECG, posture, movement, and/or respiration rate data to determine the lung fluid level of the patient. As an another example, the external server may analyze ECG data to determine patient health conditions related to one or more of a heart rate, atrial fibrillation, flutter, supraventricular tachycardia, ventricular tachycardia, pause, atrioventricular (AV) block, ventricular fibrillation, bigeminy, trigeminy, ventricular ectopic beats, supraventricular ectopic beats (SVEB), bradycardia, and tachycardia. The determination of patient physiological health parameters (e.g., lung fluid level or the above-noted health conditions) may allow the server to provide a notification on health-related events of the patient wearing the sensor for which the data came. For example, upon determining an arrhythmia condition from data received from a sensor, an external server may provide a notification indicating a cardiac event with respect to the wearer of the sensor that transmitted the data.

In some embodiments, the sensor may also include a temperature sensor, conductance sensor, a pressure sensor, a respiration sensor, SPO2, and/or a light sensor. For example, a respiration sensor can include an accelerometer configured to monitor the patient's chest movements, e.g., during certain portions of the day and/or night or during an RF measurement. For instance, a 3D multi-axis, multi-channel accelerometer can be configured to, on a first channel, monitor for a patient movement and/or posture, and on a second, different channel, monitor the chest movements of the patient to determine respiration rate and other related data. Alternatively, a respiration accelerometer can be provided in the device that is separate from a posture sensing accelerometer. In some examples, the respiration rate measurement can be based on the operation of a tri-axis microelectromechanical system (MEMS) accelerometer within the device mounted on the patient's torso. The accelerometer can measure projections of the gravity vector on its intrinsic axes. From these measurements, a respiration rate can be derived based on measured quasi-periodic changes of the projections that occur due to respiration movements of the patient's rib cage.

In other examples, the respiration rate and/or other respiration data can be derived from the RF signals themselves. For example, dedicated respiration circuitry can be provided and/or the processor can be configured with instructions to cause the processor to monitor the reflected RF waves, as described herein, and determine respiration rate and related data therefrom. In some embodiments, respiration characteristics, such as exhale vs. inhale times, can also be measured via an accelerometer and health conditions, such as sleep apnea, may be detected from accelerometer measurements.

In some embodiments, RR, which denotes ventricular interbeat interval on ECG, may be derived from ECG data and the RR accuracy can be improved by fusing the data from two or more of these RR measurement methods.

When using the disclosed sensor, in some embodiments, there are scenarios that involve the removal of the adhesive patch from the skin of a body, either by involving the transfer of sensors from old patient to new patient or when replacing faulty sensors. For example, when a device is in a charger or on a patient in error, it can be disassociated from the patient through a server action. Similarly, if the device is newly assigned to a patient, the device can be associated with a new patient through a server action. In some embodiments, certain operational modes of the sensor may not include all aspects of the sensor's operational capability. For example, situations involving automatic built-in tests, regulation tests, debugging, handling when the sensor is faulty, etc., one or more features of the sensor may not be activated or operational (or may operate differently than when the sensor is fully or normally operational) while the sensor itself is operating. For example, when debugging a faulty system, in some embodiments, transmission may be conducted via a single specific frequency by allowing configuring a specific frequency and triggering start/stop transmission.

| | |
|---|---|
| Overall dimensions | Smaller than about 55 mm × about 70 mm × about 17 mm |
| Maximum weight | Less than about 70 grams |
| ECG attachment | Embedded in adhesive patch |
| Gel | using hydrogel embedded in patch |
| Device liquid/dustproofing | Ultrasonic sealing, tested according to IP67 |
| Package | Contents: 1 device, charging cradle, User manual and disposable patches; Patches must be packed appropriately to avoid glue dehydration. |
| Labelling | Device should be labelled with serial number & FCC ID. Label must withstand environmental conditions according to IP67 |

-continued

| | |
|---|---|
| Soft feel | Rubber like feel, little or no sharp edges |
| Push-Button | Multipurpose; designed to be used by technician; protected from accidental activation by the patient to preserve power; Used for reset, pairing and to initiate communication |
| LED | Multipurpose; dual color; indicates battery status, pairing, errors, BT connection. |
| Device-in-patch sensing | electrical-connection |
| Buzzer | Audio notification, between about 1 and about 3 KHz and over about 60 dBSPL intensity at a distance of 1 m. |
| PCB placement and case closure | Without screws |
| Drop protection | Device is designed to comply with drop tests according to standard IEC 60601-1 and 60601-1-11 |

Figure 12:
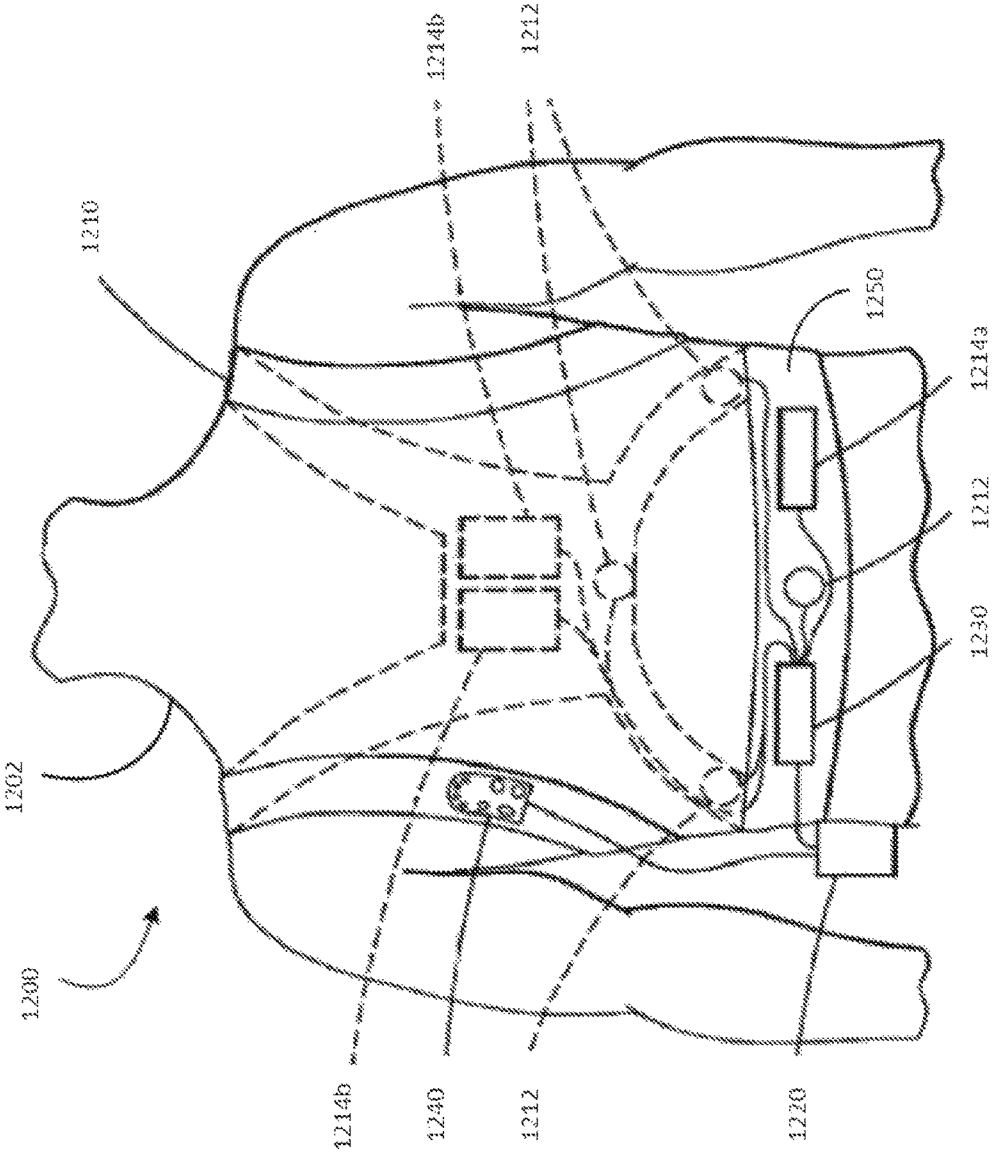
FIG. 12 illustrates an example medical device (e.g., external heart monitoring device) that is external, ambulatory, and wearable by a patient, according to some embodiments.

FIG. 12 illustrates an example wearable heart monitoring device, e.g., medical device 1200 that is external, ambulatory, and wearable by a patient 1202, and configured to implement one or more configurations described herein. For example, the medical device 1200 can be a non-invasive medical device configured to be located substantially external to the patient 1202. Such a medical device 1200 can be, for example, an ambulatory medical device that is capable of and designed for moving with the patient 1202 as the patient 1202 goes about his or her daily routine. For example, the medical device 1200, as described herein, can be bodily-attached to the patient 1202, such as the LifeVest® wearable cardioverter defibrillator available from ZOLL® Medical Corporation. In one example scenario, such wearable defibrillators can be worn nearly continuously or substantially continuously for two to three months at a time. During the period of time in which they are worn by the patient 1202, the wearable defibrillator can be configured to continuously or substantially continuously monitor the vital signs of the patient 1202 and, upon determination that treatment is required, can be configured to deliver one or more therapeutic electrical pulses to the patient 1202. For example, such therapeutic shocks can be pacing, defibrillation, or transcutaneous electrical nerve stimulation (TENS) pulses.

The medical device 1200 can include one or more of the following: a garment 1210, one or more sensing electrodes 1212 (e.g., ECG electrodes), one or more therapy electrodes 1214*a* and 1214*b* (collectively referred to herein as therapy electrodes 1214), a medical device controller 1220, a connection pod 1230, a patient interface pod 1240, a belt 1250, or any combination of these. In some examples, at least some of the components of the medical device 1200 can be configured to be affixed to the garment 1210 (or in some examples, permanently integrated into the garment 1210), which can be worn about the patient's torso.

The medical device controller 1220 can be operatively coupled to the sensing electrodes 1212, which can be affixed to the garment 1210, e.g., assembled into the garment 1210 or removably attached to the garment 1210, e.g., using hook and loop fasteners. In some implementations, the sensing electrodes 1212 can be permanently integrated into the garment 1210. The medical device controller 1220 can be operatively coupled to the therapy electrodes 1214. For example, the therapy electrodes 1214 can also be assembled into the garment 1210 or, in some implementations, the therapy electrodes 1214 can be permanently integrated into the garment 1210.

Component configurations other than those shown in FIG. 12 are possible. For example, the sensing electrodes 1212 can be configured to be attached at various positions about the body of the patient 1202. The sensing electrodes 1212 can be operatively coupled to the medical device controller 1220 through the connection pod 1230. In some implementations, the sensing electrodes 1212 can be adhesively attached to the patient 1202. In some implementations, the sensing electrodes 1212 and at least one of the therapy electrodes 1214 can be included on a single integrated patch and adhesively applied to the patient's body.

The sensing electrodes 1212 can be configured to detect one or more cardiac signals. Examples of such signals include ECG signals and/or other sensed cardiac physiological signals from the patient 1202. In certain implementations, the sensing electrodes 1212 can include additional components, such as accelerometers, acoustic signal detecting devices, and other measuring devices, for recording additional parameters. For example, the sensing electrodes 1212 can also be configured to detect other types of patient physiological parameters and acoustic signals, such as tissue fluid levels, heart vibrations, lung vibrations, respiration vibrations, patient movement, etc. Example sensing electrodes 1212 include a metal electrode with an oxide coating such as tantalum pentoxide electrodes, as described in, for example, U.S. Pat. No. 6,253,099 entitled "Cardiac Monitoring Electrode Apparatus and Method," the disclosure of which is incorporated by reference herein in its entirety.

In some examples, the therapy electrodes 1214 can also be configured to include sensors configured to detect ECG signals, as well as other physiological signals of the patient. The connection pod 1230 can, in some examples, include a signal processor configured to amplify, filter, and digitize these cardiac signals prior to transmitting the cardiac signals to the medical device controller 1220. One or more of the therapy electrodes 1214 can be configured to deliver one or more therapeutic defibrillating shocks to the body of the patient 1202 when the medical device 1200 determines that such treatment is warranted based on the signals detected by the sensing electrodes 1212 and processed by the medical device controller 1220. Example therapy electrodes 1214 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1214 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 13:
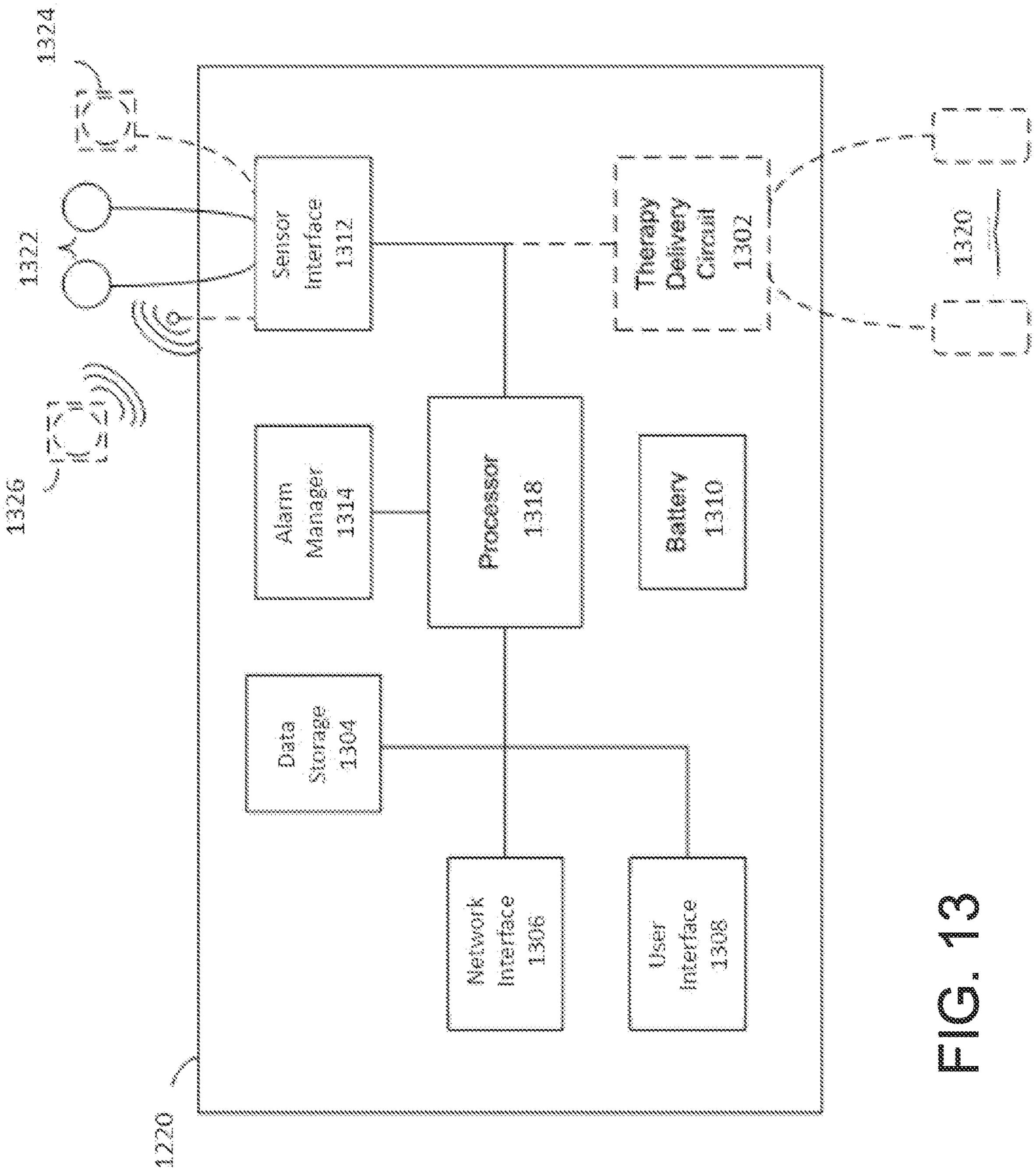
FIG. 13 illustrates an example component-level view of a medical device (e.g., external heart monitoring device), according to some embodiments.

Referring now to FIG. 13, FIG. 13 illustrates a sample component-level view of the medical device controller 1220. As shown in FIG. 13, the medical device controller 1220 can include a therapy delivery circuit 1302, a data storage 1304, a network interface 1306, a user interface 1308, at least one battery 1310, a sensor interface 1312, an alarm manager 1314, and least one processor 1318. A patient monitoring medical device can include a medical device controller 1220 that includes like components as those described above, but does not include the therapy delivery circuit 1302 (shown in dotted lines).

The therapy delivery circuit 1302 can be coupled to one or more electrodes 1320 configured to provide therapy to the patient (e.g., therapy electrodes 1214 as described above in connection with FIG. 12). For example, the therapy delivery circuit 1302 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 1318) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four, or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 1302 can be configured to perform the switching and pulse delivery operations, e.g., under control of the processor 1318. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 1304 can include one or more of non-transitory computer readable media, such as flash memory, solid state memory, magnetic memory, optical memory, cache memory, combinations thereof, and others. The data storage 1304 can be configured to store executable instructions and data used for operation of the medical device controller 1220. In certain implementations, the data storage 1304 can include executable instructions that, when executed, are configured to cause the processor 1318 to perform one or more functions.

In some examples, the network interface 1306 can facilitate the communication of information between the medical device controller 1220 and one or more other devices or entities over a communications network. For example, where the medical device controller 1220 is included in an ambulatory medical device (such as medical device 1200), the network interface 1306 can be configured to communicate with a remote computing device such as a remote server or other similar computing device. The network interface 1306 can include communications circuitry for transmitting data in accordance with a Bluetooth® wireless standard for exchanging such data over short distances to an intermediary device(s) (e.g., a base station, a "hotspot" device, a smartphone, a tablet, a portable computing device, and/or other devices in proximity of the wearable medical device 1200). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi® communications link based on the IEEE 802.11 standard.

In certain implementations, the user interface 1308 can include one or more physical interface devices such as input devices, output devices, and combination input/output devices and a software stack configured to drive operation of the devices. These user interface elements may render visual, audio, and/or tactile content. Thus, the user interface 1308 may receive input or provide output, thereby enabling a user to interact with the medical device controller 1220.

The medical device controller 1220 can also include at least one battery 1310 configured to provide power to one or more components integrated in the medical device controller 1220. The battery 1310 can include a rechargeable multi-cell battery pack. In one example implementation, the battery 1310 can include three or more 13200 mAh lithium ion cells that provide electrical power to the other device components within the medical device controller 1220. For example, the battery 1310 can provide its power output in a range of between 20 mA to 1000 mA (e.g., 40 mA) output and can support 24 hours, 48 hours, 72 hours, or more of runtime between charges. In certain implementations, the battery capacity, runtime, and type (e.g., lithium ion, nickel-cadmium, or nickel-metal hydride) can be changed to best fit the specific application of the medical device controller 1220.

The sensor interface 1312 can be coupled to one or more sensors configured to monitor one or more physiological parameters of the patient. As shown, the sensors may be coupled to the medical device controller 1220 via a wired or wireless connection. The sensors can include one or more electrocardiogram (ECG) electrodes 1322 (e.g., similar to sensing electrodes 1212 as described above in connection with FIG. 12), heart vibrations sensors 1324, and tissue fluid monitors 1326 (e.g., based on ultra-wide band radiofrequency devices).

The ECG electrodes 1322 can monitor a patient's ECG information. For example, the ECG electrodes 1322 can be galvanic (e.g., conductive) and/or capacitive electrodes configured to measure changes in a patient's electrophysiology to measure the patient's ECG information. The ECG electrodes 1322 can transmit information descriptive of the ECG signals to the sensor interface 1312 for subsequent analysis.

The heart vibrations sensors 1324 can detect a patient's heart vibration information. For example, the heart vibrations sensors 1324 can be configured to detect heart vibration values including any one or all of S1, S2, S3, and S4. From these heart vibration values, certain heart vibration metrics may be calculated, including any one or more of electromechanical activation time (EMAT), percentage of EMAT (% EMAT), systolic dysfunction index (SDI), and left ventricular systolic time (LVST). The heart vibrations sensors 1324 can include an acoustic sensor configured to detect vibrations from a subject's cardiac system and provide an output signal responsive to the detected heart vibrations. The heart vibrations sensors 1324 can also include a multi-channel accelerometer, for example, a three channel accelerometer configured to sense movement in each of three orthogonal axes such that patient movement/body position can be detected and correlated to detected heart vibrations information. The heart vibrations sensors 1324 can transmit information descriptive of the heart vibrations information to the sensor interface 1312 for subsequent analysis.

The tissue fluid monitors 1326 can use radio frequency (RF) based techniques to assess fluid levels and accumulation in a patient's body tissue. For example, the tissue fluid monitors 1326 can be configured to measure fluid content in the lungs, typically for diagnosis and follow-up of pulmonary edema or lung congestion in heart failure patients. The tissue fluid monitors 1326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 1326 can transmit information descriptive of the tissue fluid levels to the sensor interface 1312 for subsequent analysis.

The sensor interface 1312 can be coupled to any one or a combination of sensing electrodes/other sensors to receive other patient data indicative of patient parameters. Once data from the sensors has been received by the sensor interface 1312, the data can be directed by the processor 1318 to an appropriate component within the medical device controller 1220. For example, if heart data is collected by heart vibrations sensor 1324 and transmitted to the sensor interface 1312, the sensor interface 1312 can transmit the data to the processor 1318 which, in turn, relays the data to a cardiac event detector. The cardiac event data can also be stored on the data storage 1304.

In certain implementations, the alarm manager 1314 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 1314 can be implemented using hardware or a combination of hardware and software. For instance, in some examples, the alarm manager 1314 can be implemented as a software component that is stored within the data storage 1304 and executed by the processor 1318. In this example, the instructions included in the alarm manager 1314 can cause the processor 1318 to configure alarm profiles and notify intended recipients using the alarm profiles. In other examples, alarm manager 1314 can be an application-specific integrated circuit (ASIC) that is coupled to the processor 1318 and configured to manage alarm profiles and notify intended recipients using alarms specified within the alarm profiles. Thus, examples of alarm manager 1314 are not limited to a particular hardware or software implementation.

In some implementations, the processor 1318 includes one or more processors (or one or more processor cores) that each are configured to perform a series of instructions that result in manipulated data and/or control the operation of the other components of the medical device controller 1220. In some implementations, when executing a specific process (e.g., cardiac monitoring), the processor 1318 can be configured to make specific logic-based determinations based on input data received, and be further configured to provide one or more outputs that can be used to control or otherwise inform subsequent processing to be carried out by the processor 1318 and/or other processors or circuitry with which processor 1318 is communicatively coupled. Thus, the processor 1318 reacts to specific input stimulus in a specific way and generates a corresponding output based on that input stimulus. In some example cases, the processor 1318 can proceed through a sequence of logical transitions in which various internal register states and/or other bit cell states internal or external to the processor 1318 may be set to logic high or logic low. As referred to herein, the processor 1318 can be configured to execute a function where software is stored in a data store coupled to the processor 1318, the software being configured to cause the processor 1318 to proceed through a sequence of various logic decisions that result in the function being executed. The various components that are described herein as being executable by the processor 1318 can be implemented in various forms of specialized hardware, software, or a combination thereof. For example, the processor 1318 can be a digital signal processor (DSP) such as a 24-bit DSP processor. The processor 1318 can be a multi-core processor, e.g., having two or more processing cores. The processor 1318 can be an Advanced RISC Machine (ARM) processor such as a 32-bit ARM processor. The processor 1318 can execute an embedded operating system, and include services provided by the operating system that can be used for file system manipulation, display and audio generation, basic networking, firewalling, data encryption, and communications.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, computer program product, article, material, kit, and/or method described herein. In addition, any combination of two or more such features, systems, computer program products, articles, materials, kits, and/or methods, if such features, systems, computer program products, articles, materials, kits, and/or methods are not mutually inconsistent, is included within the inventive scope of the present disclosure. Embodiments disclosed herein may also be combined with one or more features, as well as complete systems, computer program products, devices, and/or methods, to yield yet other embodiments and inventions. Moreover, some embodiments may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable electrocardiogram (ECG) lead arrhythmia monitoring system for identifying arrhythmias experienced by a patient, comprising:

an external wearable heart monitoring device configured for continuous and long-term monitoring of the patient comprising:

a plurality of ECG electrodes and associated circuitry configured to sense surface ECG activity of the patient, wherein the plurality of ECG electrodes and associated circuitry are configured to provide at least one ECG channel producing at least one ECG signal for the patient; and a non-transitory computer-readable medium comprising an arrhythmia classifier comprising at least one neural network, wherein the at least one neural network is trained based on:

a historical collection of a plurality of ECG signal portions, annotation data comprising a plurality of annotations associated with the plurality of ECG signal portions, the plurality of annotations comprising at least one respective annotation for each respective ECG signal portion of the plurality of ECG signal portions, and weight data for the annotation data of the plurality of ECG signal portions, the weight data comprising a respective weight for each respective annotation based on a respective annotator of the respective annotation, the respective weight for each respective annotator based on a respective score of the respective annotator; and at least one processor operatively connected to the at least one ECG channel and the non-transitory computer-readable medium, the at least one processor configured to:

receive the at least one ECG signal of the at least one ECG channel;

monitor the at least one ECG signal to detect at least one arrhythmia event based on the arrhythmia classifier; and transmit at least one communication based on the at least one arrhythmia event to a remote computer system.

2. The system of claim 1, wherein the plurality of ECG electrodes comprises at least three ECG electrodes, wherein the at least three ECG electrodes comprise a right arm (RA) EGG electrode, a left arm (LA) ECG electrode, and a left leg (LL) ECG electrode, wherein the at least one ECG channel comprises a lead I channel between the RA ECG electrode and the LA ECG electrode, a lead II channel between the RCA ECG electrode and the LL ECG electrode, and a lead III channel between the LA ECG electrode and the LL ECG electrode.

3. The system of claim 1, wherein the external wearable heart monitoring device comprises a single adhesive patch.

4. The system of claim 1, wherein the respective score for each respective annotator is based on a respective skill level of the respective annotator.

5. The system of claim 1, wherein the respective score for each respective annotator score comprises one of:

an integer value from one to four;

an integer value from one to five;

an integer value from one to ten;

an integer value from one to 100;

one of 25, 50, 75, or 100; or a value from zero to one.

6. The system of claim 1, wherein the remote computer system is configured to:

receive a plurality of scores comprising the respective score for each respective annotator, wherein a plurality of annotators comprises each respective annotator;

determine the respective weight for each respective annotator based on the plurality of scores;

receive the historical collection of the plurality of ECG signal portions with the annotation data; and train the arrhythmia classifier based on the historical collection of the plurality of ECG signal portions with the annotation data and based on the weight data.

7. The system of claim 6, wherein the at least one communication comprises at least one further ECG signal portion associated with the at least one arrhythmia event;

wherein the remote computer system is further configured to:

receive the at least one communication comprising the at least one further ECG signal portion;

receive further annotation data associated with the at least one further ECG signal portion from at least one annotator of the plurality of annotators;

compare the further annotation data to the at least one arrhythmia event detected based on the arrhythmia classifier;

determine an updated weight for each respective annotator of the at least one annotator based on comparing the further annotation data to the at least one arrhythmia event; and retrain the arrhythmia classifier based on the at least one further ECG signal portion, the further annotation data, and the updated weight data.

8. The system of claim 6, wherein training the arrhythmia classifier comprises updating parameters of the at least one neural network based on a loss function comprising a hyperparameter based on the respective weight for the respective annotation.

9. The system of claim 1, wherein, during training, parameters of the at least one neural network are updated based on a loss function comprising a hyperparameter based on the respective weight for the respective annotation.

* * * * *